US008986961B2

(12) United States Patent
Verseck et al.

(10) Patent No.: US 8,986,961 B2
(45) Date of Patent: Mar. 24, 2015

(54) FERMENTATIVE PRODUCTION OF ACETONE FROM RENEWABLE RESOURCES BY MEANS OF NOVEL METABOLIC PATHWAY

(75) Inventors: Stefan Verseck, Hilden (DE); Steffen Schaffer, Herten (DE); Werner Freitag, Dorsten (DE); Friedrich-Georg Schmidt, Haltern am See (DE); Matthias Orschel, Muenster (DE); Gerda Grund, Coesfeld (DE); Wilfried Schmidt, Gelsenkirchen-Buer (DE); Hubert Johannes Bahl, Rostock (DE); Ralf-Joerg Fischer, Kritzmow (DE); Antje May, Rostock (DE); Peter Duerre, Ulm (DE); Simone Lederle, Ulm (DE)

(73) Assignee: Evonik Degussa GmbH, Essen (DE)

( * ) Notice: Subject to any disclaimer, the term of this patent is extended or adjusted under 35 U.S.C. 154(b) by 212 days.

(21) Appl. No.: 12/679,488

(22) PCT Filed: Oct. 1, 2008

(86) PCT No.: PCT/EP2008/063150
§ 371 (c)(1), (2), (4) Date: Mar. 23, 2010

(87) PCT Pub. No.: WO2009/056423
PCT Pub. Date: May 7, 2009

(65) Prior Publication Data

US 2010/0261237 A1 Oct. 14, 2010

(30) Foreign Application Priority Data

Nov. 2, 2007 (DE) ........................ 10 2007 052 463

(51) Int. Cl.
*C12P 7/26* (2006.01)
*C12P 7/28* (2006.01)
*C12N 9/16* (2006.01)
*C12N 9/00* (2006.01)

(52) U.S. Cl.
CPC ... *C12P 7/28* (2013.01); *C12N 9/16* (2013.01); *C12N 9/93* (2013.01); *C12Y 301/02* (2013.01); *C12Y 301/02018* (2013.01)
USPC .......................................... 435/150; 435/148

(58) Field of Classification Search
None
See application file for complete search history.

(56) References Cited

U.S. PATENT DOCUMENTS

| | | | |
|---|---|---|---|
| 8,604,227 | B2 | 12/2013 | Petrat et al. |
| 2008/0293125 | A1 | 11/2008 | Subbian et al. |
| 2010/0068773 | A1 | 3/2010 | Marx et al. |
| 2010/0190219 | A1 | 7/2010 | Schaffer et al. |
| 2010/0190224 | A1 | 7/2010 | Poetter et al. |
| 2010/0291644 | A1 | 11/2010 | Marx et al. |
| 2010/0324257 | A1 | 12/2010 | Karau et al. |
| 2011/0039313 | A1 | 2/2011 | Verseck et al. |
| 2011/0118433 | A1 | 5/2011 | Pötter et al. |
| 2011/0118504 | A1 | 5/2011 | Haas et al. |
| 2011/0171702 | A1 | 7/2011 | Reinecke et al. |
| 2011/0189742 | A1 | 8/2011 | Haas et al. |
| 2011/0251399 | A1 | 10/2011 | Dingerdissen et al. |
| 2011/0257429 | A1 | 10/2011 | Schraven et al. |
| 2011/0269977 | A1 | 11/2011 | Dingerdissen et al. |
| 2012/0034665 | A1 | 2/2012 | Haas et al. |
| 2012/0041216 | A1 | 2/2012 | Sieber et al. |
| 2012/0245375 | A1 | 9/2012 | Hannen et al. |
| 2012/0264182 | A1 | 10/2012 | Reinecke et al. |
| 2013/0092233 | A1 | 4/2013 | Pawlik et al. |
| 2013/0130319 | A1 | 5/2013 | Schaffer et al. |
| 2013/0165672 | A1 | 6/2013 | Klasovsky et al. |
| 2013/0165685 | A1 | 6/2013 | Hannen et al. |
| 2013/0183725 | A1 | 7/2013 | Poetter et al. |
| 2013/0245276 | A1 | 9/2013 | Klasovsky et al. |
| 2013/0261343 | A1 | 10/2013 | Orschel et al. |
| 2013/0331580 | A1 | 12/2013 | Klasovsky et al. |

FOREIGN PATENT DOCUMENTS

| | | |
|---|---|---|
| WO | 2008 131286 | 10/2008 |

OTHER PUBLICATIONS

Ngo et al. in the Protein Folding Problem and Tertiary Structure Prediction, 1994, Merz et al. (ed.), Birkhauser, Boston, MA, pp. 433 and 492-495.*

Bermejo, Lourdes L. et al., "Expression of *Clostridium acetobutylicum* ATCC 824 Genes in *Escherichia coli* for Acetone Production and Acetate Detoxification", Applied and Environmental Microbiology, American Society for Microbiology, vol. 64, No. 3, pp. 1079-1085, (Mar. 1, 1998).

(Continued)

*Primary Examiner* — Richard Hutson

(74) *Attorney, Agent, or Firm* — Oblon, Spivak, McClelland, Maier & Neustadt, L.L.P.

(57) ABSTRACT

The invention describes a process for preparing acetone starting from acetyl-coenzyme A comprising process steps A. enzymatic conversion of acetyl-CoA into acetoacetyl-CoA B. enzymatic conversion of acetoacetyl-CoA into acetoacetate and CoA and C. decarboxylation of acetoacetate to acetone and $CO_2$, which is characterized in that the coenzyme A is not transferred in process step B to an acceptor molecule. In addition, process step B is surprisingly catalyzed by enzymes of the classes of acyl-CoA thioesterase, acyl-CoA synthetase or acyl-CoA thiokinase.

Figure 1:
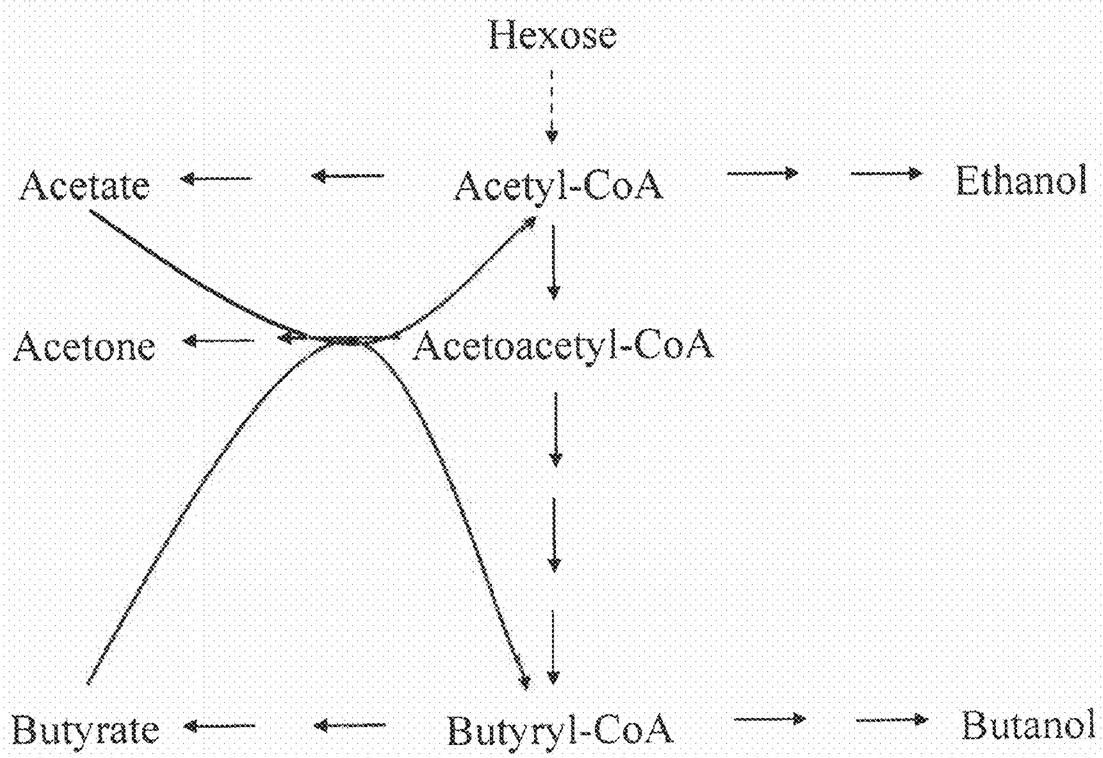

A completely novel metabolic pathway is concerned, because the enzymatic hydrolysis of acetoacetyl-CoA without simultaneous transfer of CoA to a receptor molecule has never previously been described for any microbial enzyme.

10 Claims, 12 Drawing Sheets

(56) References Cited

OTHER PUBLICATIONS

Zhuang, Zhihao et al., "The YbgC protein encoded by the ybgC gene of the tol-pal gene cluster of *Haemophilus influenzae* catalyzes acyl-coenzyme A thioester hydrolysis", FEBS Letters, Elsevier, vol. 516, No. 1-3, pp. 161-163, (Apr. 10, 2002).
Aneja, Punita et al., "Identification of an Acetoacetyl Coenzyme A Synthetase-Dependent Pathway for Utilization of L-(+)-3-Hydroxybutyrate in *Sinorhizobium meliloti*", Journal of Bacteriology, vol. 184, No. 6, pp. 1571-1577, (Mar. 2002).
Schwarzer, Dirk et al., "Regeneration of misprimed nonribosomal peptide synthetases by type II thioesterases", Proceedings of the National Academy of Sciences of the United States of America, PNAS, vol. 99, No. 22, pp. 14083-14088, (Oct. 29, 2002).
Woods, David R. "The genetic engineering of microbial solvent production", Trends in Biotechnology, Elsevier, vol. 13, No. 7, pp. 259-264, (Jul. 1, 1995).
U.S. Appl. No. 13/260,012, filed Sep. 23, 2011, Becker, et al.
U.S. Appl. No. 14/126,607, filed Dec. 16, 2013, Haas, et al.
U.S. Appl. No. 14/233,505, filed Jan. 17, 2014, Poetter, et al.
U.S. Appl. No. 14/237,121, filed Feb. 4, 2014, Haas, et al.
U.S. Appl. No. 14/238,576, filed Feb. 12, 2014, Schaffer, et al.
U.S. Appl. No. 14/238,594, filed Feb. 12, 2014, Schaffer, et al.
U.S. Appl. No. 14/110,450, filed Oct. 8, 2013, Klasovsky, et al.
U.S. Appl. No. 14/116,233, filed Nov. 7, 2013, Orschel, et al.
U.S. Appl. No. 14/124,486, filed Dec. 6, 2013, Nitz, et al.
U.S. Appl. No. 13/642,412, filed Oct. 19, 2012, Poetter, et al.
U.S. Appl. No. 13/721,481, filed Dec. 20, 2012, Gielen, et al.
Acetoacetate decarboxylase (ADC) at http://www.ncbi.nlm.nih.gov/Structure/cdd/cddsrv.cgi?uid=pfam06314 PubMed References tab, accessed Nov. 26, 2012 (2 pp.).
Thiolase at http://www.ncbi.nim.nih.gov/Structure/cdd/cddsrv.cgi?uid=cd00751 Conserved Features/Sites tab, accessed Nov. 26, 2012, (2 pp.).
Thiolase at http://www.ncbi.nim.nih.gov/Structure/cdd/cddsrv.cgi?uid=cd00751 PubMed References tab, accessed Dec. 3, 2012 (2 pp.).
4HBT at http://www.ncbi.nlm.nih.gov/Structure/cdd/cddsrv.cgi?uid=cd00586 Conserved Features/Sites tab, Accessed Nov. 26, 2012 (2 pp.).
4HBT at http://www.ncbi.nlm.nih.gov/Structure/cdd/cddsrv.cgi?uid=cd00586 PubMed References tab, Accessed Dec. 3, 2012 (2 pp.).
Dillion et al, "The Hotdog fold: wrapping up a superfamily of thioesterases and dehydraases", at http://www.biomedcentral.com/1417-2105/5/109 Open access published 2004 (14 pp.).
Heath et al, "The Claisen condensation in biology", Nat. Prod. Rep., 2002, vol. 19, pp. 581-596.
Modis et al, "Crystallographic Analysis of the Reaction Pathway of *Zoogloea ramigera* Biosynthetic Thiolase", J. Mol. Biol., 2000, vol. 297, pp. 1171-1182.
U.S. Appl. No. 14/363,178, filed Jun. 5, 2014, Haas, et al.
U.S. Appl. No. 14/363,165, filed Jun. 5, 2014, Pfeffer, et al.
U.S. Appl. No. 14/367,610, filed Jun. 20, 2014, Haas, et al.
U.S. Appl. No. 14/373,089, filed Jul. 18, 2014, Engel, et al.
U.S. Appl. No. 14/380,483, filed Aug. 22, 2014, Schiemann, et al.

* cited by examiner

Hexose
Acetate
Acetyl-CoA
Ethanol
Acetone
Acetoacetyl-CoA
Butyrate
Butyryl-CoA
Butanol kDa
M
1
2
3
116
66
45
35
25
18.4
14.4
Intein-YbgC fusion protein
ca. 70 kDa
CE
FT
W
Eluate
kDa
116
66
45
35
25
18.4
14.4
Intein-YbgC fusion protein
Intein
YbgC

FERMENTATIVE PRODUCTION OF ACETONE FROM RENEWABLE RESOURCES BY MEANS OF NOVEL METABOLIC PATHWAY

CROSS-REFERENCE TO RELATED APPLICATIONS

The present application is a 35 U.S.C. §371 National Stage patent application of International patent application PCT/EP2008/063150, filed on Oct. 1, 2008, which claims priority to German patent application DE 102007052463.5, filed on Nov. 2, 2007.

FIELD OF THE INVENTION

The invention relates to a novel enzymatic biosynthetic pathway for the production of acetone which, in contrast to conventional fermentation processes is uncoupled from the formation of ethanol and butanol, and to the enzymes and nucleic acids used for this purpose.

PRIOR ART

ABE Process in *Clostridium*

The conventional ABE fermentation process, i.e. the microbial production of acetone, butanol and ethanol, was for a long time the second largest biotechnological process in the world, immediately after ethanol fermentation with yeasts. Commercial ABE fermentation started in 1916 in England, where inter alia Chaim Weizmann discovered the ability of *Clostridium acetobutylicum* to form the solvents acetone, butanol and ethanol. The process was used in the western world until the late 1950s, and in South Africa even until 1981.

Two principal reasons are responsible for abandonment of this process: firstly, chemical synthesis of acetone and butanol became increasingly favourable, and secondly the price of the substrates for the fermentation increased greatly. The price of molasses in particular rose greatly through its use as addition to cattle feed.

The rising costs of petrochemical precursors, and novel technological possibilities in the area of pathway engineering of microorganisms are now revealing new options for the development of high-performance strains and commercial fermentation processes for producing solvents such as acetone.

Conventional ABE fermentation is based on the organisms *Clostridium acetobutylicum* and *Clostridium beijerinckii*. Both are Gram-positive and grow under strictly anaerobic conditions. These organisms are able to convert mono-, di- and poly-saccharides, the substrates principally used in the fermentation being molasses and starch.

The fermentation process with *C. acetobutylicum* is divided into two phases. In the first phase, the biomass formation proceeds together with the formation of acetate, butyrate and traces of ethanol ("acidogenic phase"). In the second phase, the so-called "solventogenic phase", the acids are then used to form the fermentation products acetone, butanol and ethanol (ABE). The products acetone, butanol and ethanol are formed in the ratio of approximately 3:6:1 in wild-type *C. acetobutylicum*. This product ratio may vary widely depending on the chosen culturing conditions (e.g. pH or nutrient supply) or substrates employed.

The enzymes of the biosynthesis of the solvents acetone, butanol and ethanol have been largely purified and biochemically characterized (cf. FIG. 1; Duerre, P., and Bahl, H. 1996. Microbial production of acetone/butanol/isopropanol. In: Biotechnology, vol. 6, 2nd ed. M. Roehr, (ed.), VCH Verlagsgesellschaft mbH, Weinheim, Germany. p. 229-268. Duerre, P. 1998. New insights and novel developments in clostridial acetone/butanol/isopropanol fermentation. Appl. Microbiol. Biotechnol. 49: 639-648). The genome sequence of *C. acetobutylicum* is also available (Noelling, J., Breton, G., Omelchenko, M. V. & 16 other authors (2001). Genome sequence and comparative analysis of the solvent producing bacterium *Clostridium acetobutylicum*. J Bacteriol 183, 4823-4838).

In recent years, a number of genetic tools making targeted pathway engineering possible has been developed. At present, three different, stably obtained replicons (pIM13, pCBU2 and pAMβ1; Lee et al. (1992). Vector construction, transformation, and gene amplification in *Clostridium acetobutylicum* ATCC 824. Ann. N.Y. Acad. Sci. 665: 39-51; Minton et al. (1993). Clostridial cloning vectors. In: The clostridia and biotechnology (D. R. Woods; editor). Butterworth-Heinemann. Stoneham, USA. pages 119-150) and two antibiotic resistance markers for erythromycin and thiamphenicol are available (Green and Bennett (1998). Genetic manipulation of acid and solvent formation in *Clostridium acetobutylicum* ATCC 824. Biotechnol. Bioeng. 58:215-21).

On the other hand, methods such as insertion inactivation or gene deletions cannot yet be carried out routinely, and even the antisense-based inhibition of gene expression in this group of organisms varies in efficiency and is never complete (Desai and Papoutsakis (1999). Antisense RNA strategies for metabolic engineering of *Clostridium acetobutylicum*. Appl. Environ. Microbiol. 65:936-45; Tummala et al. (2003). Antisense RNA downregulation of coenzyme A transferase combined with alcohol-aldehyde dehydrogenase overexpression leads to predominantly alcohologenic *Clostridium acetobutylicum* fermentations. J. Bacteriol. 185:3644-53). A number of publications describes the metabolic engineering both of the "solventogenic" and of the "acidogenic" biosynthetic pathway. Inactivation of the genes buk (butyrate kinase) or pta (phosphotransacetylase) led to drastic reductions in the concentrations of butyrate and acetate, respectively (Green et al. (1996). Genetic manipulation of acid formation pathways by gene inactivation in *Clostridium acetobutylicum* ATCC 824. Microbiology. 142:2079-86; Harris et al. (2000).

Characterization of recombinant strains of the *Clostridium acetobutylicum* butyrate kinase inactivation mutant: need for new phenomenological models for solventogenesis and butanol inhibition? Biotechnol. Bioeng. 67:1-11). Nevertheless, butyrate and acetate was formed by these mutants because the enzymes acetate kinase and phosphotransbutyrylase substituted for the inactivated enzymes butyrate kinase and phosphotransacetylase. Both strains formed high concentrations of lactic acid, which is not accumulated by wild-type *C. acetobutylicum*, possibly as a response to the accumulation of pyruvate. Inactivation of the aldehyde/alcohol dehydrogenase adhE/aad led to a drastic collapse in the formation of butanol and to a simultaneous increase in the butyrate concentration. The concentrations of butyrate and butanol normal in the wild type are, however, set up again when the adhE/aad gene is expressed on a plasmid in this mutant. It is of interest that formation of acetone could not be detected either in the AdhE/aad mutant or in the strain with the adhE/aad complementation. This phenomenon is based on polar effects which act on two genes localized downstream of adhE/aad. These two genes encode the two subunits of coenzyme A transferase which is essential for the biosynthesis of acetone (Green, E. M, and Bennett, G. N. 1996. Inactivation of an aldehyde/alcohol dehydrogenase gene from *Clostridium acetobutylicum* ATCC 824. Appl. Biochem. Biotechnol. 57/58: 213-221). This is the first described example of the possibility of uncoupling acetone and butyrate formation from one another by pathway engineering in *C. acetobutylicum*.

This observation was confirmed in further publications. The microbial strains investigated in these studies have lost the ability to form acetone and butanol because they lack the 192 kb megaplasmid pSOL1. Most of the genes for the formation of acetone and butanol are located on this plasmid, as are some of those for ethanol synthesis (Cornillot, E., Nair, R., Papoutsakis, E. T., and Soucaille, P. 1997. The genes for butanol and acetone formation in *Clostridium acetobutylicum* ATCC 824 reside on a large plasmid whose loss leads to degeneration of the strain. J. Bacteriol. 179: 5442-5447). These degenerate strains form only half as much ethanol by comparison with the wild-type strains. These strains derived from *C. acetobutylicum ATCC* 824 were called M5 (produced by chemical mutagenesis) and DG1 (obtained by multiple cultivation of the wild type). These served as recipients of plasmids which harboured the protein-encoding sequences of coenzyme A transferase subunits A and B (ctfA and ctfB), and the gene of acetoacetate decarboxylase (adc), or of butyraldehyde/butanol dehydrogenase (adhE/aad). The resulting strains produced either only acetone or butanol (Mermelstein et al. (1993). Metabolic engineering of *Clostridium acetobutylicum* ATCC824 for increased solvent production by enhancement of acetone formation enzyme activities using a synthetic operon. Biotech. Bioeng. 42:1053-1060; Nair, R. V., and Papoutsakis, E. T. 1994. Expression of plasmid-encoded aad in *Clostridium acetobutylicum* M5 restores vigorous butanol production. J. Bacteriol. 176: 5843-5846; Cornillot, E., Nair, R., Papoutsakis, E. T., and Soucaille, P. 1997. The genes for butanol and acetone formation in *Clostridium acetobutylicum* ATCC 824 reside on a large plasmid whose loss leads to degeneration of the strain. J. Bacteriol. 179: 5442-5447). The measured titres for the respective solvents were always below the concentrations of acetone and butanol in the wild type, and acetate and butyrate were able to accumulate up to a total concentration of 240 mM. It was possible to restore ethanol formation to the wild-type level with plasmids harbouring the adhE/aad gene.

Figure 2:
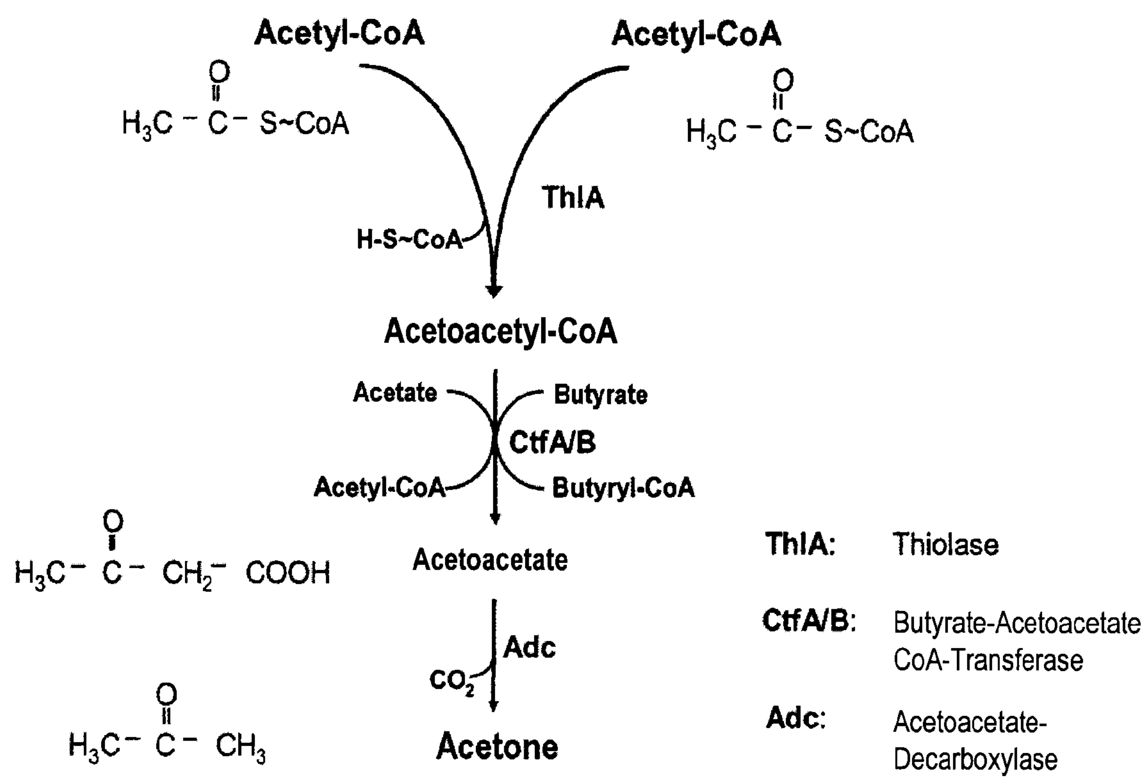

FIG. 2 depicts the classical metabolic pathway characterized in *Clostridium* for acetone synthesis. This pathway starts from acetyl-CoA, a central metabolite which is formed in all microorganisms, irrespective of which C source is metabolized or which metabolic pathways are established. The required enzymes are: β-ketothiolase, the two subunits of acetyl-CoA/butyryl-CoA transferase, and acetoacetate decarboxylase.

It was possible to show that heterologous expression of these enzymes from *C. acetobutylicum* which catalyse acetone formation starting from acetyl-CoA (acetoacetate decarboxylase, acetyl-CoA/butyryl-CoA transferase and thiolase) in *Escherichia coli* lead to formation of about 150 mM acetone in this organism, although large amounts of acetate (50 mM) were also produced in a disadvantageous manner (Bermejo L. L., N. E. Welker, E. T. Papoutsakis. 1998. Expression of *Clostridium acetobutylicum* ATCC 824 Genes in *Escherichia coli* for Acetone Production and Acetate Detoxification. Appl. Env. Microbiol. 64:1079-1085). A further disadvantage in this connection is that acetone was produced only under aerobic conditions, because the redox equivalents produced during metabolism of glucose to acetyl-CoA cannot be reoxidized under anaerobic conditions by *E. coli*. In this process, the CoA eliminated from the acetoacetyl was transferred again to an acceptor molecule by the enzyme catalysing the reaction.

Acyl-CoA-Cleaving Enzymes

Enzymes which hydrolyse acyl-CoA may be for example acyl-CoA thioesterases or acyl-CoA thiokinase. The main difference between hydrolysis of acyl-CoA by an acyl-CoA thioesterase or an acyl-CoA synthetase/acyl-CoA thiokinase is the formation of ATP or GTP in the case of kinases, because hydrolysis of acetoacetyl-CoA has a higher $\Delta G_0'$ value of −44 kJ compared with the hydrolysis of ATP (−31.8 kJ).

Acetoacetyl-CoA Hydrolase (EC 3.1.2.11)

This enzyme catalyses the hydrolysis of acetoacetyl-CoA to acetoacetate and coenzyme A without at the same time transferring the CoA molecule to an acceptor molecule such as, for example, a carboxylic acid.

Acyl-CoA Thioesterases (EC 3.1.2.18)

The protein YbgC from *Haemophilus influenzae* is an acyl-CoA thioesterase (EC 3.1.2.18) specific for short-chain molecules and accepts butyryl-CoA and β-hydroxybutyrate-CoA as substrates. The Km values are respectively 24 mM and 20 mM for these substrates (Zhuang et al. (2002). The YbgC protein encoded by the ybgC gene of the tol-pal gene cluster of *Haemophilus influenzae* catalyzes acyl-coenzyme A thioester hydrolysis. FEBS Lett. 516:161-3).

A thioesterase II ($TEII_{srf}$) with amino acid sequence SEQ ID No. 1 and corresponding cDNA sequence SEQ ID No. 2 is also described in *Bacillus subtilis* and is associated with the non-ribosomal peptide synthetases for formation of the peptide antibiotic surfactin (Schwarzer D., H. D. Mootz, U. Linne, M. A. Marahiel. 2002. Regeneration of misprimed nonribosomal peptide synthetases by type II thioesterases. PNAS 99:14083-14088).

Acyl-CoA Synthetases/acyl-CoA Thiokinases (with AMP Formation; EC 6.2.1.2, with GDP Formation; EC 6.2.1.10))

The physiological function of these two enzymes mentioned is in the acyl-CoA synthesis, but examples in which these enzymes catalyse the reverse, hydrolytic reaction to form ATP are also known, such as, for example, succinyl-CoA thiokinase in the tricarboxylic acid cycle. It has not to date been demonstrated, either in vitro or in vivo, that the abovementioned enzyme classes are able to hydrolyse acetoacetyl-CoA with formation of acetoacetate and free coenzyme A.

Degradation of polyhydroxyalkanes by an acyl-CoA synthetase with AMP formation is described for AcsA2 from *Sinorhizobium meliloti* (Aneja et al. (2002). Identification of an acetoacetyl coenzyme A synthetase-dependent pathway for utilization of L-(+)-3-hydroxybutyrate in *Sinorhizobium meliloti*. J. Bacteriol. 184:1571-7).

With a further purified enzyme from *Pseudomonas aeruginosa* it was possible to detect an acyl-CoA synthetase/acyl-CoA thiokinase (with AMP formation; EC 6.2.1.2) specific for short-chain molecules. This enzyme accepts both butyryl-CoA and β-hydroxybutyryl-CoA and 2-ketobutyrate as substrate, with very low Km values of respectively 10, 25 and 25 μM (Shimizu et al. (1981). Butyryl-CoA synthetase of *Pseudomonas aeruginosa*-purification and characterization. Biochem. Biophys. Res. Commun. 103:1231-7).

It was therefore an object of the present invention to provide a novel, simplified metabolic pathway for acetone synthesis starting from acetyl-CoA.

DESCRIPTION OF THE INVENTION

The invention described herein is concerned with the improved production of acetone with the aid of recombinant enzyme techniques: starting from acetyl-CoA, acetoacetate is generated via acetoacetyl-CoA and is subsequently converted into acetone and $CO_2$.

The present invention therefore relates to a process for producing acetone as described in claim 1, to the use of the enzymes as described herein which make process step B of the process of the invention possible, and nucleic acid sequences as described herein, and to the use of nucleic acid sequences whose translation products are able to catalyse the process of the invention as described herein.

The process of the invention has the advantage that the butyrate-acetoacetate-CoA transferase which, in conventional systems, converts acetoacetyl-CoA into acetoacetate and consists of two subunits is now replaced by one enzyme which is able to exert its activity as monomer.

The process of the invention thereby has the further advantage that the yields of acetone in the given system are higher than with known butyrate-acetoacetate-CoA transferase. A further advantage is that the ratio of acetate to acetone is shifted in favour of acetone during the production process.

Yet a further advantage of the process of the invention is the fact that acetone synthesis is uncoupled from that of butanol and ethanol, and thus the resulting alcoholic byproducts do not poison microbial producers when used. This leads to higher product concentrations in the medium and thus improved space-time yields.

A further advantage of the preparation of acetone uncoupled from butanol and ethanol is a simplified fermentation protocol, and the simpler isolation and working up of the product, because it is no longer necessary to separate it from the alcoholic byproducts. This then also leads to a smaller energy requirement compared with product separation in conventional ABE fermentation. A further advantage of the process of the invention is that it can be carried out in various microorganisms which are particularly well characterized, can be cultivated extremely well both aerobically and anaerobically and are known for the most diverse possibilities of genetic manipulation and thus further possibilities of improvement. Overall, the efficient preparation of acetone by fermentation from renewable raw materials represents a further contribution to environmentally compatible and resource-sparing production of an industrial chemical.

The process of the invention for preparing acetone and the use of indicated polypeptides and nucleic acids for carrying out the process of the invention are described by way of example below without intending to restrict the invention to these exemplary embodiments. Citation of documents in the context of the present description is intended to include their contents in their entirety in the disclosure of the present invention. Polypeptides mean those of any chain length. Thus, they also include any proteins, enzymes and, in particular, acetoacetate-CoA hydrolases, acyl-CoA thioesterases, Acyl-CoA synthetases or acyl-CoA thiokinases. A "spontaneous conversion" means an exergonic chemical reaction. Hybridization "under stringent conditions" means those experimental conditions like, for example, in the Northern blot technique the use of a washing solution at 50-70° C., preferably 60-65° C., employing, for example, 0.1×SSC buffer with 0.1% SDS (20×SSC: 3M NaCl, 0.3M Na citrate, pH 7.0) for eluting nonspecifically hybridized cDNA probes or oligonucleotides. In this case, only nucleic acids which are highly complementary remain bound to one another. The setting up of stringent conditions is known to the skilled person and is described for example in Ausubel et al., *Current Protocols in Molecular Biology*, John Wiley & Sons, N.Y. (1989), 6.3.1-6.3.6.

The present invention includes a process for preparing acetone starting from acetyl-coenzyme A including the steps: A. enzymatic conversion of acetyl-CoA into acetoacetyl-CoA B. enzymatic conversion of acetoacetyl-CoA into acetoacetate and CoA and C. decarboxylation of acetoacetate to acetone and $CO_2$, characterized in that the coenzyme A is not transferred in process step B to an acceptor molecule.

It is possible to employ in process step A in the process of the invention a β-ketothiolase for enzymatic conversion of acetyl-CoA into acetoacetyl-CoA. A β-ketothiolase from *Clostridium* spec., i.e. a microorganism of the genus *Clostridium*, particularly preferably from *Clostridium acetobutylicum* or *Clostridium beijerinckii*, is preferably employed. The enzymatic conversion in process step A is preferably catalysed by a polypeptide having a ketothiolase activity and having an amino acid sequence which is at least 90%, preferably at least 95%, more preferably 96, 97, 98, 99 or 100% identical to the amino acid sequence of SEQ ID No. 16.

In process step C in the process of the invention it is possible to employ an acetoacetate decarboxylase for converting acetoacetyl-CoA into acetone and $CO_2$. An acetoacetate decarboxylase from *Clostridium* spec., i.e. a microorganism of the genus *Clostridium*, is preferably employed, particularly preferably from *Clostridium acetobutylicum* or *Clostridium beijerinckii*. The enzymatic conversion in process step C is preferably catalysed by a polypeptide having an acetoacetate decarboxylase activity and having an amino acid sequence which is at least 90%, preferably at least 95%, more preferably 96%, 97%, 98%, 99% or 100% identical to the amino acid sequence of SEQ ID No. 18. A further embodiment of the process of the invention is characterized in that the conversion in process step C takes place spontaneously.

The process of the invention for acetone production is distinguished by the coenzyme A not being transferred in process step B to an acceptor molecule. This can be achieved by employing enzymes having acetoacetate-CoA hydrolase activity. It is surprisingly likewise possible to achieve this object with enzymes to which this activity has not hitherto been ascribed, such as, for example, those selected from the group of acyl-CoA thioesterases, an acyl-CoA synthetases or acyl-CoA thiokinases. Preferred embodiments of the process of the invention are therefore those in which the enzymatic conversion in process step B is catalysed by an acetoacetate-CoA hydrolase, an acyl-CoA thioesterase, an acyl-CoA synthetase or an acyl-CoA thiokinase.

In a preferred embodiment of the process of the invention, the enzymatic conversion in process step B can be catalysed by a polypeptide having acetoacetate-CoA hydrolase activity and having an amino acid sequence which is at least 90%, preferably at least 95%, more preferably 96%, 97%, 98%, 99% or 100% identical to the amino acid sequence of SEQ ID No. 1. In a further preferred embodiment of the process of the invention, the enzymatic conversion in process step B can be catalysed by a polypeptide having acetoacetate-CoA hydrolase activity and having an amino acid sequence which is at least 90%, preferably at least 95%, more preferably 96%, 97%, 98%, 99% or 100% identical to the amino acid sequence of SEQ ID No. 3. In a particularly preferred embodiment of the process of the invention, the enzymatic conversion in process step B can be catalysed by a polypeptide having acetoacetate-CoA hydrolase activity and having an amino acid sequence which is at least 90%, preferably at least 95%, more preferably 96%, 97%, 98%, 99% or 100% identical to the amino acid sequence of SEQ ID No. 5.

The process is preferably carried out by microorganisms. The microorganisms used for the process may in this connection intrinsically have the ability to synthesize acetone or may have been made capable of acetone formation only through the genetic pathway engineering. This can be achieved by increasing the cellular concentration or the activity of enzymes which catalyse an acetate-independent acetone synthesis starting from acetyl-CoA.

The process of the invention is preferably carried out in genetically modified microorganisms. Possible examples are derived from a genus selected from the group of *Clostridium, Zymomonas, Escherichia, Salmonella, Rhodococcus, Pseudomonas, Bacillus, Lactobacillus, Enterococcus, Alcaligenes, Klebsiella, Paenibacillus, Arthrobacter, Corynebacterium, Brevibacterium, Pichia, Candida, Hansenula* and *Saccharomyces*. Examples of species of these genera are *Escherichia coli, Alcaligenes eutrophus, Bacillus licheniformis, Paenibacillus macerans, Rhodococcus erythropolis, Pseudomonas putida, Enterococcus faecium, Enterococcus gallinarium, Enterococcus faecalis, Bacillus subtilis* and *Saccharomyces cerevisiae.*

An organism selected from the group of *Escherichia coli, Corynebacterium glutamicum, Clostridium* spec., *Clostridium aceticum, Acetobacterium woodii, Clostridium acetobutylicum, Clostridium beijerinckii, Yarrowia lipolytica, Saccharomyces* spec., *Saccharomyces cerevisiae* and *Pichia pastoris*, particularly preferably "*E. coli* pUC19ayt", cf. Examples 5 and 6, is preferably employed in the process of the invention.

Recombinant microorganisms can be produced by the recombinant genetic engineering processes known to the skilled person. In general, the vectors harbouring the foreign genes can be inserted into the cells by conventional transformation or transfection techniques. Suitable methods can be found in Sambrook et al. (Molecular Cloning: A Laboratory Manual. 2nd ed., Cold Spring Harbor Laboratory, 1989). The microorganisms used may be strains produced by mutagenesis and selection, by recombinant DNA techniques or by a combination of the two methods. Classical in vivo mutagenesis processes using mutagenic substances such as, for example, N-methyl-N'-nitro-N-nitrosoguanidine or ultraviolet light can be used for the mutagenesis. It is also possible to use for the mutagenesis in vitro methods such as, for example, a treatment with hydroxylamine (Miller, J. H.: A Short Course in Bacterial Genetics. A Laboratory Manual and Handbook for *Escherichia coli* and Related Bacteria, Cold Spring Harbor Laboratory Press, Cold Spring Harbor, 1992) or mutagenic oligonucleotides (T. A. Brown: Gentechnologie für Einsteiger, Spektrum Akademischer Verlag, Heidelberg, 1993) or the polymerase chain reaction (PCR) as described in the handbook by Newton and Graham (PCR, Spektrum Akademischer Verlag, Heidelberg, 1994).

Further instructions for the generation of mutations can be found in the prior art and well-known textbooks of genetics and molecular biology such as, for example, the textbook by Knippers ("Molekulare Genetik", 6th edition, Georg Thieme Verlag, Stuttgart, Germany, 1995), that by Winnacker ("Gene and Klone", VCH Verlagsgesellschaft, Weinheim, Germany, 1990) or that by Hagemann ("Allgemeine Genetik", Gustav Fischer Verlag, Stuttgart, 1986).

On use of in vitro methods, the gene described in the prior art is amplified, starting from isolated total DNA of a wild-type strain with the aid of the polymerase chain reaction, and is cloned where appropriate into suitable plasmid vectors, and the DNA is subsequently subjected to the mutagenesis process. Instructions for amplifying DNA sequences with the aid of the polymerase chain reaction (PCR) are to be found by the skilled person inter alia in the handbook by Gait: Oligonucleotide Synthesis: A Practical Approach (IRL Press, Oxford, UK, 1984) and in Newton and Graham: PCR (Spektrum Akademischer Verlag, Heidelberg, Germany, 1994). In the same way, methods of in vitro mutagenesis can also be used, like those described for example in the well-known handbook by Sambrook et al. (Molecular Cloning, A Laboratory Manual, 2nd ed., Cold Spring Harbor Laboratory Press, Cold Spring Harbor, N.Y., USA, 1989). Corresponding methods are also commercially available in the form of so-called kits, such as, for example, the "QuikChange Site-Directed Mutagenesis Kit" described by Papworth et al. (Strategies 9(3), 3-4 (1996)) and supplied by Stratagene (La Jolla, USA).

The invention also relates to vectors, in particular plasmids, which contain the polynucleotides employed according to the invention and replicate where appropriate in the bacteria. The invention likewise relates to the recombinant microorganisms which have been transformed with the said vectors. The polynucleotides may in this connection be subject to the action of a single or a plurality of promoters. The term "enhancement" describes in this connection the increase in the intracellular activity or concentration of one or more enzymes or proteins in a microorganism which are encoded by the corresponding DNA by, for example, increasing the copy number of the gene or genes, of the ORF or of the ORFs by at least one (1) copy, functionally linking a strong promoter to the gene, or using a gene or allele or ORF which codes for a corresponding enzyme or protein having a high activity and, where appropriate, combining these measures. Examples of strong promoters in *E. coli* which are mentioned are lac, tac and trp. The open reading frame (ORF) refers to a segment of a nucleotide sequence which codes or may code for a protein or polypeptide or ribonucleic acid to each of which no function can be assigned according to the prior art. After a function has been assigned to the relevant segment of the nucleotide sequence, reference is generally made to a gene. Alleles mean in general alternative forms of a given gene. The forms are distinguished by differences in the nucleotide sequence.

Gene product refers in general to the protein encoded by a nucleotide sequence, i.e. an ORF, a gene or an allele, or the encoded ribonucleic acid. The activity or concentration of the corresponding protein is generally increased through the measures of enhancement, in particular overexpression, by at least 10%, 25%, 50%, 75%, 100%, 150%, 200%, 300%, 400% or 500%, maximally up to 1000% or 2000%, based on that of the wild-type protein or on the activity or concentration of the protein in the microorganism which is not recombinant for the corresponding enzyme or protein, or the parent strain. The non-recombinant microorganism or parent strain means the microorganism on which the enhancement or overexpression according to the invention is carried out. The genes or gene constructs may be present either in plasmids with different copy numbers or be integrated and amplified in the chromosome. It is further possible as an alternative to achieve overexpression of the relevant genes by altering the composition of media and management of the culturing.

The invention relates to a process in which genetically modified microorganisms express nucleic acids which protein-code for enzymes as described above which are able to carry out process steps A to C.

The process of the invention is characterized in that the microorganism contains at least one nucleic acid a, protein-coding for at least one polypeptide having a ketothiolase activity and having an amino acid sequence which is at least 90%, preferably at least 95%, more preferably 96%, 97%, 98%, 99% or 100% identical to the amino acid sequence of SEQ ID No. 16, one nucleic acid b, protein-coding for at least one polypeptide which is an acetoacetate-CoA hydrolase, acyl-CoA thioesterase, an acyl-CoA synthetase or acyl-CoA thiokinase, or having acetoacetate-CoA hydrolase activity and having an amino acid sequence which is at least 90%, preferably at least 95%, more preferably 96%, 97%, 98%, 99% or 100% identical to the amino sequence of SEQ ID No. 1, or having acetoacetate-CoA hydrolase activity and having an amino acid sequence which is at least 90%, preferably at least 95%, more preferably 96%, 97%, 98%, 99% or 100% identical to the amino acid sequence of SEQ ID No. 3, or having acetoacetate-CoA hydrolase activity and having an amino acid sequence which is at least 90%, preferably at least 95%, more preferably 96%, 97%, 98%, 99% or 100% identical to the amino acid sequence of SEQ ID No. 5, and one nucleic acid sequence c protein-coding for at least one polypeptide having an acetoacetatedecarboxylase activity and having an amino acid sequence which is at least 90%, preferably at least 95%, more preferably 96%, 97%, 98%, 99% or 100% identical to the amino acid sequence of SEQ ID No. 18, the nucleic acids a, b and c being used to ensure expression of the polypeptide in the microorganism.

Preferably employed in this connection is a nucleic acid a which is selected from:

aa DNA sequence described by sequence 17 or its complementary strand, bb DNA sequences which hybridize under stringent conditions to the DNA sequences described under aa, cc DNA sequences which would, without the degeneracy of the genetic code, hybridize to the DNA sequences defined in aa and bb.

A nucleic acid c which is preferably employed is one selected from:

dd DNA sequence described by sequence 19 or its complementary strand, ee DNA sequences which hybridize under stringent conditions to the DNA sequences described under dd, ff DNA sequences which, without the degeneracy of the genetic code, would hybridize to the DNA sequences described under dd and ee, A nucleic acid b which is preferably employed is one selected from:

gg DNA sequence described by sequence 2 or its complementary strand, hh DNA sequences which hybridize under stringent conditions to the DNA sequences described under gg, ii DNA sequences which, without the degeneracy of the genetic code, would hybridize to the DNA sequences described under gg and hh, or more preferably from:

jj DNA sequence described by sequence 4 or its complementary strand, kk DNA sequences which hybridize under stringent conditions to the DNA sequences described under jj, ll DNA sequences which, without the degeneracy of the genetic code, would hybridize to the DNA sequences described under jj and kk, or particularly preferably from:

mm DNA sequence described by sequence 6 or its complementary strand, nn DNA sequences which hybridize under stringent conditions to the DNA sequences described under mm, oo DNA sequences which, without the degeneracy of the genetic code, would hybridize to the DNA sequences described under mm and nn.

In preferred embodiments of the process of the invention, the nucleic acids a, b and c are located on a nucleotide strand which makes expression of all three gene products possible.

The nucleic acids a, b and c are particularly preferably located on one nucleotide strand, and the latter is selected from the group comprising:

plasmid pSKatt having the nucleic acid sequence shown in SEQ ID No. 7, plasmid pKSatt having the nucleic acid sequence shown in SEQ ID No. 8, plasmid pUC19att having the nucleic acid sequence shown in SEQ ID No. 9, plasmid pUC18att having the nucleic acid sequence shown in SEQ ID No. 10 and plasmid pUC19ayt having the nucleic acid sequence shown in SEQ ID No. 11.

The invention thus also relates to the nucleic acids plasmid pSKatt having the nucleic acid sequence shown in SEQ ID No. 7, plasmid pKSatt having the nucleic acid sequence shown in SEQ ID No. 8, plasmid pUC19att having the nucleic acid sequence shown in SEQ ID No. 9, plasmid pUC18att having the nucleic acid sequence shown in SEQ ID No. 10 and plasmid pUC19ayt having the nucleic acid sequence shown in SEQ ID No. 11.

The invention further relates to the use of acyl-CoA thioesterases, acyl-CoA synthetases or acyl-CoA thiokinases for the enzymatic conversion of acetoacetyl-CoA into acetoacetate and coenzyme A. Because of the high substrate specificity of most enzymes it is surprising and could not have been predicted by the skilled person that enzymes of these classes accept acetoacetate-CoA as substrate.

Preference is given to the use of a polypeptide having acyl-CoA thioesterase, acyl-CoA synthetase or acyl-CoA thiokinase activity for the enzymatic conversion of acetoacetyl-CoA into acetoacetate and CoA, the polypeptide being an acetoacetate-CoA hydrolase, acyl-CoA thioesterase, an acyl-CoA synthetase or acyl-CoA thiokinase, or having an amino acid sequence which is at least 90%, preferably at least 95%, more preferably 96%, 97%, 98%, 99% or 100% identical to the amino acid sequence of SEQ ID No. 1, or having an amino acid sequence which is at least 90%, preferably at least 95%, more preferably 96%, 97%, 98%, 99% or 100% identical to the amino acid sequence of SEQ ID No. 3, or having an amino acid sequence which is at least 90%, preferably at least 95%, more preferably 96%, 97%, 98%, 99% or 100% identical to the amino acid sequence of SEQ ID No. 5.

The invention thus also relates to the use of at least one of the nucleic acids b selected from the groups gg to oo for utilization of the gene product thereof for converting acetoacetyl-CoA into acetoacetate and CoA.

The present invention is described by way of example in the examples detailed below without intending to restrict the invention, whose range of use emerges from the entire description and the claims, to the embodiments mentioned in the examples.

FIG. 1: Biosynthesis of acetone, butanol and ethanol

FIG. 2: Biosynthesis of acetone

Figure 3:
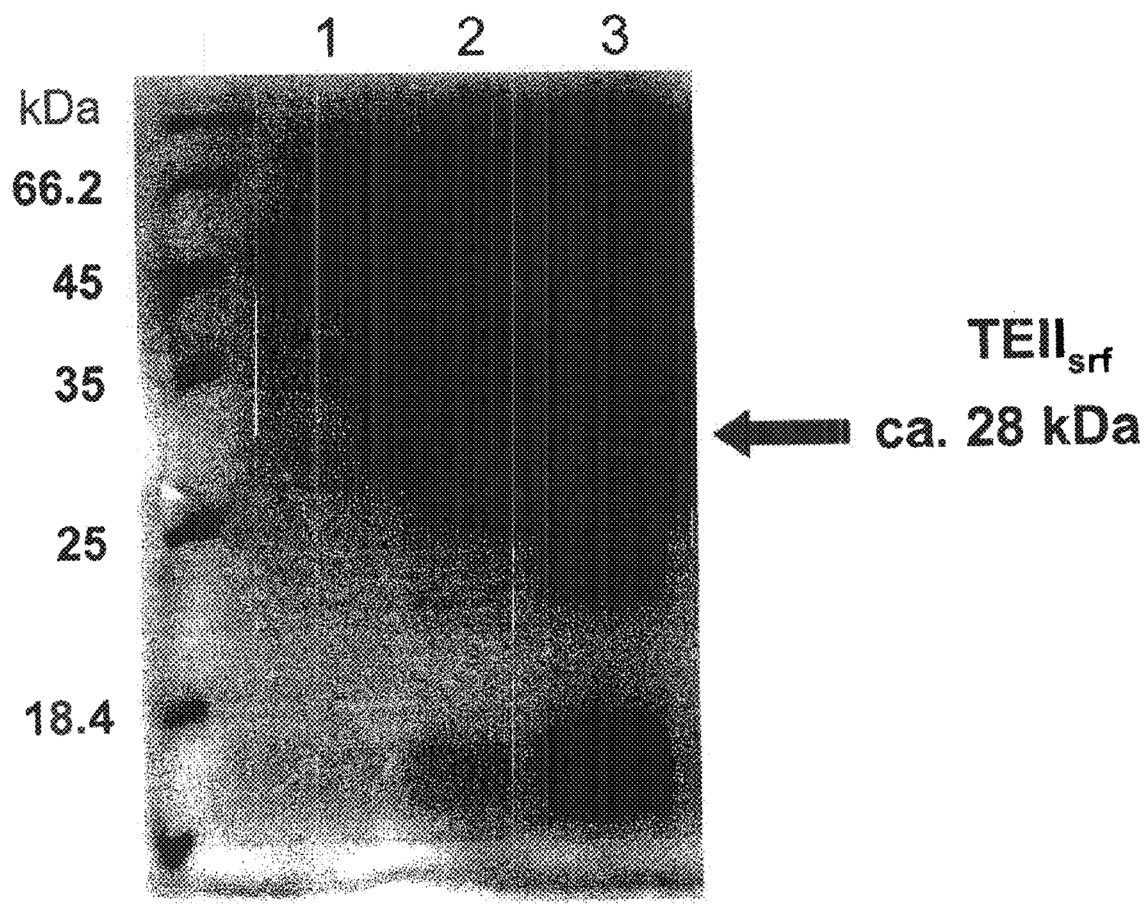

FIG. 3: Expression of $TEII_{srf}$ in *E. coli*. M15

Figure 4:
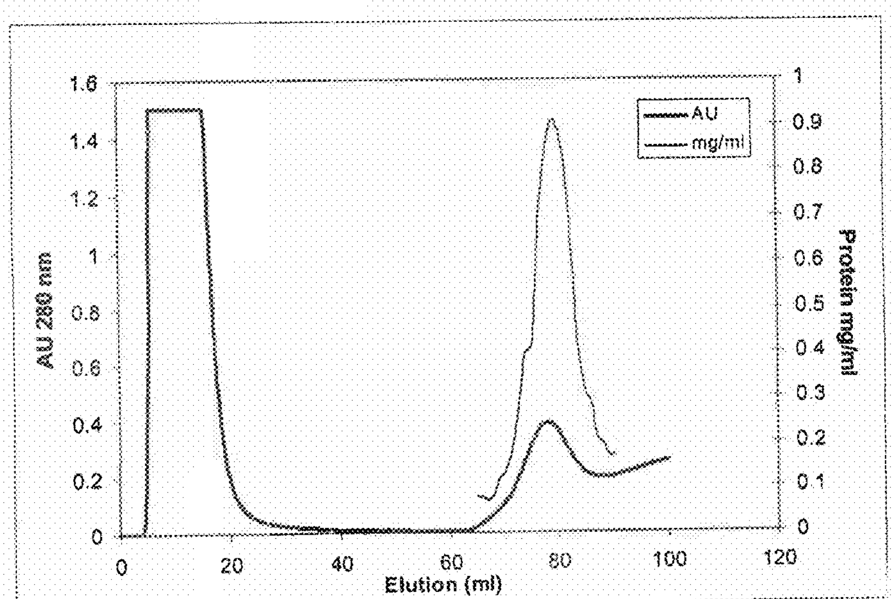
Figure 4:
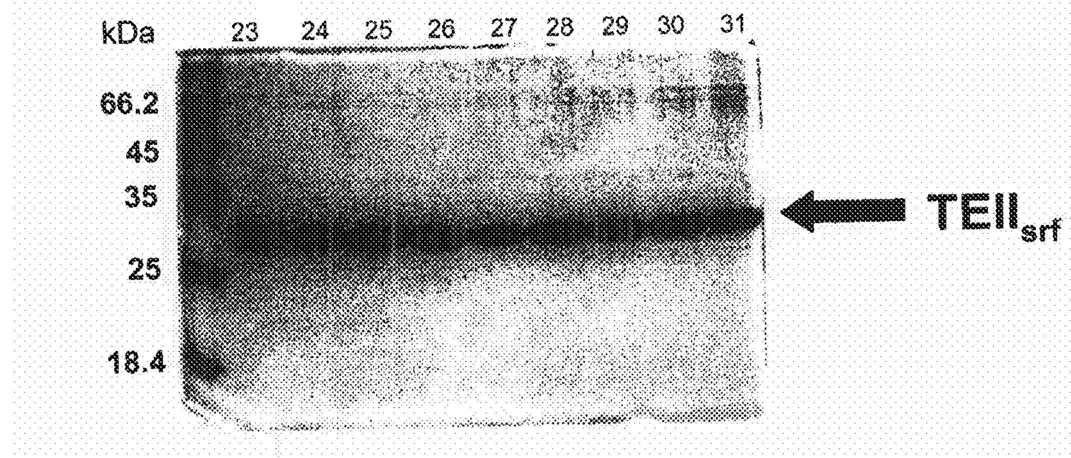

FIG. 4: Purification of $TEII_{srf}$ from *E. coli*

Figure 5:
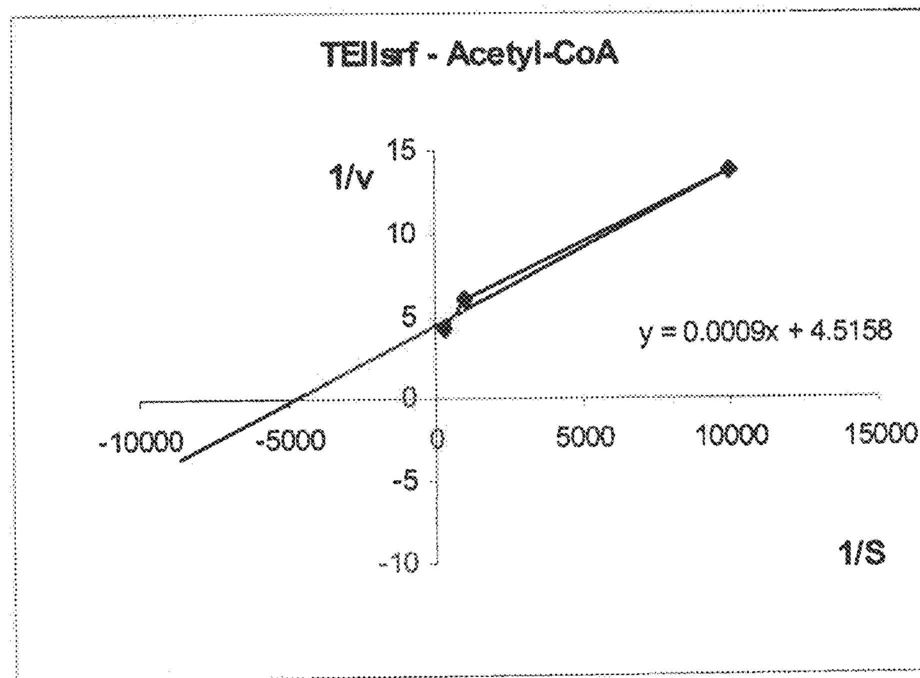
Figure 5:
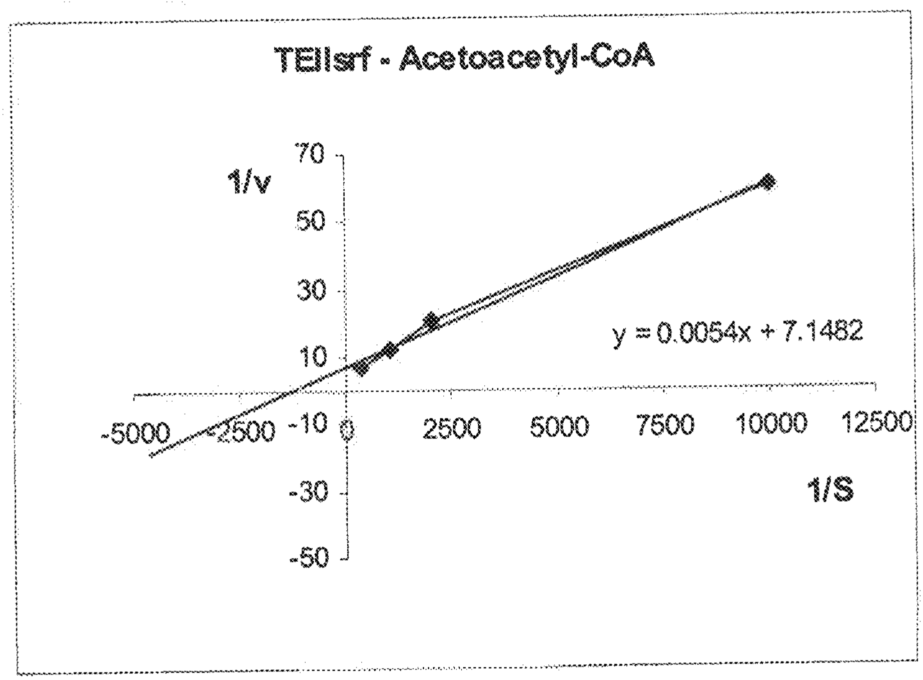

FIG. 5: Lineweaver-Burk diagrams to ascertain the Km values of $TEII_{srf}$ for the substrates acetyl-CoA and acetoacetyl-CoA FIG. 6: Expression of AACS in *E. coli* BL21 (DE3)

Figure 7:
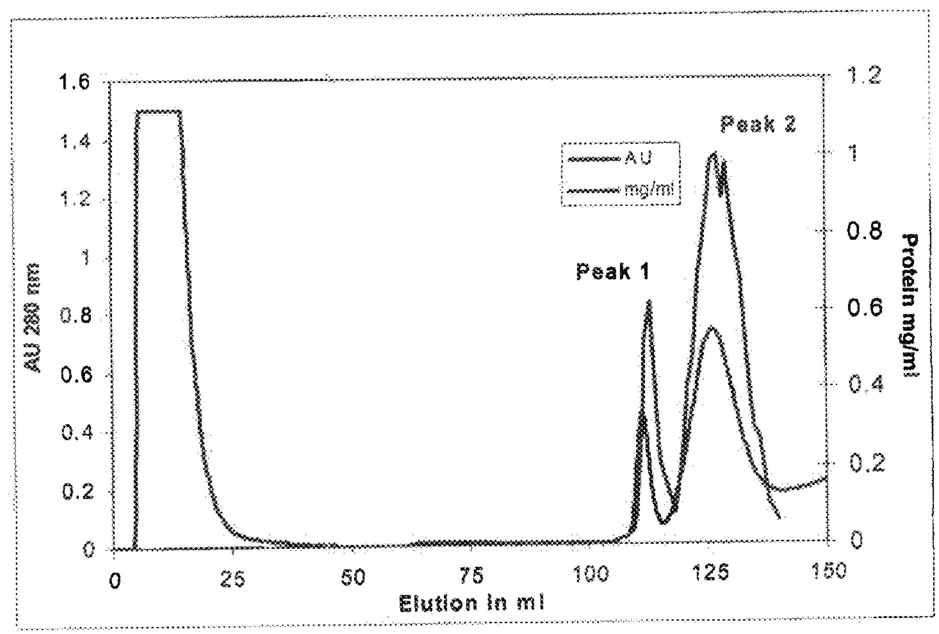
Figure 7:
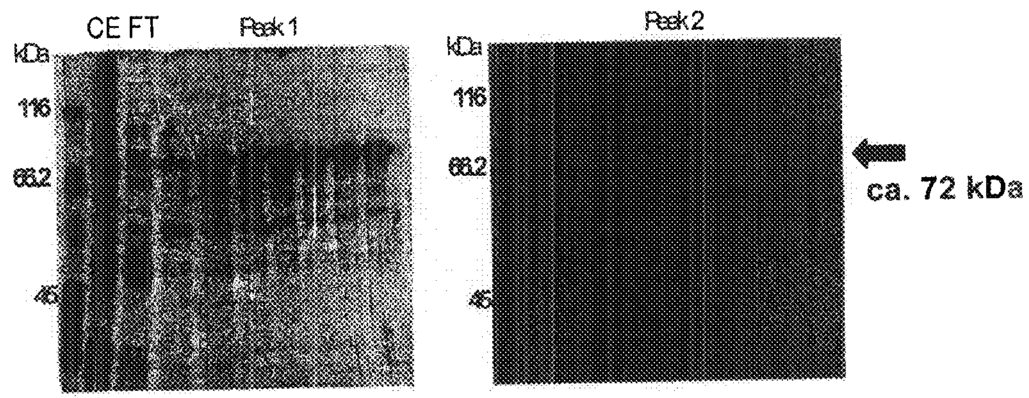

FIG. 7: Purification of AACS from *E. coli*

Figure 8:
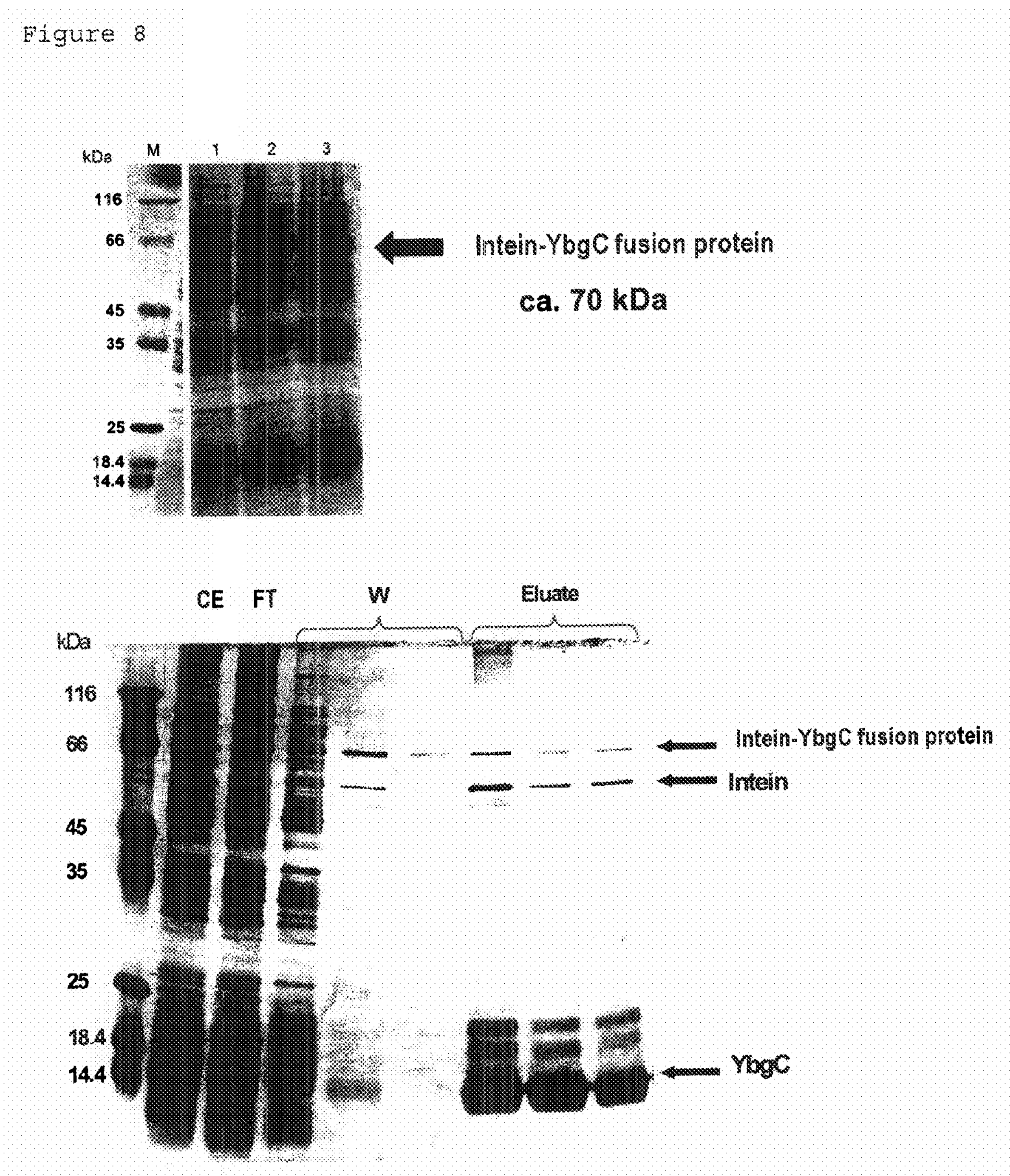

FIG. 8: Expression and purification of YbgC

Figure 9:
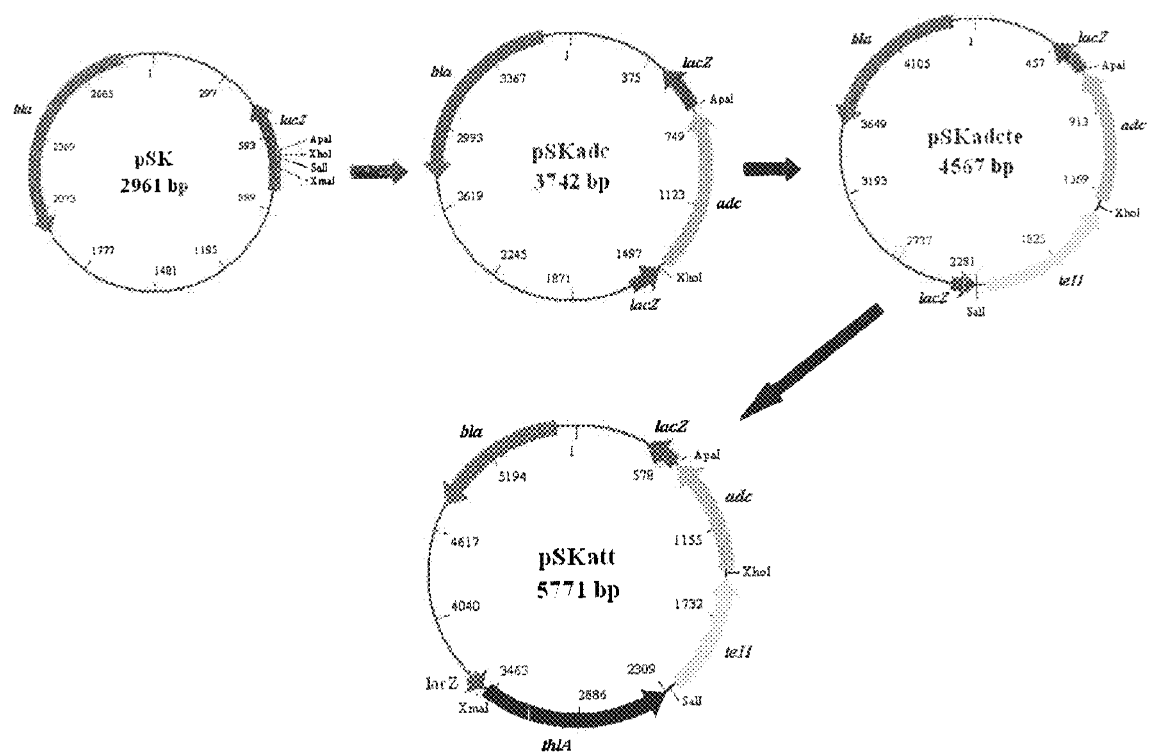

FIG. 9: Schematic representation of the successive cloning of the genes adc, teIIsrf and thlA into the plasmid pSK.

Figure 10:
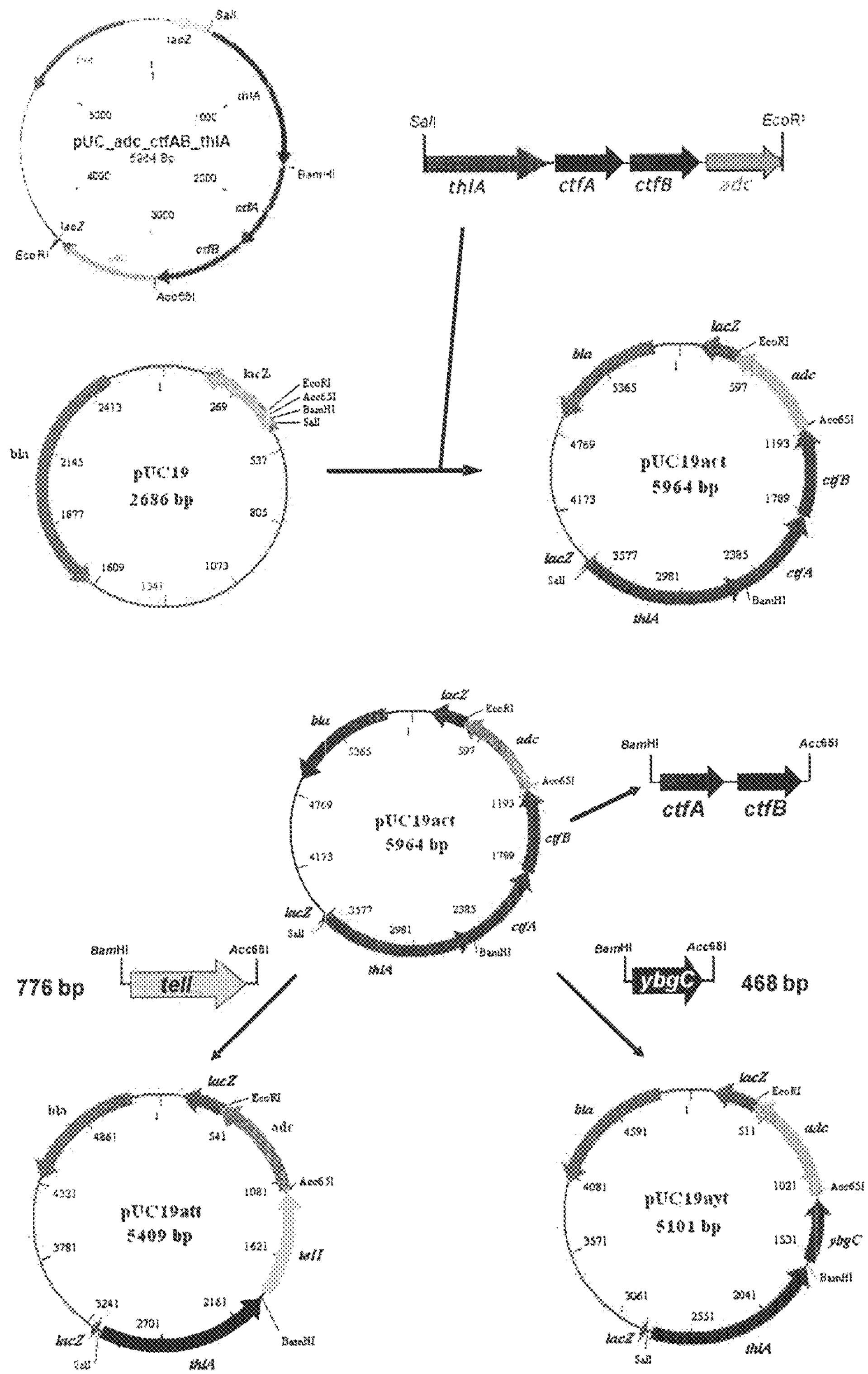

FIG. 10: Generation of pUC19 constructs

Figure 11:
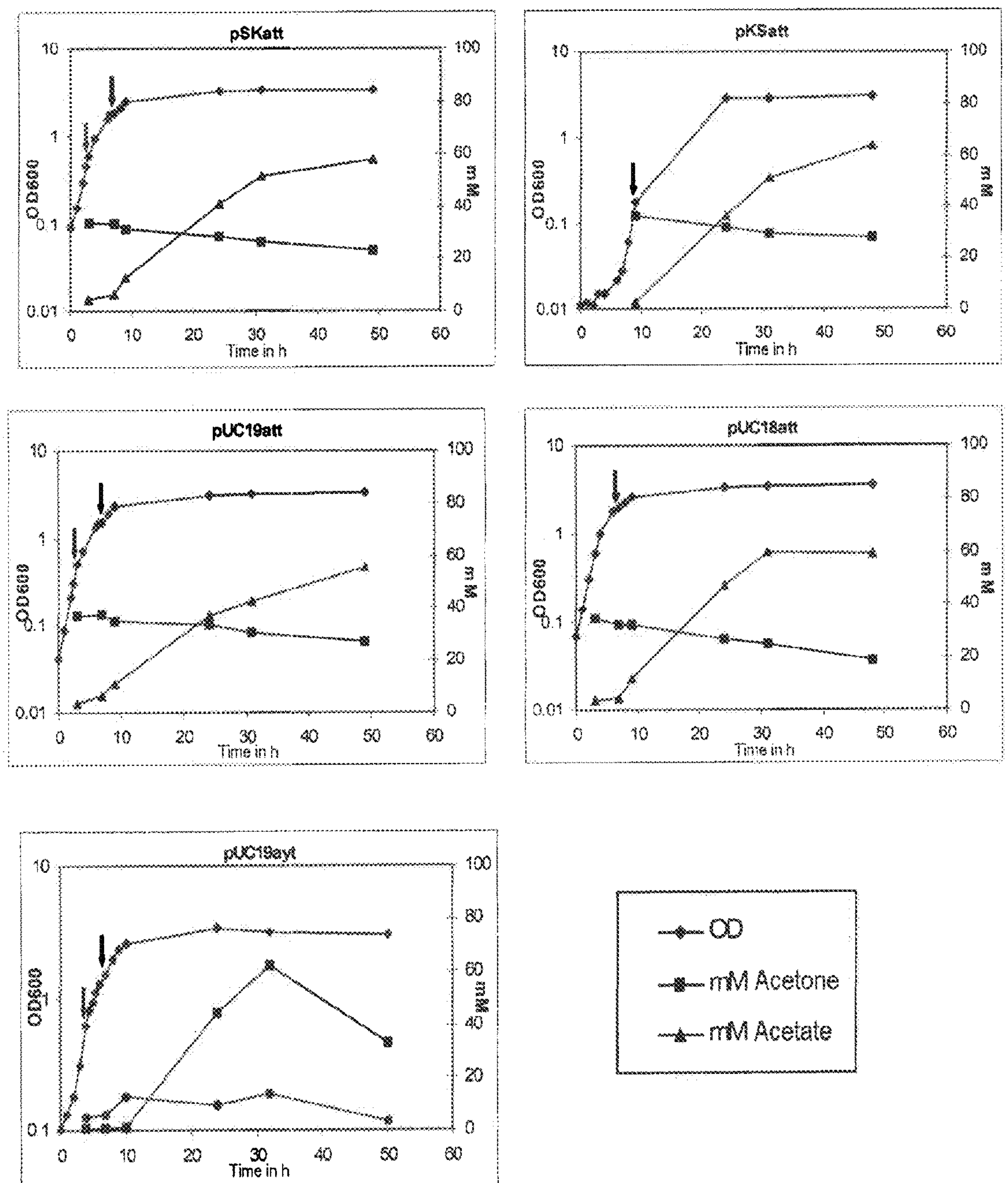

FIG. 11: Acetone and acetate formation in 5 ml cultures of various expression vectors in *E. coli* HB101

Figure 12:
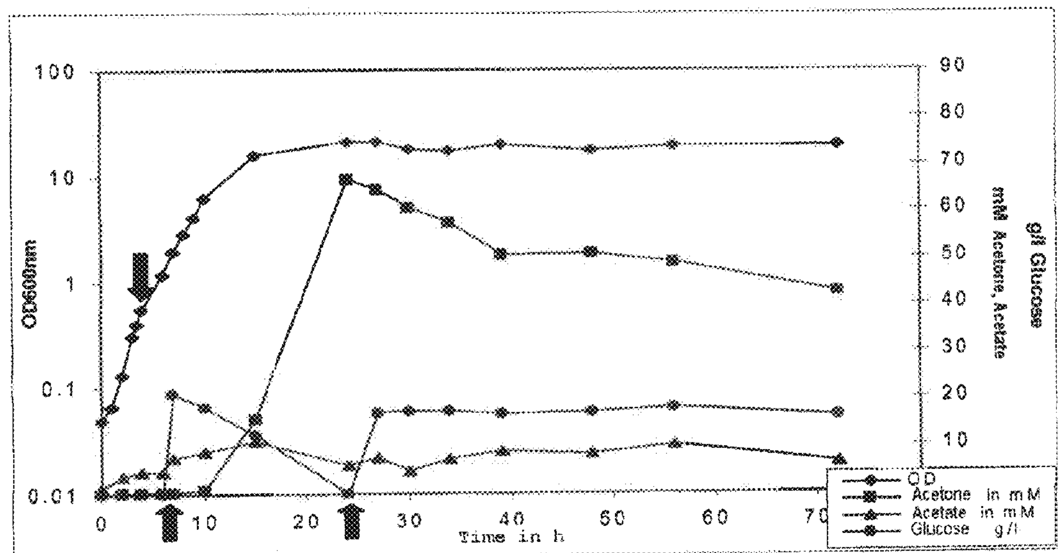
Figure 12:
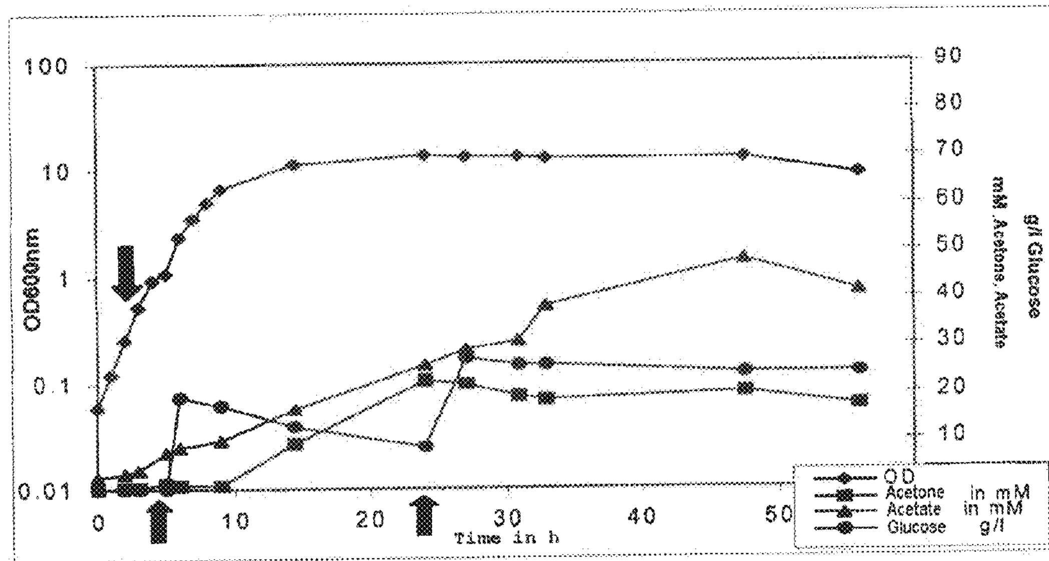

FIG. 12: Acetone and acetate formation in 100 ml cultures of *E. coli* HB101 with pUC19ayt (YbgC) and pUC19act (control CtfA/B)

EXAMPLES

Example 1

Thioesterase II ($TEII_{srf}$) from *Bacillus subtilis*

This enzyme is associated with the non-ribosomal peptide synthetases for the formation of surfactin (peptide antibiotics) in *B. subtilis* ATCC 21332. Schwarzer et al. were able to clone the corresponding gene into the plasmid pQE60 which mediates fusion of the target protein with a C-terminal His tag (pTEIIsrf) and purify the protein (28 kDa) (Schwarzer D., H. D. Mootz, U. Linne, M. A. Marahiel. 2002. Regeneration of misprimed nonribosomal peptide synthetases by type II thioesterases. PNAS 99:14083-14088). In subsequent investigations, a hydrolytic activity with acetyl-CoA and propionyl-CoA as substrates was demonstrated for this protein.

The plasmid pTEIIsrf with SEQ ID No. 13 was prepared as described in Schwarzer D, Mootz H D, Linne U, Marahiel M A. Regeneration of misprimed nonribosomal peptide synthetases by type II thioesterases. Proc Natl Acad Sci USA. 2002 Oct. 29; 99 (22):14083-8.

The expression of the protein took place in *E. coli* M15 in $LB_{Amp}$ medium at 30° C. and 150 rpm and was induced at an optical density ($OD_{600nm}$) of 0.6-0.8 with 1 mM IPTG. The culture was harvested after a further 2 h hours. Samples taken during growth confirmed successful protein expression. FIG. 3 shows a 12% SDS-polyacrylamide gel after Coomassie staining, to which 15 μl of crude extract were applied per lane; 1: before induction, 2: 1 h after induction, 3: 2 h after induction The intended activity measurement using the DTNB assay [5,5'-dithiobis(2-nitrobenzoic acid)], with which free SH groups are determined, required purification of the protein. This took place with the assistance of FPLC via the fused His tag of $TEII_{srf}$ by means of metal chelate affinity chromatography on $Ni^{2+}$-NTA agarose and increasing imidazole gradient.

For this purpose, initially the cells were harvested (5000×g, 15 min, 4° C.), suspended in 3 ml/g fresh weight of cell disruption buffer (50 mM HEPES, 300 mM NaCl, pH 7.8) and stored if necessary at −20° C. The cells were disrupted by ultrasound treatment (Sonicator Bandelin Sonopuls, Bandelin Berlin), and the crude extract was obtained by centrifugation (30 000×g, 30 min, 4° C.). Purification took place on an FPLC system (Pharmacia Biotech GmbH). 3.5 ml of crude extract were loaded onto the $Ni^{2+}$-NTA agarose column (Qiagen Superflow, bed volume 5 ml) which had been prepared and equilibrated (50 mM HEPES, 300 mM NaCl, 30 mM imidazole, pH 7) in accordance with the manufacturer's instructions. The column was then washed with 50 ml of equilibration buffer. Elution took place with a linear imidazole gradient over 50 ml (30-300 mM imidazole in 50 mM HEPES, 300 ml of NaCl, pH 7).

FIG. 4 shows in the upper portion the FPLC elution profile on $Ni^{2+}$-NTA agarose (Qiagen Superflow, bed volume 5 ml) with a programme with: washing 0-50 ml, elution 50-100 ml with 30-300 mM imidazole (linear gradient) and fraction sizes each of 1 ml; the lower portion depicts a Coomassie-stained 12% SDS-PAGE gel on which elution fractions 23-31, in each case 1 μg of protein/lane, are loaded.

The resulting fractions were combined and employed for the activity determination. The substrates used were acetoacetyl-CoA and, for comparison, acetyl-CoA. In the DTNB assay, the terminal sulfhydryl group of CoA, which has been liberated by the enzymatic conversion to acetoacetate or acetate, reacts with DTNB to give a coloured product which can be determined by photometry at 412 nm.

The following kM values were determined: this was $2\times10^{-4}$ $mol\cdot l^{-1}$ (0.2 mM) for acetyl-CoA, and was $7.7\times10^{-4}$ $mol\cdot l^{-1}$ (0.77 mM) for acetoacetyl-CoA. $TEII_{srf}$ thus shows a higher substrate affinity for acetyl-CoA. FIG. 5 shows the Lineweaver-Burk diagram to ascertain the Km values of $TEII_{srf}$ for the substrates acetyl-CoA and acetoacetyl-CoA.

Example 2

Acetoacetyl-CoA Synthetase (AACS) from *Sinorhizobium meliloti*

The acetoacetyl-CoA synthetase (AACS) having amino acid sequence SEQ ID No. 3 and corresponding cDNA sequence SEQ ID No. 4 from *S. meliloti* catalyses the conversion of acetoacetate and coenzyme A with consumption of ATP into acetoacetyl-CoA and AMP. However, in the framework of the present invention, the reverse reaction was of interest.

The corresponding gene acsA2 was cloned into the expression vector pET30 Xa/LIC as disclosed in Aneja, P., R. Dziak, G.-Q. Cai, T. C. Charles. 2002. Identification of an Acetoacetyl Coenzyme A Synthetase-Dependent Pathway for Utilization of L-(+)-3-hydroxybutyrate in *Sinorhizobium meliloti*. J. Bacteriol. 184:1571-1577. The plasmid "pRD112" obtained in this way mediates N-terminal fusion of the target protein to a His tag which in turn makes purification possible by affinity chromatography on $Ni^{2+}$-NTA agarose.

The protein was expressed in *E. coli* BL21 (DE3) cells at 37° C. and 180 rpm. At an optical density ($OD_{600nm}$) of 0.5-0.6, the culture was induced with 1 mM IPTG and then incubated for a further 3 h. Successful expression of the protein (approx. 72 kDa) was demonstrated by samples taken during the growth.

Figure 6:
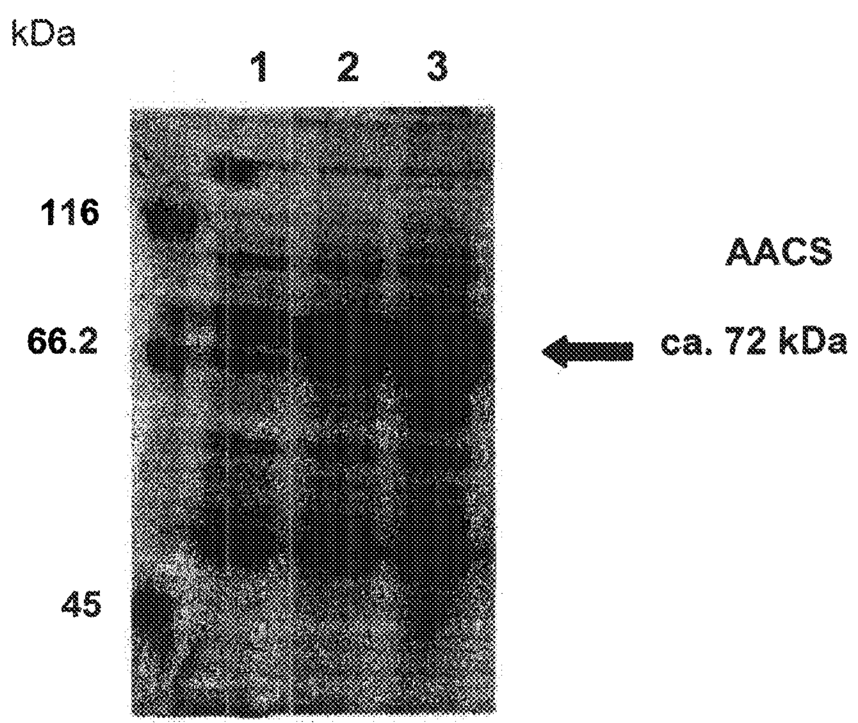

FIG. 6 depicts a 7.5% SDS-PAGE gel after Coomassie staining; in each case 15 μl of crude extract/trace (rapid cell disruption) were loaded. 1: before induction, 2: 1 h after induction, 3: 2 h after induction Purification took place in analogy to that of $TEII_{srf}$ by metal chelate affinity chromatography on $Ni^{2+}$-NTA agarose and a gradient of 20-250 mM imidazole (FIG. 7A). Two peaks (1 and 2) appeared during this, and fractions thereof were examined for their protein content. A subsequent analysis in 7.5% SDS-PA gels showed, especially for the first peak, the occurrence of an additional band at about 55 kDa. Since this band was distinctly weaker in the second peak or did not occur at all, the corresponding fractions of this peak were combined and employed for the activity determination. The substrates in the DTNB assay were again acetoacetyl-CoA and, for comparison, acetyl-CoA. Determination of the Km values gave a value of $7\times10^{-4}$ mol·$l^{-1}$ (0.7 mM) for acetyl-CoA as substrate. On the other hand, the measured values for acetoacetyl-CoA were insufficient to determine a Km. However, since the specific activity of the enzyme with acetoacetyl-CoA was only 0.0038 μmol·$min^{-1}$·$mg^{-1}$, the AACS from *S. meliloti* was not used further, nor was the corresponding gene cloned in combination with the clostridial genes. FIG. 7 shows the purification of AACS from *E. coli*, the upper portion depicts the FPLC elution profile on $Ni^{2+}$-NTA agarose (Qiagen Superflow, bed volume 5 ml) with the programme washing 0-100 ml, elution 100-150 ml with 20-250 mM imidazole (linear gradient), fraction size 1 ml each; the lower portion shows a 7.5% SDS-PAGE gel after silver staining, selected elution fractions from peak 1 and peak 2, in each case 1 μg of protein/lane, CE: crude extract, FT: flow-through.

Example 3

Acyl-CoA Thioesterase YbgC from *Haemophilus influenzae*

The YbgC protein with amino acid sequence SEQ ID No. 5 and corresponding cDNA sequence SEQ ID No. 6 from *H. influenzae* shows similarities with a corresponding protein from *E. coli*, the latter as cytoplasmic protein belonging to the so-called Tol-Pal system. This is widespread in Gram-negative bacteria. It is important for maintaining cell wall integrity and possibly has a function in the transport of substances through the periplasm. The function of YbgC in *H. influenzae* and any relations to functions of the Tol-Pal system have not on the other hand been published to date. However, the publication by Zhuang et al. (2002) describes investigations of the catalytic function of this protein and analysis of a thioesterase activity. It was possible to show in this case the hydrolysis of short-chain aliphatic acyl-CoA esters such as, for example, propionyl-CoA and butyryl-CoA (Km values 11-24 mM) by YbgC (Zhuang Z., F. Song, B. M. Martin, D. Dunaway-Mariano. 2002. The YbgC protein encoded by the ybgC gene of the tol-pal gene cluster of *Haemophilus influenzae* catalyzes acyl-coenzyme A thioester hydrolysis. FEBS Lett. 516:161-163).

An in-vitro detection of an activity with acetyl-CoA and acetoacetyl-CoA within the scope of this project again depended on purification of the protein. Starting from genomic DNA, the gene was cloned into a different expression system, the IMPACT™ (Intein Mediated Purification with an Affinity Chitin-binding-Tag) system from NEB (Frankfurt a. M). Its advantage is that this method makes it possible to purify a recombinant protein simply in its native form, i.e. without Tag.

Cloning of ybgc into the vector pTYB1 (NEB Frankfurt a. M.) made it possible to express and subsequently purify the acyl-CoA thioesterase YbgC from *E. coli.*

The ybgc gene was amplified by PCR from genomic DNA with the primers ybgcTYB1Ndefw (ATA TAC ATA TGT TGG ATA ATG GCT TTT C (SEQ ID NO: 22)) and ybgcTYB1Xhorev (TCC GAA CTC GAG TTT TAA GTG ATG (SEQ ID NO: 23)). In this case, the primers mediated incorporation of an NdeI cleavage site at the 5' end and of an XhoI cleavage site at the 3' end of the amplified fragment. The Taq Mastermix (Qiagen, Hilden) was employed according to the statements of the manufacturer under the following conditions:

| Temperature | Time | Cycles |
|---|---|---|
| 94° C. | 2 min | 1 |
| 94° C. | 30 s | 30 |
| 55° C. | 1 min | |
| 72° C. | 1 min | |
| 72° C. | 10 min | 1 |

A fragment of the expected size of about 430 bp was obtained. This was initially subcloned into the pJET vector (Fermentas, St. Leon-Rot) in accordance with the manufacturer's instructions (pJet_ybgcTYB, 410 bp). Subsequently, the ybgc fragment was cut out of this plasmid again with the restriction endonucleases NdeI and XhoI and gel-eluted (gel extraction kit; peqlab Biotechnologie GmbH, Erlangen, in accordance with the manufacturer's instructions). The vector pTYB1 (7477 bp) was likewise cleaved with NdeI and XhoI (7439 bp) and then ligated to the cleaved and gel-eluted ybgc fragment using the Rapid Ligation Kit in accordance with the manufacturer's instructions (Fermentas GmbH, St. Leon-Rot). 10 μl portions of the ligation mixture were employed to transform 100 μl of $CaCl_2$-competent *E. coli* XL1-B cells. The resulting clones were then grown in LB-ampicillin liquid medium, and the plasmid DNA was isolated. The isolated plasmids were checked by restriction analysis (NdeI/XhoI) and sequenced (Agowa GmbH, Berlin). The resulting plasmid was called pTYBybgc (SEQ ID No. 15) and employed for further transformation in *E. coli* BL21 DE3.

Expression took place in *E. coli* BL21 (DE3) in $LB_{Amp}$ medium until induction at an $OD_{600nm}$ of ~0.5 with 0.5 mM IPTG at 37° C., and thereafter the culture was incubated at 20° C. and 150 rpm for a further 6 h. The heterologously expressed fusion protein (approx. 70 kDa) binds to chitin. Addition of DTT causes a conformational change and induces cutting out of the target protein (approx. 15 kDa), which can subsequently be eluted. FIG. 8 shows SDS-PAGE gels. The upper portion depicts an SDS-PAGE for analysing the expression of YbgC. It is a 10-20% gradient SDS-PA gel after Coomassie staining. In each case 15 μl of crude extract/lane (rapid cell disruption) were loaded. 1: before induction, 2, 3: 6 h after induction. The lower part depicts the progress of purification of YbgC on chitin columns in a 10-20% gradient SDS-PA gel after silver staining. In each case 2 μg of protein/lane were loaded; —CE: crude extract, FT: flow-through, W: washing fractions, eluates: protein-containing elution fractions (fraction size: 1 ml each).

Although the elution fractions showed, besides the desired protein of 15 kDa, also bands of the fusion protein and of the cleaved-off intein domain, they were used for the in vitro activity determination in the DTNB assay. Although the measurements to ascertain the Km varied (data not shown), it was possible to ascertain a Km of $5.3\times10^{-4}$ mol·$l^{-1}$ (0.53 mM) for acetyl-CoA, and a Km of $1.4\times10^{-4}$ mol·$l^{-1}$ (0.14 mM) for acetoacetyl-CoA as substrate. It was thus possible to determine in the direct comparison that the substrate affinity of the enzyme for acetoacetyl-CoA was in fact increased. These results were in favour of including YbgC in the further cloning experiments.

Example 4

Cloning Strategy for Constructing the Expression Vectors

For acetone production in *E. coli*, cloning of suitable acyl-CoA thioesterase or acyl-CoA synthetase/acyl-CoA thiokinase genes together with the genes thlA (gene product with amino acid sequence having SEQ ID No. 16 and corresponding cDNA sequence SEQ ID No. 17, thiolase A) and adc (gene product having amino acid sequence with SEQ ID No. 18 and corresponding cDNA sequence SEQ ID No. 19, acetoacetate decarboxylase) from *C. acetobutylicum* was carried out. The plasmids pSK and pKS were initially selected for this purpose. These are cloning vectors which differ essentially in the orientation of the multi cloning site (MCS). The MCS is in each case located inside a lacZ' gene sequence which is present and which codes for the N-terminal fragment of β-galactosidase and permits blue-white screening of recombinant plasmids. For the experiments within the context of the project, priority was given to expression of the cloned genes under the control of the inducible lac promoter. The vector pSK was provided for this purpose. In addition, a variant was generated by integration into the plasmid pKS, and in this case the genes were to be expressed under the control of the constitutive thiolase promoter from *C. acetobutylicum*.

Cloning of the respective genes into the vectors took place sequentially. For this purpose, initially oligonucleotides were designed for amplification of the genes with introduction of appropriate cleavage sites, and polymerase chain reactions were carried out. All the fragments were amplified and cloned as depicted into the vectors. The strategic procedure and the restriction cleavage sites used in the case of pSK are illustrated diagrammatically in FIG. 9. The procedure with the plasmid pKS was analogous.

The cloning steps are disclosed in detail below:

Cloning of the genes adc, teII, thlA into the plasmid pKS:

The aim was to clone the genes adc (acetoacetate decarboxylase from *Clostridium acetobutylicum*), $teII_{srf}$ (thioesterase II from *Bacillus subtilis*) and thlA (thiolase from *C. acetobutylicum*) together into a vector and subsequently express them in *E. coli*. The acetoacetate decarboxylase gene adc was amplified by means of PCR from the plasmid pDrive_adc (SEQ ID No. 20) with the primers AdcXhofwneu (CAT GCT CGA GAC GCG TTA CGT ATC (SEQ ID NO: 24)) and AdcAparevneu (GAT GGG GCC CTG AAT TCT ATT ACT TAA G (SEQ ID NO: 25)). In this case, the primers mediated incorporation of an XhoI cleavage site at the 5' end and of an ApaI cleavage site at the 3' end of the amplified fragment. The polymerase GoTaq (Promega GmbH, Mannheim) was employed in accordance with the statements of the manufacturer with the addition of 4 mM $MgCl_2$ and the following conditions:

| Temperature | Time | Cycles |
|---|---|---|
| 95° C. | 2 min | 1 |
| 95° C. | 30 s | 30 |
| 60° C. | 30 s | |
| 72° C. | 1 min | |
| 72° C. | 1 min | 1 |

A fragment of the expected size of about 800 bp was obtained. This was gel-eluted (Gel extraction Kit; peqlab Biotechnologie GmbH, Erlangen, in accordance with the manufacturer's instructions) and then cleaved, just like the plasmid pKS, with the restriction endonucleases XhoI and ApaI (788 bp), and the vector was additionally dephosphorylated (Antarctic phosphatase, New England Biolabs GmbH, Frankfurt a. M., in accordance with the manufacturer's instructions). This was followed by ligation of the vector and fragment treated in this way with T4 ligase (New England Biolabs GmbH, Frankfurt a. M.) in accordance with the manufacturer's instructions. 10 μl portions of ligation mixture were employed to transform 100 μl of $CaCl_2$-competent *E. coli* XL1-B cells. For each mixture, 100 μl of $CaCl_2$-competent *E. coli* XL1-B cells were transferred into precooled 1.5 ml reaction vessels, and 10 μl of ligation mixture were added in each case and cautiously mixed, and the mixtures were incubated on ice for 30 min. This was followed by a heat shock at 42° C. for 90 s, and the cells were then placed on ice again for 2 min, 0.5 ml of prewarmed LB medium was added in each case, and the mixtures were incubated at 37° C. with gentle shaking for 60 min. 100-300 μl of each mixture were plated out on LB-ampicillin medium and incubated at 37° C. overnight. The resulting clones were then grown in LB-ampicillin liquid medium, and the plasmid DNA was isolated according to the following protocol: a modification of the steps of the "Qiagen mini-kit" without column purification (Qiagen, Hilden), according to Birnboim and Doly (Birnboim, H. C., J. Doly. 1979. A rapid alkaline extraction procedure for screening recombinant plasmid DNA. Nucleic Acids Res. 7: 1513-1523) was used for rapid isolation of plasmid DNA. The isolated plasmids were checked by restriction analysis (ApaI/XhoI), and positive clones were then sequenced (Agowa GmbH, Berlin). This plasmid was called pKSadc and was employed for the following cloning steps.

The thioesterase II gene $teII_{srf}$ was amplified by PCR from the plasmid pTEIIsrf using the primers TeIISalfw (CAA TTG TCG ACG GAT AAC AAT TTC ACA CAG A (SEQ ID NO: 26)) and TeIIXhorev (CTA TCA ACT CGA GTC CAA GCT CAG CTA ATT AA (SEQ ID NO: 27)). In this case, the primers mediated the incorporation of a SalI cleavage site at the 5' end or an XhoI cleavage site at the 3' end of the amplified fragment. The synergy polymerase (GeneCraft GmbH, Lüdinghausen) was employed in accordance with the statements of the manufacturer under the following conditions:

| Temperature | Time | Cycles |
|---|---|---|
| 95° C. | 2 min | 1 |
| 95° C. | 30 s | 30 |
| 60° C. | 40 s | |
| 72° C. | 1 min | |
| 72° C. | 1 min | 1 |

A fragment of the expected size of about 850 bp was obtained. This was gel-eluted (gel extraction kit; peqlab Biotechnologie GmbH, Erlangen, in accordance with the manufacturer's instructions) and then, just like the plasmid pKSadc, cleaved with the restriction endonucleases SalI and XhoI (831 bp), and the vector was additionally dephosphorylated (Shrimp alkaline phosphatase SAP, Fermentas GmbH, St. Leon-Rot, in accordance with the manufacturer's instructions). This was followed by ligation of the vector and fragment treated in this way using the rapid ligation kit in accordance with the manufacturer's instructions (Fermentas GmbH, St. Leon-Rot). 10 μl portions of ligation mixture were employed to transform 100 μl of $CaCl_2$-competent *E. coli* XL1-B cells. 100-300 μl of each mixture were plated out on LB-ampicillin medium and incubated at 37° C. overnight. Resulting clones were then grown in LB-ampicillin liquid medium, and the plasmid DNA was isolated. The isolated plasmids were checked by restriction analysis (XhoI/SalI), and positive clones were then sequenced (Agowa GmbH, Berlin). This plasmid was called pKSadcte and was employed for the following cloning steps.

The thiolase gene thlA was amplified, including the thiolase promoter, by PCR from genomic DNA from *C. acetobutylicum.*

Isolation of chromosomal DNA from *C. acetobutylicum:*

Chromosomal DNA was isolated from *C. acetobutylicum* in principle according to Bertram (Bertram, J. 1989. Entwicklung eines Systems zum DNA-Transfer and zur Transposon-Mutagenese für *Clostridium acetobutylicum*. Dissertation, Universität Göttingen). For this purpose, the cells were grown anaerobically in 2×YTG medium and harvested at an $OD_{600}$ of about 1.2. The cells were sedimented by centrifugation (5 min, 5000×g, 4° C.). The cell sediment was washed three times with 10 ml of 1×TAE buffer (supplemented with 10% [w/v] sucrose) and then stored at −20° C. The DNA from 90 ml of cell suspension treated in this way was obtained as follows:

1. Suspension of the pellet in 3.8 ml of 1×TAE with sucrose
2. Addition of 1 ml of lysozyme-RNase solution
3. Incubation: 30 min, 37° C.
4. Addition of 500 µl of 0.5M EDTA (pH 8.0), 40 µl of tris-HCl (pH 8.0), 30 µl of SDS (10% [w/v])
5. Incubation: 10 min, 37° C.
6. Addition of 200 µl of proteinase K solution
7. Incubation: 2 h, 37° C.
8. Addition of 1.4 ml of 5M Na perchlorate
9. Addition of 7.3 ml of chloroform-isoamyl alcohol (24:1 [v/v]) on ice
10. Centrifugation: 10 min, 5000×g, 4° C.
11. Removal of the upper, aqueous phase
12. Repetition of steps 9.-11. twice
13. Precipitation of the DNA from the aqueous phase by adding 1 vol. of isopropanol
14. Incubation: 5 min, RT
15. Centrifugation: 20 min, 16 000×g, 4° C.
16. Drying of the pellet at RT for max. 2 h
17. Suspension of the pellet in 2 ml of TE buffer
18. Addition of 200 µl of proteinase K solution
19. Incubation: overnight, 37° C.
20. Increasing the volume to 4 ml with distilled water
21. Addition of 600 µl of 3M Na acetate (pH 5.2)
22. Extraction three times with chloroform-isoamyl alcohol (see steps 9.-11.)
23. Precipitation of the DNA by adding 1 vol. of isopropanol
24. Incubation: 5 min, RT
25. Centrifugation: 20 min, 16 000×g, 4° C.
26. Washing of the pellet with 96% (v/v) ethanol (extra pure, ice-cold) twice
27. Drying of the pellet at RT for a maximum of 2 h
28. Suspension of the pellet in 200 µl of TE The primers PthlAXmafw (CAT GAT TTC CCG GGG GTT AGC ATA TG (SEQ ID NO: 28)) and PthlASalrev (CAG AGT TAT TTT TAA GTC GAC TTT CTA GCA C (SEQ ID NO: 29)) employed for the PCR mediated the incorporation of an XmaI cleavage site at the 5' end and of a SalI cleavage site at the 3' end of the amplified fragment. The Taq Mastermix (Qiagen, Hilden) was employed in accordance with the statements of the manufacturer under the following conditions:

| Temperature | Time | Cycles |
|---|---|---|
| 95° C. | 2 min | 1 |
| 95° C. | 30 s | 30 |
| 60° C. | 40 s | |
| 72° C. | 1.5 min | |
| 72° C. | 1 min | 1 |

A fragment of the expected size of about 1400 bp was obtained. This was initially subcloned into the pJET vector (Fermentas, St. Leon-Rot) in accordance with the manufacturer's instructions (pJet_PthlA). Subsequently, the thlA fragment was cut out of this plasmid again with the restriction endonucleases XhoI and Cfr9I (1397 bp) and gel eluted (gel extraction kit; peqlab Biotechnologie GmbH, Erlangen, in accordance with the manufacturer's instructions). The plasmid pKSadcte was likewise treated with XhoI and Cfr9I and additionally dephosphorylated (Shrimp alkaline phosphatase SAP, Fermentas GmbH, St. Leon-Rot, in accordance with the manufacturer's instructions). This was followed by ligation of the vector and fragment treated in this way using the rapid ligation kit in accordance with the manufacturer's instructions (Fermentas GmbH, St. Leon-Rot). 10 µl portions of ligation mixture were employed to transform 100 µl of $CaCl_2$-competent *E. coli* XL1-B cells. Resulting clones were then grown in LB-ampicillin liquid medium, and the plasmid DNA was isolated. The isolated plasmids were checked by restriction analysis (SalI/Cfrl9I), and positive clones were then sequenced (Agowa GmbH, Berlin).

This plasmid with SEQ ID No. 8 was called pKSatt and was employed for further transformation into various *E. coli* strains, which were subsequently investigated for the formation of acetone.

Cloning of the genes adc, $teII_{srf}$, thlA into the plasmid pSK: To clone the three genes into the vector pSK, initially the adc-$teII_{srf}$ fragment already present in pKS was cut out by restriction with ApaI and SalI (1625 bp) and gel-eluted (gel extraction kit; peqlab Biotechnologie GmbH, Erlangen, in accordance with the manufacturer's instructions) and ligated into the likewise cleaved and dephosphorylated pSK vector (SAP, Fermentas GmbH, St. Leon-Rot, in accordance with the manufacturer's instructions). The Quick Ligation Kit (New England Biolabs GmbH, Frankfurt a. M.) was used in accordance with the manufacturer's instructions for this purpose. The resulting clones were checked by subsequently growing them in LB-ampicillin liquid medium and isolating the plasmid DNA. The isolated plasmids were checked by restriction analysis (ApaI/SalI). The plasmid obtained in this way was called pSKadcte and used further for the subsequent cloning step.

The thiolase gene thlA was amplified by PCR from the plasmid pDrive_line thl (SEQ ID No. 21) with the primers ThlAXmafw (GTC GAC CCG GGT CAA AAT TTA GGA G (SEQ ID NO: 30)) and ThlASalrev (GCT TGT CGA ATT CAG ATC AGA G (SEQ ID NO: 31)). In this case, the primers mediated incorporation of an XmaI cleavage site at the 5' end and of a SalI cleavage site at the 3' end of the amplified fragment. The Taq Mastermix (Qiagen, Hilden) was employed in accordance with the statements of the manufacturer under the following conditions:

| Temperature | Time | Cycles |
|---|---|---|
| 95° C. | 2 min | 1 |
| 95° C. | 30 s | 30 |
| 60° C. | 1 min | |
| 72° C. | 1.5 min | |
| 72° C. | 10 min | 1 |

A fragment of the expected size of about 1250 bp was obtained. This was initially subcloned into the pJET vector (Fermentas, St. Leon-Rot) in accordance with the manufacturer's instructions) (pJet_thlA). The thlA fragment was then cut out of this plasmid again with the restriction endonucleases XhoI and Cfr9I (1243 bp) and gel-eluted (gel extraction kit; peqlab Biotechnologie GmbH, Erlangen, in accordance with the manufacturer's instructions). The plasmid pSKadcte was likewise treated with XhoI and Cfr9I and additionally dephosphorylated (Shrimp alkaline phosphatase SAP, Fermentas GmbH, St. Leon-Rot, in accordance with the manufacturer's instructions). This was followed by ligation of the vector and fragment treated in this way using the Quick Ligation Kit (New England Biolabs GmbH, Frankfurt a. M.) in accordance with the manufacturer's instructions. 10 μl portions of ligation mixture were employed to transform 100 μl of $CaCl_2$-competent *E. coli* XL1-B cells. The resulting clones were then grown in LB-ampicillin liquid medium, and the plasmid DNA was isolated. The isolated plasmids were checked by restriction analysis (SalI/Cfrl9I), and positive clones were then sequenced (Agowa GmbH, Berlin).

This plasmid with SEQ ID No. 7 was called pSKatt and was employed for further transformation into various *E. coli* strains.

It was possible on the basis of the pUC18 construct having SEQ ID No. 14 (pUCadc_ctfA/B_thlA; see FIG. 10), in which the clostridial genes adc, ctfA/B and thlA were already cloned, on the one hand to generate an additional variant in the vector pUC19 in which this gene cassette is expressed under the control of the lac promoter. It was additionally possible subsequently to cut out the genes ctfA/B specifically and, after introduction of the appropriate cleavage sites into the fragments, instead to insert the genes $teII_{srf}$ and ybgC (FIG. 9). In the pUC18 construct, additionally the original thlA fragment was deleted and replaced by a thlA fragment which additionally comprised the thl promoter sequence "upstream".

FIG. 10 shows diagrammatically the generation of pUC19 constructs; at the top the diagrammatic representation of the procedure for the cloning of the gene cassette adc/ctfAB/thlA into the plasmid pUC19, underneath a diagrammatic representation of the procedure for cloning $teII_{srf}$ and ybgC starting from plasmid pUC19act.

The Clonings in Detail:

Construction of the Plasmid pUC19act

The basis for this was the plasmid pUCadc_ctfA/B_thlA having SEQ ID No. 14 which represents the clostridial genes acetoacetate decarboxylase (adc), CoA transferase (ctfA/B) and thiolase (thlA) cloned into the vector pUC18. The genes in this case are cloned in the opposite orientation to the lacZ gene. For the genes to be able to be transcribed under the control of the lac promoter, the adc_ctfA/B_thlA fragment (3311 bp) was cut out again with the restriction endonucleases SalI and EcoRI, and ligated into the vector pUC19 which had been cleaved with the same enzymes (Rapid Ligation Kit in accordance with the manufacturer's instructions; Fermentas GmbH, St. Leon-Rot). 10 μl portions of ligation mixture were employed to transform 100 μl of $CaCl_2$-competent *E. coli* XL1-B cells. Resulting clones were then grown in LB-ampicillin liquid medium, and the plasmid DNA was isolated. The isolated plasmids were checked by restriction analysis (SalI/EcoRI). This plasmid with SEQ ID No. 12 was called pUC19act and employed for further transformation into various *E. coli* strains which were subsequently investigated for the formation of acetone. This construct which contains the clostridial genes for acetone formation moreover served as possibility for comparison with the remaining constructs.

Construction of the Plasmid pUC18att

The basis for this was the plasmid pUCadc_ctfA/B_thlA having SEQ ID No. 14 which represents the clostridial genes for acetoacetate decarboxylase (adc), CoA transferase (ctfA/B) and thiolase (thlA) cloned into the vector pUC18.

The thioesterase II gene $teII_{srf}$ was amplified by PCR from the plasmid pTEIIsrf using the primers TeIIpUCBamfw (CAA TTG GGA TCC GAT AAC AAT TTC ACA CAG (SEQ ID NO: 32)) and TeIIpUCAccrev (GAG ATC TGG TAC CCG GTT AAA TGA TCG GA (SEQ ID NO: 33)). In this case, the primers mediated incorporation of a BamHI cleavage site at the 5' end and of an Acc65I cleavage site at the 3' end of the amplified fragment. The synergy polymerase (GeneCraft GmbH, Lüdinghausen) was employed in accordance with the statements of the manufacturer under the following conditions:

| Temperature | Time | Cycles |
|---|---|---|
| 95° C. | 2 min | 1 |
| 95° C. | 30 s | 30 |
| 61° C. | 30 s | |
| 72° C. | 1 min | |
| 72° C. | 1 min | 1 |

A fragment of the expected size of about 800 bp was obtained. This was initially subcloned into the pJET vector (Fermentas, St. Leon-Rot) in accordance with the manufacturer's instructions (pJet_teIIpUC). The $teII_{srf}$ fragment was then cut out of this plasmid again with the restriction endonucleases BamHI and Acc65I (776 bp) and gel-eluted (Gel extraction Kit; peqlab Biotechnologie GmbH, Erlangen, in accordance with the manufacturer's instructions). The vector pUCadc_ctfA/B_thlA was likewise treated with the restriction enzymes BamHI and Acc65I to extract the ctfA/B fragment (1331 bp). The mixture was fractionated in an agarose gel, and the band with the remaining vector (4633 bp) was gel-eluted (Gel extraction Kit; peqlab Biotechnologie GmbH, Erlangen, in accordance with the manufacturer's instructions). This was followed by ligation of the vector and of the fragment using the Rapid Ligation Kit in accordance with the manufacturer's instructions (Fermentas GmbH, St. Leon-Rot). 10 μl portions of ligation mixture were employed to transform 100 μl of $CaCl_2$-competent *E. coli* XL1-B cells. Resulting clones were then grown in LB-ampicillin liquid medium, and the plasmid DNA was isolated. The isolated plasmids were checked by restriction analysis (BamHI/Acc65I). The resulting plasmid pUC18att_sub was used further for cloning the thlA fragment with thiolase promoter.

The thiolase gene thlA was amplified, including the thiolase promoter, by PCR from genomic DNA from *C. acetobutylicum*. The primers PthlApUCSalfw (CAT GAT TTG TCG ACG GTT AGC ATA TG (SEQ ID NO: 34)) and PthlA-pUCBamrev (CAG AGT TAT TTT TAA GGA TCC TTT CTA GC (SEQ ID NO: 35)) employed for the PCR mediated incorporation of a SalI cleavage site at the 5' end and of a BamHI cleavage site at the 3' end of the amplified fragment. The Taq Mastermix (Qiagen, Hilden) was employed in accordance with the statements of the manufacturer with addition of 2.5 mM $MgSO_4$ and under the following conditions:

| Temperature | Time | Cycles |
|---|---|---|
| 95° C. | 2 min | 1 |
| 95° C. | 30 s | 30 |
| 50° C. | 1 min | |
| 72° C. | 1.5 min | |
| 72° C. | 10 min | 1 |

A fragment of the expected size of about 1400 bp was obtained. This was initially subcloned into the pJET vector (Fermentas, St. Leon-Rot) in accordance with the manufacturer's instructions (pJet_PthlApUC). The thlA fragment was then cut out of this plasmid again with the restriction endonucleases Sail and BamHI (1397 bp) and gel-eluted (Gel extraction Kit; peqlab Biotechnologie GmbH, Erlangen, in accordance with the manufacturer's instructions). The thiolase fragment (without promoter, 1217 bp) was cut out of the previously constructed plasmid pUC18att_sub with SalI and BamHI, and the remaining vector (4192 bp) was gel-eluted, and the thiolase fragment including promoter (1397 bp) was ligated in (Rapid Ligation Kit in accordance with the manufacturer's instructions; Fermentas GmbH, St. Leon-Rot). 10 μl portions of ligation mixture were employed to transform 100 μl of $CaCl_2$-competent *E. coli* XL1-B cells. Resulting clones were then grown in LB-ampicillin liquid medium, and the plasmid DNA was isolated. The isolated plasmids were checked by restriction analysis (SalI/BamHI) and sequenced (Agowa GmbH, Berlin). This plasmid was called pUC18att (SEQ ID No. 10) and was employed for further transformation into various *E. coli* strains which were subsequently investigated for the formation of acetone.

Construction of the Plasmid pUC19att

The basis for this was the plasmid pUC19act which represents the clostridial genes for acetoacetate decarboxylase (adc), CoA transferase (ctfA/B) and thiolase (thlA) cloned into the vector pUC19.

The $teII_{srf}$ fragment was cut out of pJet_teIIpUC with the restriction enzymes BamHI and Acc65I (776 bp) and gel-eluted (Gel extraction Kit; peqlab Biotechnologie GmbH, Erlangen, in accordance with the manufacturer's instructions). The vector pUC19act was cleaved with the same enzymes to extract the ctfA/B fragment. After fractionation in agarose, the remaining vector band (4633 bp) was gel-eluted (Gel extraction Kit; peqlab Biotechnologie GmbH, Erlangen, in accordance with the manufacturer's instructions). This was followed by ligation of vector fragment and teIIpUC fragment. The Quick Ligation Kit (New England Biolabs GmbH, Frankfurt a. M.) was used for this in accordance with the manufacturer's instructions. The transformation took place as described above. To check the resulting clones, they were subsequently grown in LB-ampicillin liquid medium and the plasmid DNA was isolated. The isolated plasmids were checked by restriction analysis (BamHI/Acc65I). The plasmid obtained in this way was called pUC19att (SEQ ID No. 9) and was employed for further transformation into various *E. coli* strains which were subsequently investigated for the formation of acetone.

Construction of the Plasmid pUC19ayt

The basis for this was the plasmid pUC19att.

The gene ybgc for the acyl-CoA thioesterase YbgC from *Haemophilus influenzae* was amplified by PCR from genomic DNA using the primers ybgcpUCBamfw (CTC TAG AAG GAT CCT GTT TAA CTT TAA G (SEQ ID NO: 36)) and ybgcpUCAccrev (ATT GGG TAC CTC ATT GCA TAC TCC G (SEQ ID NO: 37)). In this case, the primers mediated incorporation of a BamHI cleavage site at the 5' end and of an Acc65I cleavage site at the 3' end of the amplified fragment. The Taq Mastermix (Qiagen, Hilden) was employed in accordance with the statements of the manufacturer under the following conditions:

| Temperature | Time | Cycles |
|---|---|---|
| 94° C. | 2 min | 1 |
| 94° C. | 30 s | 30 |
| 57° C. | 1 min | |
| 72° C. | 1 min | |
| 72° C. | 10 min | 1 |

A fragment of the expected size of about 490 bp was obtained. This was initially subcloned into the pJET vector (Fermentas, St. Leon-Rot) in accordance with the manufacturer's instructions (pJet_ybgcpUC). The ybgc fragment was then cut out of this plasmid again with the restriction endonucleases BamHI and Acc65I (465 Bp) and gel-eluted (Gel extraction Kit; peqlab Biotechnologie GmbH, Erlangen, in accordance with the manufacturer's instructions).

The vector pUC19att was likewise treated with the restriction enzymes BamHI and Acc65I to extract the $teII_{srf}$ fragment (468 bp). The mixture was fractionated in an agarose gel, and the band with the remaining vector (4633 bp) was gel-eluted (Gel extraction Kit; peqlab Biotechnologie GmbH, Erlangen, in accordance with the manufacturer's instructions). This was followed by ligation of the vector and the fragment using the rapid ligation kit in accordance with the manufacturer's instructions (Fermentas GmbH, St. Leon-Rot). 10 μl portions of ligation mixture were employed to transform 100 μl of $CaCl_2$-competent *E. coli* XL1-B cells. Resulting clones were then grown in LB-ampicillin liquid medium, and the plasmid DNA was isolated. The isolated plasmids were checked by restriction analysis (BamHI/Acc65I) and sequenced (Agowa GmbH, Berlin). The resulting plasmid was called pUC19ayt (SEQ ID No. 11) and was employed for further transformation into various *E. coli* strains which were subsequently investigated for the formation of acetone.

An overview of the present plasmid constructs is compiled in Table 1.

TABLE 1

Plasmid constructs

| Plasmid | Size in bp | Insert | Promoter |
|---|---|---|---|
| pSKatt | 5771 | $teII_{srf}$(adc, thlA) | lac |
| pKSatt | 5925 | $teII_{srf}$(adc, thlA) | thl |
| pUC19att | 5409 | $teII_{srf}$(adc, thlA) | lac |
| pUC18att | 5589 | $teII_{srf}$(adc, thlA) | thl |
| pUC19ayt | 5101 | ybgC (adc, thlA) | lac |
| pUC19act | 5964 | ctfA/B (adc, thlA) | lac |

Example 5

Acetone Formation in *E. coli*

All the resulting plasmid variants (see Table 1) were investigated for acetone formation in the *E. coli* cloning strain HB101. The analyses took place on the 5 ml scale in LB medium with ampicillin (100 μg/ml) after inoculation from appropriate precultures and after incubation at 37° C. and 200 rpm. The optical density (600 nm) was followed by photometry and, at a value of about 0.5-0.6, expression of the cloned genes was induced by adding 1 mM IPTG (isopropyl β-D-thiogalactopyrano-side) and, after 3-4 h, glucose (20 g/l) was added. No induction took place with the variants under the control of the thiolase promoter because it was assumed that constitutive expression takes place. Samples were taken at particular times over a period of about 48 h, and the concentration of acetone and acetate in the cell-free medium supernatant was determined by gas chromatography. Additional glucose doses optionally took place in varying amounts (in the range 10-40 g/l) either 4 h after induction or else simultaneously with the induction.

Significant acetone productions were detectable in *E. coli* HB101 with all the plasmid variants. FIG. 11 shows by way of example the growth curves with the amounts of acetone and acetate formed for individual variants.

A summary of the results with the maximum acetone concentrations is shown in Table 2.

FIG. 11 depicts in each case the optical density (600 nm) and the acetone and acetate concentrations (mM) at selected times. The black arrow indicates in each case the time when IPTG (1 mM) was added, and the green arrow indicates the addition of glucose (20 g/l).

TABLE 2

Summary of the maximum acetone concentrations of the individual plasmid variants in 5 ml cultures

| Plasmid | Insert | Promoter | Max. acetone concentration strain, medium |
|---|---|---|---|
| pSKatt | $teII_{srf}$ (adc, thlA) | lac | 34 mM (2.0 g/l, HB101, $LB_{Amp}$) |
| pKSatt | $teII_{srf}$ (adc, thlA) | thl | 36 mM (2.1 g/l, HB101, $LB_{Amp}$) |
| pUC19att | $teII_{srf}$ (adc, thlA) | lac | 30 mM (1.7 g/l, HB101, $LB_{Amp}$) |
| pUC18att | $teII_{srf}$ (adc, thlA) | thl | 35 mM (2.0 g/l, HB101, $LB_{Amp}$) |
| pUC19ayt | ybgC (adc, thlA) | lac | 60 mM (3.5 g/l, HB101, $LB_{Amp}$) |
| pUC19act | ctfA/B (adc, thlA) | lac | 46 mM (2.7 g/l, HB101, $LB_{Amp}$) |

Example 6

Comparison of the Acetone Pathway with Cloned ybgC Gene from *H. influenzae* with the Acetone Pathway Consisting Exclusively of Clostridial Genes It was then attempted in a subsequent experiment to reproduce the results obtained also in 100 ml cultures ($LB_{Amp}$) with the variants pUC19ayt and pUC19act as control (37° C., 200 rpm). The main cultures were inoculated with 1 ml of an appropriate preculture and induced with 1 mM IPTG at an $OD_{600nm}$ of 0.5. As difference from the previous experiments, addition of glucose (20 g/l) was repeated 18 h after the first addition. In addition, the glucose content of the culture was determined in parallel at the individual sampling times in order to be able to ascertain the consumption of glucose. The glucose determination was carried out by an optical-enzymatic assay of Bergmeyer (1970) in which the glucose is converted into 6-phosphogluconate and NADPH in two steps by the enzymes hexokinase and glucose-6-phosphate dehydrogenase with addition of ATP and NADP' (Bergmeyer, H. U. (editor-in-chief): Methods of Enzymatic Analysis, 2nd Edition, Verlag Chemie, Weinheim—Deerfield Beach—Basel 1970). The amount of NAPDH formed in this case is proportional to the amount of glucose present and can be determined by the change in extinction by photometry at a wavelength of 340 nm. The results on this are depicted in FIGS. 12 A and 12 B. It is evident that the glucose in culture A (*E. coli* HB101 pUC19ayt) was already completely consumed at the time of the second addition.

However, renewed administration of glucose did not lead to the hoped-for further increase in the amount of acetone, nor was it consumed because obviously no decrease was detectable. It is to be assumed that at this time growth was limited by other factors, since no further increase in the optical density took place either. A maximum of 67 mM (3.9 g/l) acetone as formed. Culture B with the control plasmid pUC19act which was carried out under the same conditions was similar. Glucose was not yet completely consumed at the time of the second addition, but renewed addition of glucose had no effect in relation to an increase in the amount of acetone formed in this case either. The maximum amount of acetone was 20 mM (1.2 g/l). The variant with the cloned ybgC gene from *H. influenzae* therefore produced under these conditions three times as much acetone as the control culture with the exclusively clostridial genes.

FIG. 12 depicts in each case the optical density (600 nm), the acetone and acetate concentration (mM) and the glucose content (g/l) at selected times. The black arrow indicates the time when IPTG (1 mM) was added, and the green arrows indicate the addition of glucose (20 g/l); top: *E. coli* HB101 pUC19ayt, bottom: *E. coli* HB101 pUC19act (control)

The invention claimed is:

1. A process for preparing acetone starting from acetyl-coenzyme A, comprising:

A. contacting acetyl-CoA with a polypeptide that is at least 90% identical to the amino acid sequence of SEQ ID NO: 16 and which converts acetyl CoA into acetoacetyl CoA;

B. contacting the acetoacetyl-CoA with a polypeptide that is at least 90% identical to the amino acid sequence of SEQ ID NO: 1, 3 or 5 and which converts acetoacetyl CoA into acetoacetate and CoA; and C. contacting the acetoacetate with a polypeptide that is at least 90% identical to the amino acid sequence of SEQ ID NO: 18 and which decarboxylates the acetoacetate to produce acetone and $CO_2$;

wherein the coenzyme A in B is not transferred to an acceptor molecule.

2. The process of claim 1, comprising:

A. contacting acetyl-CoA with a polypeptide that is at least 95% identical to the amino acid sequence of SEQ ID NO: 16 and which converts acetyl CoA into acetoacetyl CoA;

B. contacting the acetoacetyl-CoA with a polypeptide that is at least 95% identical to the amino acid sequence of SEQ ID NO: 1, 3 or 5 and which converts acetoacetyl CoA into acetoacetate and CoA; and C. contacting the acetoacetate with a polypeptide that is at least 95% identical to the amino acid sequence of SEQ ID NO: 18 and which decarboxylates the acetoacetate to acetone and $CO_2$;

wherein the coenzyme A in B is not transferred to an acceptor molecule.

3. The method of claim 1, wherein B comprises contacting the acetoacetyl-CoA with a polypeptide that is at least 90% identical to the amino acid sequence of SEQ ID NO: 1 to produce acetoacetate.

4. The method of claim 1, wherein B comprises contacting the acetoacetyl-CoA with a polypeptide that is at least 90% identical to the amino acid sequence of SEQ ID NO: 3 to produce acetoacetate.

5. The method of claim 1, wherein B comprises contacting the acetoacetyl-CoA with a polypeptide that is at least 90% identical to the amino acid sequence of SEQ ID NO: 5 to produce acetoacetate.

6. The process according to claim 1 that is carried out by a microorganism.

7. The process according to claim 6, wherein the microorganism comprises a polynucleotide encoding a polypeptide that is at least 90% identical to the amino acid sequence of SEQ ID NO: 16;

a polynucleotide encoding a polypeptide that is at least 90% identical to the amino acid sequence of SEQ ID NO: 1, 3 or 5; and a polynucleotide encoding a polypeptide that is at least 90% identical to the amino acid sequence of SEQ ID NO: 18.

8. The process of claim 1, comprising:

A. contacting acetyl-CoA with a polypeptide that is at least 98% identical to the amino acid sequence of SEQ ID NO: 16 and which converts acetyl CoA into acetoacetyl CoA;

B. contacting the acetoacetyl-CoA with a polypeptide that is at least 98% identical to the amino acid sequence of SEQ ID NO: 1, 3 or 5 and which converts acetoacetyl CoA into acetoacetate and CoA; and C. contacting the acetoacetate with a polypeptide that is at least 98% identical to the amino acid sequence of SEQ ID NO: 18 and which decarboxylates the acetoacetate to acetone and $CO_2$;

wherein the coenzyme A in B is not transferred to an acceptor molecule.

9. The process of claim 1, comprising:

A. contacting acetyl-CoA with a polypeptide that is at least 99% identical to the amino acid sequence of SEQ ID NO: 16 and which converts acetyl CoA into acetoacetyl CoA;

B. contacting the acetoacetyl-CoA with a polypeptide that is at least 99% identical to the amino acid sequence of SEQ ID NO: 1, 3 or 5 and which converts acetoacetyl CoA into acetoacetate and CoA; and C. contacting the acetoacetate with a polypeptide that is at least 99% identical to the amino acid sequence of SEQ ID NO: 18 and which decarboxylates the acetoacetate to acetone and $CO_2$;

wherein the coenzyme A in B is not transferred to an acceptor molecule.

10. The process of claim 1, comprising:

A. contacting acetyl-CoA with a polypeptide having the amino acid sequence of SEQ ID NO: 16 and which converts acetyl CoA into acetoacetyl CoA;

B. contacting the acetoacetyl-CoA with a polypeptide having the amino acid sequence of SEQ ID NO: 1, 3 or 5 and which converts acetoacetyl CoA into acetoacetate and CoA; and C. contacting the acetoacetate with a polypeptide that is at least 99% identical to the amino acid sequence of SEQ ID NO: 18 and which decarboxylates the acetoacetate to acetone and $CO_2$;

wherein the coenzyme A in B is not transferred to an acceptor molecule.

* * * * *

SEQUENCE LISTING

```
<160> NUMBER OF SEQ ID NOS: 37

<210> SEQ ID NO 1
<211> LENGTH: 246
<212> TYPE: PRT
<213> ORGANISM: Bacillus subtilis

<400> SEQUENCE: 1

Met Gly Gln Leu Phe Lys Ser Phe Asp Ala Ser Glu Lys Thr Gln Leu
1               5                   10                  15

Ile Cys Phe Pro Phe Ala Gly Gly Tyr Ser Ala Ser Phe Arg Pro Leu
            20                  25                  30

His Ala Phe Leu Gln Gly Glu Cys Glu Met Leu Ala Ala Glu Pro Pro
        35                  40                  45

Gly His Gly Thr Asn Gln Thr Ser Ala Ile Glu Asp Leu Glu Glu Leu
    50                  55                  60
```

-continued

```
Thr Asp Leu Tyr Lys Gln Glu Leu Asn Leu Arg Pro Asp Arg Pro Phe
65                  70                  75                  80

Val Leu Phe Gly His Ser Met Gly Gly Met Ile Thr Phe Arg Leu Ala
                85                  90                  95

Gln Lys Leu Glu Arg Glu Gly Ile Phe Pro Gln Ala Val Ile Ile Ser
            100                 105                 110

Ala Ile Gln Pro Pro His Ile Gln Arg Lys Lys Val Ser His Leu Pro
        115                 120                 125

Asp Asp Gln Phe Leu Asp His Ile Ile Gln Leu Gly Gly Met Pro Ala
    130                 135                 140

Glu Leu Val Glu Asn Lys Glu Val Met Ser Phe Phe Leu Pro Ser Phe
145                 150                 155                 160

Arg Ser Asp Tyr Arg Ala Leu Glu Gln Phe Glu Leu Tyr Asp Leu Ala
                165                 170                 175

Gln Ile Gln Ser Pro Val His Val Phe Asn Gly Leu Asp Asp Lys Lys
            180                 185                 190

Cys Ile Arg Asp Ala Glu Gly Trp Lys Lys Trp Ala Lys Asp Ile Thr
        195                 200                 205

Phe His Gln Phe Asp Gly Gly His Met Phe Leu Leu Ser Gln Thr Glu
    210                 215                 220

Glu Val Ala Glu Arg Ile Phe Ala Ile Leu Asn Gln His Pro Ile Ile
225                 230                 235                 240

Gln Pro Gly Ser Arg Ser
                245
```

```
<210> SEQ ID NO 2
<211> LENGTH: 741
<212> TYPE: DNA
<213> ORGANISM: Clostridium acetobutylicum

<400> SEQUENCE: 2

atgggccaac tcttcaaatc atttgatgcg tcggaaaaaa cacagctcat ctgttttccg     60

tttgccggcg gctattcggc gtcgtttcgc cctctccatg ctttttgca gggggagtgc    120

gagatgctcg ctgccgagcc gccgggacac ggcacgaatc aaacgtcagc cattgaggat    180

ctcgaagagc tgacggattt gtacaagcaa gaactgaacc ttcgccctga tcggccgttt    240

gtgctgttcg gacacagtat gggcggaatg atcaccttca ggctggcgca aaagcttgag    300

cgtgaaggca tctttccgca ggcggttatc atttctgcaa tccagccgcc tcatattcag    360

cggaagaaag tgtcccacct gcctgatgat cagtttctcg atcatattat ccaattaggc    420

ggaatgcccg cagagcttgt tgaaaataag gaggtcatgt cctttttcct gccttctttc    480

cgatcagatt accgggctct tgaacaattt gagctttacg atctggccca gatccagtcg    540

cctgttcatg tctttaacgg gcttgatgat aaaaaatgca tacgagatgc ggaagggtgg    600

aagaagtggg caaaagacat cacattccat caatttgacg gcgggcacat gttcctgctg    660

tcacaaacgg aagaagtcgc agaacggatt tttgcgatct tgaatcagca tccgatcatt    720

caaccgggat ccagatctta a                                               741
```

```
<210> SEQ ID NO 3
<211> LENGTH: 650
<212> TYPE: PRT
<213> ORGANISM: Sinorhizobium meliloti
```

```
<400> SEQUENCE: 3

Met Gln Ala Glu Arg Pro Leu Trp Val Pro Asp Arg Glu Ile Val Glu
1               5                   10                  15

Arg Ser Pro Met Ala Glu Phe Ile Asp Trp Cys Gly Glu Arg Phe Gly
            20                  25                  30

Arg Ser Phe Ala Asp Tyr Asp Ala Phe His Asp Trp Ser Val Ser Glu
        35                  40                  45

Arg Gly Ala Phe Trp Thr Ala Val Trp Glu His Cys Lys Val Ile Gly
    50                  55                  60

Glu Ser Gly Glu Lys Ala Leu Val Asp Gly Asp Arg Met Leu Asp Ala
65                  70                  75                  80

Arg Phe Phe Pro Glu Ala Arg Leu Asn Phe Ala Glu Asn Leu Leu Arg
                85                  90                  95

Lys Thr Gly Ser Gly Asp Ala Leu Ile Phe Arg Gly Glu Asp Lys Val
            100                 105                 110

Ser Tyr Arg Leu Thr Trp Asp Glu Leu Arg Ala Leu Val Ser Arg Leu
        115                 120                 125

Gln Gln Ala Leu Arg Ala Gln Gly Ile Gly Ala Gly Asp Arg Val Ala
    130                 135                 140

Ala Met Met Pro Asn Met Pro Glu Thr Ile Ala Leu Met Leu Ala Thr
145                 150                 155                 160

Ala Ser Val Gly Ala Ile Trp Ser Ser Cys Ser Pro Asp Phe Gly Glu
                165                 170                 175

Gln Gly Val Leu Asp Arg Phe Gly Gln Ile Ala Pro Lys Leu Phe Ile
            180                 185                 190

Val Cys Asp Gly Tyr Trp Tyr Asn Gly Lys Arg Gln Asp Val Asp Ser
        195                 200                 205

Lys Val Arg Ala Val Ala Lys Ser Leu Gly Ala Pro Thr Val Ile Val
    210                 215                 220

Pro Tyr Ala Gly Asp Ser Ala Ala Leu Ala Pro Thr Val Glu Gly Gly
225                 230                 235                 240

Val Thr Leu Ala Asp Phe Ile Ala Gly Phe Gln Ala Gly Pro Leu Val
                245                 250                 255

Phe Glu Arg Leu Pro Phe Gly His Pro Leu Tyr Ile Leu Phe Ser Ser
            260                 265                 270

Gly Thr Thr Gly Val Pro Lys Cys Ile Val His Ser Ala Gly Gly Thr
        275                 280                 285

Leu Leu Gln His Leu Lys Glu His Arg Phe His Cys Gly Leu Arg Asp
    290                 295                 300

Gly Glu Arg Leu Phe Tyr Phe Thr Thr Cys Gly Trp Met Met Trp Asn
305                 310                 315                 320

Trp Leu Ala Ser Gly Leu Ala Val Gly Ala Thr Leu Cys Leu Tyr Asp
                325                 330                 335

Gly Ser Pro Phe Cys Pro Asp Gly Asn Val Leu Phe Asp Tyr Ala Ala
            340                 345                 350

Ala Glu Arg Phe Ala Val Phe Gly Thr Ser Ala Lys Tyr Ile Asp Ala
        355                 360                 365

Val Arg Lys Gly Gly Phe Thr Pro Ala Arg Thr His Asp Leu Ser Ser
    370                 375                 380

Leu Arg Leu Met Thr Ser Thr Gly Ser Pro Leu Ser Pro Glu Gly Phe
385                 390                 395                 400

Ser Phe Val Tyr Glu Gly Ile Lys Pro Asp Val Gln Leu Ala Ser Ile
                405                 410                 415
```

```
Ser Gly Gly Thr Asp Ile Val Ser Cys Phe Val Leu Gly Asn Pro Leu
            420                 425                 430

Lys Pro Val Trp Arg Gly Glu Ile Gln Gly Pro Gly Leu Gly Leu Ala
        435                 440                 445

Val Asp Val Trp Asn Asp Glu Gly Lys Pro Val Arg Gly Glu Lys Gly
    450                 455                 460

Glu Leu Val Cys Thr Arg Ala Phe Pro Ser Met Pro Val Met Phe Trp
465                 470                 475                 480

Asn Asp Pro Asp Gly Ala Lys Tyr Arg Ala Ala Tyr Phe Asp Arg Phe
                485                 490                 495

Asp Asn Val Trp Cys His Gly Asp Phe Ala Glu Trp Thr Pro His Gly
            500                 505                 510

Gly Ile Val Ile His Gly Arg Ser Asp Ala Thr Leu Asn Pro Gly Gly
        515                 520                 525

Val Arg Ile Gly Thr Ala Glu Ile Tyr Asn Gln Val Glu Gln Met Asp
    530                 535                 540

Glu Val Ala Glu Ala Leu Cys Ile Gly Gln Asp Trp Glu Asp Asp Val
545                 550                 555                 560

Arg Val Val Leu Phe Val Arg Leu Ala Arg Gly Val Glu Leu Thr Glu
                565                 570                 575

Ala Leu Thr Arg Glu Ile Lys Asn Arg Ile Arg Ser Gly Ala Ser Pro
            580                 585                 590

Arg His Val Pro Ala Lys Ile Ile Ala Val Ala Asp Ile Pro Arg Thr
        595                 600                 605

Lys Ser Gly Lys Ile Val Glu Leu Ala Val Arg Asp Val Val His Gly
    610                 615                 620

Arg Pro Val Lys Asn Lys Glu Ala Leu Ala Asn Pro Glu Ala Leu Asp
625                 630                 635                 640

Leu Phe Ala Gly Leu Glu Glu Leu Lys Ser
                645                 650


<210> SEQ ID NO 4
<211> LENGTH: 1953
<212> TYPE: DNA
<213> ORGANISM: Sinorhizobium meliloti

<400> SEQUENCE: 4

atgcaagcag aacgaccttt gtgggttccg gacagggaga tagtcgaacg cagcccgatg      60

gctgagttca ttgactggtg cggggagcgc ttcgggcgca gcttcgccga ctatgatgcc     120

tttcatgact ggtcggtgag cgagcgcggc gcgttctgga ccgccgtatg ggaacattgc     180

aaggtcatcg gcgaaagcgg ggagaaggcg ctcgtcgacg gcgaccggat gctcgatgcc     240

cgtttctttc cggaagcgag gctcaacttc gccgaaaacc tgctgcgcaa gacggggagc     300

ggcgatgcct tgatcttccg cggcgaggac aaggtgagct accggctgac ctgggacgaa     360

ctgcgcgccc tggtgtcgcg tctgcaacag gcgctgaggg cgcaggggat cggcgccggc     420

gaccgcgtct ccgcgatgat gccgaacatg cccgagacga tcgcactcat gcttgcgacc     480

gcttccgtcg gcgccatctg gtcgtcctgt tcgcccgatt tcggcgagca gggcgtcctc     540

gaccgcttcg gccagatcgc ccccaagctc ttcatcgttt gcgacggcta ctggtacaac     600

ggcaagcggc aggacgtgga ctcgaaggtg cgtgcggtgg ccaagtcgct cggcgcgccc     660

accgtcatcg ttccctatgc cggagacagc gccgcgcttg cgccgaccgt cgagggcggg     720

gtgacgcttg ccgatttcat cgccggattc caggccggac cgcttgtctt cgagcgcctg     780
```

```
ccgttcggcc atccgctcta catactgttc tcctcgggca cgaccggcgt acccaaatgc    840

atcgtccatt cggccggcgg aacgctgctg cagcacctca aggaacatcg cttccattgc    900

gggctgaggg acggcgagcg gctgttctat ttcaccacct gcggctggat gatgtggaac    960

tggctggcct cgggcctcgc cgtgggcgca actctgtgcc tctatgactg ctcacctttt   1020

tgccccgacg gcaacgtgct cttcgattat gccgccgccg aacgcttcgc cttgttcggc   1080

acctcggcga aatatatcga cgccgtgcgc aagggcgggt tcaccccggc aaggacgcac   1140

gatctgtcgt ccttgcgggt catgacgtcc accggctcgc cgctttcgcc ggagggcttc   1200

tccttcgtct atgagggcat caagcccgat gtccagctcg cctcgatttc cggcggcacc   1260

gacatcgtct cctgcttcgt gctcggcaat cccctgaaac ccgtgtggcg cggagagatt   1320

cagggccccg gcctcgggct cgccgtcgat gtctggaacg acgaaggcaa gccggtgcgc   1380

ggggaaaagg gcgaactcgt ctgcaccagg gcgtttccgt cgatgcctgt catgttctgg   1440

aacgatccgg acggcgcgaa gtatcgagcc gcctatttcg accgcttcga caatgtctgg   1500

tgccacggcg attttgccga atggacaccg catggcggca tcgtcatcca cggccgttcc   1560

gacgcgacat tgaaccccgg cggcgtgcgc atcggcacgg cggagatcta caatcaggtc   1620

gaacagatgg atgaagtcgc cgaagcactg tgcatcggcc aggactggga ggacgatgtc   1680

cgcgtcgtcc tgttcgtgcg gctggcccgc ggggtcgaac tgaccgaagc actgaccagg   1740

gagatcaaga accggatccg gtccggcgcc tcgccgcggc acgtgccggc gaagatcatc   1800

gccgtcgccg acatcccgcg caccaagtcc ggcaagatcg tcgaactggc ggtgcgcgac   1860

gtggtgcacg gccgtccggt caagaacaag gaagcgctgg cgaacccgga agctctcgac   1920

ctctttgcgg ggctcgagga actcaagagc tga                                1953
```

```
<210> SEQ ID NO 5
<211> LENGTH: 136
<212> TYPE: PRT
<213> ORGANISM: Haemophilus influenzae

<400> SEQUENCE: 5

Met Leu Asp Asn Gly Phe Ser Phe Pro Val Arg Val Tyr Tyr Glu Asp
1               5                   10                  15

Thr Asp Ala Gly Gly Val Val Tyr His Ala Arg Tyr Leu His Phe Phe
            20                  25                  30

Glu Arg Ala Arg Thr Glu Tyr Leu Arg Thr Leu Asn Phe Thr Gln Gln
        35                  40                  45

Thr Leu Leu Glu Glu Gln Gln Leu Ala Phe Val Val Lys Thr Leu Ala
    50                  55                  60

Ile Asp Tyr Cys Val Ala Ala Lys Leu Asp Asp Leu Leu Met Val Glu
65                  70                  75                  80

Thr Glu Val Ser Glu Val Lys Gly Ala Thr Ile Leu Phe Glu Gln Arg
                85                  90                  95

Leu Met Arg Asn Thr Leu Met Leu Ser Lys Ala Thr Val Lys Val Ala
            100                 105                 110

Cys Val Asp Leu Gly Lys Met Lys Pro Val Ala Phe Pro Lys Glu Val
        115                 120                 125

Lys Ala Ala Phe His His Leu Lys
    130                 135


<210> SEQ ID NO 6
<211> LENGTH: 411
<212> TYPE: DNA
```

<213> ORGANISM: Haemophilus influenzae

<400> SEQUENCE: 6

```
atgttggata atggcttttc ttttcctgtt cgtgtgtatt atgaagatac tgatgcaggt     60
ggcgtagtgt atcacgctcg ctatttgcat ttttttgaac gagcaagaac agaatatttg    120
cgtacattaa attttacgca acaaacctta ctagaggaac aacaactcgc atttgttgtc    180
aaaacgctcg ccattgatta ttgcgtggca gcaaaattgg atgatttact tatggtggaa    240
acagaggttt cagaagtaaa aggggctaca atcctttttg aacagagact gatgcgcaac    300
accctgatgt tatcaaaggc tactgttaag gtagcctgtg ttgatctagg caagatgaaa    360
ccagtggcgt ttcccaaaga agttaaagcg gcgtttcatc acttaaaata a             411
```

<210> SEQ ID NO 7
<211> LENGTH: 5765
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 7

```
ctgacgcgcc ctgtagcggc gcattaagcg cggcgggtgt ggtggttacg cgcagcgtga     60
ccgctacact tgccagcgcc ctagcgcccg ctcctttcgc tttcttccct tcctttctcg    120
ccacgttcgc cggctttccc cgtcaagctc taaatcgggg gctcccttta gggttccgat    180
ttagtgcttt acggcacctc gaccccaaaa aacttgatta gggtgatggt tcacgtagtg    240
ggccatcgcc ctgatagacg gtttttcgcc ctttgacgtt ggagtccacg ttctttaata    300
gtggactctt gttccaaact ggaacaacac tcaaccctat ctcggtctat tcttttgatt    360
tataagggat tttgccgatt tcggcctatt ggttaaaaaa tgagctgatt taacaaaaat    420
ttaacgcgaa ttttaacaaa atattaacgc ttacaatttc cattcgccat tcaggctgcg    480
caactgttgg gaagggcgat cggtgcgggc ctcttcgcta ttacgccagc tggcgaaagg    540
gggatgtgct gcaaggcgat taagttgggt aacgccaggg ttttcccagt cacgacgttg    600
taaaacgacg gccagtgagc gcgcgtaata cgactcacta tagggcgaat tgggtaccgg    660
gccctgaatt ctattactta agataatcat atataacttc agctctaggc aatattatat    720
ctgcaagaat gtgagagcta gaaacaatct cttttactgg caaatcatta agtggcgcca    780
tagcgtgatc aaataactgc agtcgagttg gtcctgtcca agcttcatgt acggtaacat    840
ctgtgatttt cgcatttata agctcacata ttctagggct tccatcataa ttgggtatta    900
ttttcaacat ataattaggg cgacaaattt gatcctttgc ttcattagca tctaaggctt    960
tatgtttgta ccccattgta gctgtcgcaa ctctaagttt tccatagtct aaagttccta   1020
ctaaagtatc tgaatccaca aaaagctttg gatacccgag ctttttagga tatgcactta   1080
attcccttcc tactgcaatt gcaggctcat tatctaaata catcatatga agataatctc   1140
ccttaactcc attaaagctt acgggaatag cctgtccgct ttctgtataa caaccaagtc   1200
cactcgtatc atgcattgcc ataatttcaa acctgactaa gggctcatca atttctaaag   1260
gctctggcac aactttacga agtgcatcca tatctgtacg atatacaatg ttaaaatact   1320
cacgattatg aaatttatag ggtcctctag gaaatgcagg cgaagttaat ggcgtgctaa   1380
tttgtttaat tacttcatcc tttaacataa aaggtacctt ccaatctgga tacgtaacgc   1440
gtctcgagtc caagctcagc taattaagct tagtgatggt gatggtgatg agatcccggt   1500
```

```
tgaatgatcg gatgctgatt caagatcgca aaaatccgtt ctgcgacttc ttccgtttgt   1560
gacagcagga acatgtgccc gccgtcaaat tgatggaatg tgatgtcttt tgcccacttc   1620
ttccaccctt ccgcatctcg tatgcatttt ttatcatcaa gcccgttaaa gacatgaaca   1680
ggcgactgga tctgggccag atcgtaaagc tcaaattgtt caagagcccg gtaatctgat   1740
cggaaagaag gcaggaaaaa ggacatgacc tccttatttt caacaagctc tgcgggcatt   1800
ccgcctaatt ggataatatg atcgagaaac tgatcatcag gcaggtggga cactttcttc   1860
cgctgaatat gaggcggctg gattgcagaa atgataaccg cctgcggaaa gatgccttca   1920
cgctcaagct tttgcgccag cctgaaggtg atcattccgc ccatactgtg tccgaacagc   1980
acaaacggcc gatcagggcg aaggttcagt tcttgcttgt acaaatccgt cagctcttcg   2040
agatcctcaa tggctgacgt ttgattcgtg ccgtgtcccg gcggctcggc agcgagcatc   2100
tcgcactccc cctgcaaaaa agcatggaga gggcgaaacg acgccgaata gccgccggca   2160
aacggaaaac agatgagctg tgtttttttcc gacgcatcaa atgatttgaa gagttggccc   2220
atggttaatt tctcctcttt aatgaattct gtgtgaaatt gttatccgtc gaggtcgacg   2280
aattcagatc agagttattt ttaaggatcc tttctagcac ttttctagca atattgctgt   2340
tccttgtccg ccacctatac ataaagttgc taagcctttt tttgcatctc tttttttgcat   2400
tgcgtgtaca agagtaacga gtattcttgc acctgatgct ccaattggat gaccaagggc   2460
aatagctcct ccatttacat ttactttatt catatcaaat tttaaatctt ttgctactgc   2520
taaactttga gctgcaaaag cttcatttga ttctattaaa tctaattcat caactgtcca   2580
acctgctttt tcaatagctg cttttgttgc atagaaaggt ccatatccca ttattgctgg   2640
gtcaactcct gctgaaccat aagaaactat cttagcaagt ggttttactc caagctcttt   2700
agctttttct gcactcatga ttacaagtac tgctgcacag tcatttaatc ctgatgcatt   2760
accagctgta actgttccat ctttttgaa ggcaggtttt aattttgcaa gtccttctat   2820
agttgatcca aatctagggt gctcatctgt atcaactaca gtttctccct ttctgccttt   2880
aattactaca ggaactattt catctttaaa ttgacctgat tttatagctt cttcagcttt   2940
tttttgtgat gcaagagcaa actcatcttg ttcttctctt gaaatgttcc atctctcagc   3000
tatgttttct gctgttattc ccatgtggta atcattaaat gcatcccaca atccgtcagt   3060
gatcatttca tcaacaaatt tagcgtttcc cattctatat ccccatctag cgttattcgc   3120
taagtaagga gctctagaca tattttccat accacctgct attattacgt cagcatctcc   3180
tgcttttata atttgtgctg ctaagctaac tgttctaagt cctgaaccac aaaccttatt   3240
aatagtcata gctggaattt caactggtaa tcctgcttta aaagatgcct gtcttgctgg   3300
attctgtcct aaacctgctt gaagaacatt tcctaaaatg acttcattaa catcctctgg   3360
ttttattcct gctttttttaa ctgcttcctt tatagctgta gctcctaaat ctactgctgg   3420
tacatcctta agagactttc cataagatcc aatcgctgtt cttactgcac tagctattac   3480
aacttctttc attctaacta acctcctaaa ttttgacccg gggatccac tagttctaga   3540
gcggccgcca ccgcggtgga gctccagctt ttgttccctt tagtgagggt taattgcgcg   3600
cttggcgtaa tcatggtcat agctgtttcc tgtgtgaaat tgttatccgc tcacaattcc   3660
acacaacata cgagccggaa gcataaagtg taaagcctgg ggtgcctaat gagtgagcta   3720
actcacatta attgcgttgc gctcactgcc cgctttccag tcgggaaacc tgtcgtgcca   3780
gctgcattaa tgaatcggcc aacgcgcggg gagaggcggt ttgcgtattg ggcgctcttc   3840
cgcttcctcg ctcactgact cgctgcgctc ggtcgttcgg ctgcggcgag cggtatcagc   3900
```

```
tcactcaaag gcggtaatac ggttatccac agaatcaggg gataacgcag gaaagaacat   3960
gtgagcaaaa ggccagcaaa aggccaggaa ccgtaaaaag gccgcgttgc tggcgttttt   4020
ccataggctc cgcccccctg acgagcatca caaaaatcga cgctcaagtc agaggtggcg   4080
aaacccgaca ggactataaa gataccaggc gtttccccct ggaagctccc tcgtgcgctc   4140
tcctgttccg accctgccgc ttaccggata cctgtccgcc tttctccctt cgggaagcgt   4200
ggcgctttct catagctcac gctgtaggta tctcagttcg gtgtaggtcg ttcgctccaa   4260
gctgggctgt gtgcacgaac cccccgttca gcccgaccgc tgcgccttat ccggtaacta   4320
tcgtcttgag tccaacccgg taagacacga cttatcgcca ctggcagcag ccactggtaa   4380
caggattagc agagcgaggt atgtaggcgg tgctacagag ttcttgaagt ggtggcctaa   4440
ctacggctac actagaagga cagtatttgg tatctgcgct ctgctgaagc cagttacctt   4500
cggaaaaaga gttggtagct cttgatccgg caaacaaacc accgctggta gcggtggttt   4560
ttttgtttgc aagcagcaga ttacgcgcag aaaaaaagga tctcaagaag atcctttgat   4620
cttttctacg gggtctgacg ctcagtggaa cgaaaactca cgttaaggga ttttggtcat   4680
gagattatca aaaaggatct tcacctagat ccttttaaat taaaaatgaa gttttaaatc   4740
aatctaaagt atatatgagt aaacttggtc tgacagttac caatgcttaa tcagtgaggc   4800
acctatctca gcgatctgtc tatttcgttc atccatagtt gcctgactcc ccgtcgtgta   4860
gataactacg atacgggagg gcttaccatc tggccccagt gctgcaatga taccgcgaga   4920
cccacgctca ccggctccag atttatcagc aataaaccag ccagccggaa gggccgagcg   4980
cagaagtggt cctgcaactt tatccgcctc catccagtct attaattgtt gccgggaagc   5040
tagagtaagt agttcgccag ttaatagttt gcgcaacgtt gttgccattg ctacaggcat   5100
cgtggtgtca cgctcgtcgt ttggtatggc ttcattcagc tccggttccc aacgatcaag   5160
gcgagttaca tgatccccca tgttgtgcaa aaaagcggtt agctccttcg gtcctccgat   5220
cgttgtcaga agtaagttgg ccgcagtgtt atcactcatg gttatggcag cactgcataa   5280
ttctcttact gtcatgccat ccgtaagatg cttttctgtg actggtgagt actcaaccaa   5340
gtcattctga gaatagtgta tgcggcgacc gagttgctct tgcccggcgt caatacggga   5400
taataccgcg ccacatagca gaactttaaa agtgctcatc attggaaaac gttcttcggg   5460
gcgaaaactc tcaaggatct taccgctgtt gagatccagt tcgatgtaac ccactcgtgc   5520
acccaactga tcttcagcat cttttacttt caccagcgtt tctgggtgag caaaaacagg   5580
aaggcaaaat gccgcaaaaa agggaataag ggcgacacgg aaatgttgaa tactcatact   5640
cttccttttt caatattatt gaagcattta tcagggttat tgtctcatga gcggatacat   5700
atttgaatgt atttagaaaa ataaacaaat aggggttccg cgcacatttc cccgaaaagt   5760
gccac                                                               5765
```

```
<210> SEQ ID NO 8
<211> LENGTH: 5919
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 8
```

```
ctgacgcgcc ctgtagcggc gcattaagcg cggcgggtgt ggtggttacg cgcagcgtga     60
ccgctacact tgccagcgcc ctagcgcccg ctcctttcgc tttcttccct tcctttctcg    120
```

-continued

```
ccacgttcgc cggctttccc cgtcaagctc taaatcgggg gctcccttta gggttccgat    180
ttagtgcttt acggcacctc gaccccaaaa aacttgatta gggtgatggt tcacgtagtg    240
ggccatcgcc ctgatagacg gtttttcgcc ctttgacgtt ggagtccacg ttctttaata    300
gtggactctt gttccaaact ggaacaacac tcaaccctat ctcggtctat tcttttgatt    360
tataagggat tttgccgatt tcggcctatt ggttaaaaaa tgagctgatt taacaaaaat    420
ttaacgcgaa ttttaacaaa atattaacgc ttacaatttc cattcgccat tcaggctgcg    480
caactgttgg gaagggcgat cggtgcgggc ctcttcgcta ttacgccagc tggcgaaagg    540
gggatgtgct gcaaggcgat taagttgggt aacgccaggg ttttcccagt cacgacgttg    600
taaaacgacg gccagtgagc gcgcgtaata cgactcacta tagggcgaat tggagctcca    660
ccgcggtggc ggccgctcta gaactagtgg atcccccggg ggttagcata tgcataagtt    720
taattttttt gttaaaaaat attaaacttt gtgttttttt taacaaaata tattgataaa    780
aataataata gtgggtataa ttaagttgtt agagaaaacg tataaattag ggataaacta    840
tggaacttat gaaatagatt gaaatggttt atctgttacc ccgtatcaaa atttaggagg    900
ttagttagaa tgaaagaagt tgtaatagct agtgcagtaa gaacagcgat tggatcttat    960
ggaaagtctc ttaaggatgt accagcagta gatttaggag ctacagctat aaaggaagca   1020
gttaaaaaag caggaataaa accagaggat gttaatgaag tcattttagg aaatgttctt   1080
caagcaggtt taggacagaa tccagcaaga caggcatctt ttaaagcagg attaccagtt   1140
gaaattccag ctatgactat taataaggtt tgtggttcag gacttagaac agttagctta   1200
gcagcacaaa ttataaaagc aggagatgct gacgtaataa tagcaggtgg tatggaaaat   1260
atgtctagag ctccttactt agcgaataac gctagatggg gatatagaat gggaaacgct   1320
aaatttgttg atgaaatgat cactgacgga ttgtgggatg catttaatga ttaccacatg   1380
ggaataacag cagaaaacat agctgagaga tggaacattt caagagaaga acaagatgag   1440
tttgctcttg catcacaaaa aaaagctgaa gaagctataa aatcaggtca atttaaagat   1500
gaaatagttc ctgtagtaat taaaggcaga aagggagaaa ctgtagttga tacagatgag   1560
caccctagat ttggatcaac tatagaagga cttgcaaaat taaaacctgc cttcaaaaaa   1620
gatggaacag ttacagctgg taatgcatca ggattaaatg actgtgcagc agtacttgta   1680
atcatgagtg cagaaaaagc taaagagctt ggagtaaaac cacttgctaa gatagtttct   1740
tatggttcag caggagttga cccagcaata atgggatatg gacctttcta tgcaacaaaa   1800
gcagctattg aaaaagcagg ttggacagtt gatgaattag atttaataga atcaaatgaa   1860
gcttttgcag ctcaaagttt agcagtagca aaagatttaa aatttgatat gaataaagta   1920
aatgtaaatg gaggagctat tgcccttggt catccaattg gagcatcagg tgcaagaata   1980
ctcgttactc ttgtacacgc aatgcaaaaa agagatgcaa aaaaaggctt agcaacttta   2040
tgtataggtg gcggacaagg aacagcaata ttgctagaaa agtgctagaa agtcgacctc   2100
gacggataac aatttcacac agaattcatt aaagaggaga aattaaccat gggccaactc   2160
ttcaaatcat ttgatgcgtc ggaaaaaaca cagctcatct gttttccgtt tgccggcggc   2220
tattcggcgt cgtttcgccc tctccatgct tttttgcagg gggagtgcga gatgctcgct   2280
gccgagccgc cgggacacgg cacgaatcaa acgtcagcca ttgaggatct cgaagagctg   2340
acggatttgt acaagcaaga actgaacctt cgccctgatc ggccgtttgt gctgttcgga   2400
cacagtatgg gcggaatgat caccttcagg ctggcgcaaa agcttgagcg tgaaggcatc   2460
```

```
tttccgcagg cggttatcat ttctgcaatc cagccgcctc atattcagcg gaagaaagtg   2520
tcccacctgc ctgatgatca gtttctcgat catattatcc aattaggcgg aatgcccgca   2580
gagcttgttg aaaataagga ggtcatgtcc tttttcctgc cttctttccg atcagattac   2640
cgggctcttg aacaatttga gctttacgat ctggcccaga tccagtcgcc tgttcatgtc   2700
tttaacgggc ttgatgataa aaaatgcata cgagatgcgg aagggtggaa gaagtgggca   2760
aaagacatca cattccatca atttgacggc gggcacatgt tcctgctgtc acaaacggaa   2820
gaagtcgcag aacggatttt tgcgatcttg aatcagcatc cgatcattca accgggatct   2880
catcaccatc accatcacta agcttaatta gctgagcttg gactcgagac gcgttacgta   2940
tccagattgg aaggtacctt ttatgttaaa ggatgaagta attaaacaaa ttagcacgcc   3000
attaacttcg cctgcatttc ctagaggacc ctataaattt cataatcgtg agtattttaa   3060
cattgtatat cgtacagata tggatgcact tcgtaaagtt gtgccagagc ctttagaaat   3120
tgatgagccc ttagtcaggt ttgaaattat ggcaatgcat gatacgagtg gacttggttg   3180
ttatacagaa agcggacagg ctattcccgt aagctttaat ggagttaagg gagattatct   3240
tcatatgatg tatttagata atgagcctgc aattgcagta ggaagggaat taagtgcata   3300
tcctaaaaag ctcgggtatc caaagctttt tgtggattca gatactttag taggaacttt   3360
agactatgga aaacttagag ttgcgacagc tacaatgggg tacaaacata aagccttaga   3420
tgctaatgaa gcaaaggatc aaatttgtcg ccctaattat atgttgaaaa taataccaa    3480
ttatgatgga agccctagaa tatgtgagct tataaatgcg aaaatcacag atgttaccgt   3540
acatgaagct tggacaggac caactcgact gcagttattt gatcacgcta tggcgccact   3600
taatgatttg ccagtaaaag agattgtttc tagctctcac attcttgcag atataatatt   3660
gcctagagct gaagttatat atgattatct taagtaatag aattcagggc ccggtaccca   3720
gcttttgttc cctttagtga gggttaattg cgcgcttggc gtaatcatgg tcatagctgt   3780
ttcctgtgtg aaattgttat ccgctcacaa ttccacacaa catacgagcc ggaagcataa   3840
agtgtaaagc ctggggtgcc taatgagtga gctaactcac attaattgcg ttgcgctcac   3900
tgcccgcttt ccagtcggga aacctgtcgt gccagctgca ttaatgaatc ggccaacgcg   3960
cggggagagg cggtttgcgt attgggcgct cttccgcttc ctcgctcact gactcgctgc   4020
gctcggtcgt tcggctgcgg cgagcggtat cagctcactc aaaggcggta atacggttat   4080
ccacagaatc aggggataac gcaggaaaga acatgtgagc aaaaggccag caaaaggcca   4140
ggaaccgtaa aaaggccgcg ttgctggcgt ttttccatag gctccgcccc cctgacgagc   4200
atcacaaaaa tcgacgctca agtcagaggt ggcgaaaccc gacaggacta taaagatacc   4260
aggcgtttcc ccctggaagc tccctcgtgc gctctcctgt tccgaccctg ccgcttaccg   4320
gatacctgtc cgcctttctc ccttcgggaa gcgtggcgct ttctcatagc tcacgctgta   4380
ggtatctcag ttcggtgtag gtcgttcgct ccaagctggg ctgtgtgcac gaaccccccg   4440
ttcagcccga ccgctgcgcc ttatccggta actatcgtct tgagtccaac ccggtaagac   4500
acgacttatc gccactggca gcagccactg gtaacaggat tagcagagcg aggtatgtag   4560
gcggtgctac agagttcttg aagtggtggc ctaactacgg ctacactaga aggacagtat   4620
ttggtatctg cgctctgctg aagccagtta ccttcggaaa aagagttggt agctcttgat   4680
ccggcaaaca aaccaccgct ggtagcggtg gtttttttgt ttgcaagcag cagattacgc   4740
gcagaaaaaa aggatctcaa gaagatcctt tgatcttttc tacggggtct gacgctcagt   4800
ggaacgaaaa ctcacgttaa gggattttgg tcatgagatt atcaaaaagg atcttcacct   4860
```

```
agatcctttt aaattaaaaa tgaagtttta aatcaatcta aagtatatat gagtaaactt   4920

ggtctgacag ttaccaatgc ttaatcagtg aggcacctat ctcagcgatc tgtctatttc   4980

gttcatccat agttgcctga ctccccgtcg tgtagataac tacgatacgg gagggcttac   5040

catctggccc cagtgctgca atgataccgc gagacccacg ctcaccggct ccagatttat   5100

cagcaataaa ccagccagcc ggaagggccg agcgcagaag tggtcctgca actttatccg   5160

cctccatcca gtctattaat tgttgccggg aagctagagt aagtagttcg ccagttaata   5220

gtttgcgcaa cgttgttgcc attgctacag gcatcgtggt gtcacgctcg tcgtttggta   5280

tggcttcatt cagctccggt tcccaacgat caaggcgagt tacatgatcc cccatgttgt   5340

gcaaaaaagc ggttagctcc ttcggtcctc cgatcgttgt cagaagtaag ttggccgcag   5400

tgttatcact catggttatg gcagcactgc ataattctct tactgtcatg ccatccgtaa   5460

gatgcttttc tgtgactggt gagtactcaa ccaagtcatt ctgagaatag tgtatgcggc   5520

gaccgagttg ctcttgcccg gcgtcaatac gggataatac cgcgccacat agcagaactt   5580

taaaagtgct catcattgga aaacgttctt cggggcgaaa actctcaagg atcttaccgc   5640

tgttgagatc cagttcgatg taacccactc gtgcacccaa ctgatcttca gcatctttta   5700

ctttcaccag cgtttctggg tgagcaaaaa caggaaggca aaatgccgca aaaaagggaa   5760

taagggcgac acggaaatgt tgaatactca tactcttcct ttttcaatat tattgaagca   5820

tttatcaggg ttattgtctc atgagcggat acatatttga atgtatttag aaaaataaac   5880

aaataggggt tccgcgcaca tttccccgaa aagtgccac                          5919
```

<210> SEQ ID NO 9
<211> LENGTH: 5409
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 9

```
tcgcgcgttt cggtgatgac ggtgaaaacc tctgacacat gcagctcccg gagacggtca     60

cagcttgtct gtaagcggat gccgggagca gacaagcccg tcagggcgcg tcagcgggtg    120

ttggcgggtg tcggggctgg cttaactatg cggcatcaga gcagattgta ctgagagtgc    180

accatatgcg gtgtgaaata ccgcacagat gcgtaaggag aaaataccgc atcaggcgcc    240

attcgccatt caggctgcgc aactgttggg aagggcgatc ggtgcgggcc tcttcgctat    300

tacgccagct ggcgaaaggg ggatgtgctg caaggcgatt aagttgggta acgccagggt    360

tttcccagtc acgacgttgt aaaacgacgg ccagtgaatt caggtaactc ttatttttat    420

tacttaagat aatcatatat aacttcagct ctaggcaata ttatatctgc aagaatgtga    480

gagctagaaa caatctcttt tactggcaaa tcattaagtg gcgccatagc gtgatcaaat    540

aactgcagtc gagttggtcc tgtccaagct tcatgtacgg taacatctgt gattttcgca    600

tttataagct cacatattct agggcttcca tcataattgg gtattatttt caacatataa    660

ttagggcgac aaatttgatc ctttgcttca ttagcatcta aggctttatg tttgtacccc    720

attgtagctg tcgcaactct aagttttcca tagtctaaag ttcctactaa agtatctgaa    780

tccacaaaaa gctttggata cccgagcttt ttaggatatg cacttaattc ccttcctact    840

gcaattgcag gctcattatc taaatacatc atatgaagat aatctccctt aactccatta    900

aagcttacgg gaatagcctg tccgctttct gtataacaac caagtccact cgtatcatgc    960
```

```
attgccataa tttcaaacct gactaagggc tcatcaattt ctaaaggctc tggcacaact   1020
ttacgaagtg catccatatc tgtacgatat acaatgttaa aatactcacg attatgaaat   1080
ttatagggtc ctctaggaaa tgcaggcgaa gttaatggcg tgctaatttg tttaattact   1140
tcatccttta acataaaagg tacccggtta aatgatcgga tgctgattca agatcgcaaa   1200
aatccgttct gcgacttctt ccgtttgtga cagcaggaac atgtgcccgc cgtcaaattg   1260
atggaatgtg atgtcttttg cccacttctt ccacccttcc gcatctcgta tgcatttttt   1320
atcatcaagc ccgttaaaga catgaacagg cgactggatc tgggccagat cgtaaagctc   1380
aaattgttca agagcccggt aatctgatcg gaaagaaggc aggaaaaagg acatgacctc   1440
cttattttca acaagctctg cgggcattcc gcctaattgg ataatatgat cgagaaactg   1500
atcatcaggc aggtgggaca ctttcctccg ctgaatatga ggcggctgga ttgcagaaat   1560
gataaccgcc tgcggaaaga tgccttcacg ctcaagcttt tgcgccagcc tgaaggtgat   1620
cattccgccc atactgtgtc cgaacagcac aaacggccga tcagggcgaa ggttcagttc   1680
ttgcttgtac aaatccgtca gctcttcgag atcctcaatg gctgacgttt gattcgtgcc   1740
gtgtcccggc ggctcggcag cgagcatctc gcactccccc tgcaaaaaag catggagagg   1800
gcgaaacgac gccgaatagc cgccggcaaa cggaaaacag atgagcggtg tttttttccga   1860
cgcatcaaat gatttgaaga gttggcccat ggttaatttc tcctctttaa tgaattctgt   1920
gtgaaattgt tatcggatcc tttctagcac ttttctagca atattgctgt tccttgtccg   1980
ccacctatac ataaagttgc taagcctttt tttgcatctc ttttttgcat tgcgtgtaca   2040
agagtaacga gtattcttgc acctgatgct ccaattggat gaccaagggc aatagctcct   2100
ccatttacat ttactttatt catatcaaat tttaaatctt ttgctactgc taaactttga   2160
gctgcaaaag cttcatttga ttctattaaa tctaattcat caactgtcca acctgctttt   2220
tcaatagctg cttttgttgc atagaaaggt ccatatccca ttattgctgg gtcaactcct   2280
gctgaaccat aagaaactat cttagcaagt ggttttactc caagctcttt agctttttct   2340
gcactcatga ttacaagtac tgctgcacag tcatttaatc ctgatgcatt accagctgta   2400
actgttccat ctttttgaa ggcaggtttt aattttgcaa gtccttctat agttgatcca   2460
aatctagggt gctcatctgt atcaactaca gtttctccct ttctgccttt aattactaca   2520
ggaactattt catctttaaa ttgacctgat tttatagctt cttcagcttt tttttgtgat   2580
gcaagagcaa actcatcttg ttcttctctt gaaatgttcc atctctcagc tatgttttct   2640
gctgttattc ccatgtggta atcattaaat gcatcccaca atccgtcagt gatcatttca   2700
tcaacaaatt tagcgtttcc cattctatat ccccatctag cgttattcgc taagtaagga   2760
gctctagaca tattttccat accacctgct attattacgt cagcatctcc tgcttttata   2820
atttgtgctg ctaagctaac tgttctaagt cctgaaccac aaaccttatt aatagtcata   2880
gctggaattt caactggtaa tcctgcttta aaagatgcct gtcttgctgg attctgtcct   2940
aaacctgctt gaagaacatt tcctaaaatg acttcattaa catcctctgg ttttattcct   3000
gcttttttaa ctgcttcctt tatagctgta gctcctaaat ctactgctgg tacatcctta   3060
agagactttc cataagatcc aatcgctgtt cttactgcac tagctattac aacttctttc   3120
attctaacta acctcctaaa ttttgatacg ggtcgacctg caggcatgca agcttggcgt   3180
aatcatggtc atagctgttt cctgtgtgaa attgttatcc gctcacaatt ccacacaaca   3240
tacgagccgg aagcataaag tgtaaagcct ggggtgccta atgagtgagc taactcacat   3300
```

```
taattgcgtt gcgctcactg cccgctttcc agtcgggaaa cctgtcgtgc cagctgcatt   3360
aatgaatcgg ccaacgcgcg gggagaggcg gtttgcgtat tgggcgctct tccgcttcct   3420
cgctcactga ctcgctgcgc tcggtcgttc ggctgcggcg agcggtatca gctcactcaa   3480
aggcggtaat acggttatcc acagaatcag gggataacgc aggaaagaac atgtgagcaa   3540
aaggccagca aaaggccagg aaccgtaaaa aggccgcgtt gctggcgttt ttccataggc   3600
tccgcccccc tgacgagcat cacaaaaatc gacgctcaag tcagaggtgg cgaaacccga   3660
caggactata aagataccag gcgtttcccc ctggaagctc cctcgtgcgc tctcctgttc   3720
cgaccctgcc gcttaccgga tacctgtccg cctttctccc ttcgggaagc gtggcgcttt   3780
ctcatagctc acgctgtagg tatctcagtt cggtgtaggt cgttcgctcc aagctgggct   3840
gtgtgcacga accccccgtt cagcccgacc gctgcgcctt atccggtaac tatcgtcttg   3900
agtccaaccc ggtaagacac gacttatcgc cactggcagc agccactggt aacaggatta   3960
gcagagcgag gtatgtaggc ggtgctacag agttcttgaa gtggtggcct aactacggct   4020
acactagaag gacagtattt ggtatctgcg ctctgctgaa gccagttacc ttcggaaaaa   4080
gagttggtag ctcttgatcc ggcaaacaaa ccaccgctgg tagcggtggt ttttttgttt   4140
gcaagcagca gattacgcgc agaaaaaaag gatctcaaga agatcctttg atcttttcta   4200
cggggtctga cgctcagtgg aacgaaaact cacgttaagg gattttggtc atgagattat   4260
caaaaaggat cttcacctag atccttttaa attaaaaatg aagttttaaa tcaatctaaa   4320
gtatatatga gtaaacttgg tctgacagtt accaatgctt aatcagtgag gcacctatct   4380
cagcgatctg tctatttcgt tcatccatag ttgcctgact ccccgtcgtg tagataacta   4440
cgatacggga gggcttacca tctggcccca gtgctgcaat gataccgcga gacccacgct   4500
caccggctcc agatttatca gcaataaacc agccagccgg aagggccgag cgcagaagtg   4560
gtcctgcaac tttatccgcc tccatccagt ctattaattg ttgccgggaa gctagagtaa   4620
gtagttcgcc agttaatagt ttgcgcaacg ttgttgccat tgctacaggc atcgtggtgt   4680
cacgctcgtc gtttggtatg gcttcattca gctccggttc ccaacgatca aggcgagtta   4740
catgatcccc catgttgtgc aaaaaagcgg ttagctcctt cggtcctccg atcgttgtca   4800
gaagtaagtt ggccgcagtg ttatcactca tggttatggc agcactgcat aattctctta   4860
ctgtcatgcc atccgtaaga tgcttttctg tgactggtga gtactcaacc aagtcattct   4920
gagaatagtg tatgcggcga ccgagttgct cttgcccggc gtcaatacgg gataataccg   4980
cgccacatag cagaacttta aaagtgctca tcattggaaa acgttcttcg gggcgaaaac   5040
tctcaaggat cttaccgctg ttgagatcca gttcgatgta acccactcgt gcacccaact   5100
gatcttcagc atcttttact ttcaccagcg tttctgggtg agcaaaaaca ggaaggcaaa   5160
atgccgcaaa aaagggaata agggcgacac ggaaatgttg aatactcata ctcttccttt   5220
ttcaatatta ttgaagcatt tatcagggtt attgtctcat gagcggatac atatttgaat   5280
gtatttagaa aaataaacaa ataggggttc cgcgcacatt tccccgaaaa gtgccacctg   5340
acgtctaaga aaccattatt atcatgacat taacctataa aaataggcgt atcacgaggc   5400
cctttcgtc                                                           5409
```

<210> SEQ ID NO 10
<211> LENGTH: 5589
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 10

```
tcgcgcgttt cggtgatgac ggtgaaaacc tctgacacat gcagctcccg gagacggtca     60
cagcttgtct gtaagcggat gccgggagca gacaagcccg tcagggcgcg tcagcgggtg    120
ttggcgggtg tcggggctgg cttaactatg cggcatcaga gcagattgta ctgagagtgc    180
accatatgcg gtgtgaaata ccgcacagat gcgtaaggag aaaataccgc atcaggcgcc    240
attcgccatt caggctgcgc aactgttggg aagggcgatc ggtgcgggcc tcttcgctat    300
tacgccagct ggcgaaaggg ggatgtgctg caaggcgatt aagttgggta acgccagggt    360
tttcccagtc acgacgttgt aaaacgacgg ccagtgccaa gcttgcatgc ctgcaggtcg    420
acggttagca tatgcataag tttaattttt ttgttaaaaa atattaaact ttgtgttttt    480
tttaacaaaa tatattgata aaaataataa tagtgggtat aattaagttg ttagagaaaa    540
cgtataaatt agggataaac tatggaactt atgaaataga ttgaaatggt ttatctgtta    600
ccccgtatca aaatttagga ggttagttag aatgaaagaa gttgtaatag ctagtgcagt    660
aagaacagcg attggatctt atggaaagtc tcttaaggat gtaccagcag tagatttagg    720
agctacagct ataaaggaag cagttaaaaa agcaggaata aaaccagagg atgttaatga    780
agtcatttta ggaaatgttc ttcaagcagg tttaggacag aatccagcaa gacaggcatc    840
ttttaaagca ggattaccag ttgaaattcc agctatgact attaataagg tttgtggttc    900
aggacttaga acagttagct tagcagcaca aattataaaa gcaggagatg ctgacgtaat    960
aatagcaggt ggtatggaaa atatgtctag agctccttac ttagcgaata acgctagatg   1020
ggatatagaa atgggaaacg ctaaatttgt tgatgaaatg atcactgacg gattgtggga   1080
tgcatttaat gattaccaca tgggaataac agcagaaaac atagctgaga gatggaacat   1140
ttcaagagaa gaacaagatg agtttgctct tgcatcacaa aaaaaagctg aagaagctat   1200
aaaatcaggt caatttaaag atgaaatagt tcctgtagta attaaaggca gaaagggaga   1260
aactgtagtt gatacagatg agcaccctag atttggatca actatagaag gacttgcaaa   1320
attaaaacct gccttcaaaa aagatggaac agttacagct ggtaatgcat caggattaaa   1380
tgactgtgca gcagtacttg taatcatgag tgcagaaaaa gctaaagagc ttggagtaaa   1440
accacttgct aagatagttt cttatggttc agcaggagtt gacccagcaa taatgggata   1500
tggacctttc tatgcaacaa aagcagctat tgaaaaagca ggttggacag ttgatgaatt   1560
agatttaata gaatcaaatg aagcttttgc agctcaaagt ttagcagtag caaaagattt   1620
aaaatttgat atgaataaag taaatgtaaa tggaggagct attgcccttg gtcatccaat   1680
tggagcatca ggtgcaagaa tactcgttac tcttgtacac gcaatgcaaa aaagagatgc   1740
aaaaaaaggc ttagcaactt tatgtatagg tggcggacaa ggaacagcaa tattgctaga   1800
aaagtgctag aaaggatccg ataacaattt cacacagaat tcattaaaga ggagaaatta   1860
accatgggcc aactcttcaa atcatttgat gcgtcggaaa aacacagct  catctgtttt   1920
ccgtttgccg gcggctattc ggcgtcgttt cgccctctcc atgctttttt gcagggggag   1980
tgcgagatgc tcgctgccga gccgccggga cacggcacga atcaaacgtc agccattgag   2040
gatctcgaag agctgacgga tttgtacaag caagaactga accttcgccc tgatcggccg   2100
tttgtgctgt tcggacacag tatgggcgga atgatcacct tcaggctggc gcaaaagctt   2160
gagcgtgaag gcatctttcc gcaggcggtt atcatttctg caatccagcc gcctcatatt   2220
cagcggaaga aagtgtccca cctgcctgat gatcagtttc tcgatcatat tatccaatta   2280
```

-continued

```
ggcggaatgc ccgcagagct tgttgaaaat aaggaggtca tgtccttttt cctgccttct   2340
ttccgatcag attaccgggc tcttgaacaa tttgagcttt acgatctggc ccagatccag   2400
tcgcctgttc atgtctttaa cgggcttgat gataaaaaat gcatacgaga tgcggaaggg   2460
tggaagaagt gggcaaaaga catcacattc catcaatttg acggcgggca catgttcctg   2520
ctgtcacaaa cggaagaagt cgcagaacgg atttttgcga tcttgaatca gcatccgatc   2580
atttaaccgg gtacctttta tgttaaagga tgaagtaatt aaacaaatta gcacgccatt   2640
aacttcgcct gcatttccta gaggacccta taaatttcat aatcgtgagt attttaacat   2700
tgtatatcgt acagatatgg atgcacttcg taaagttgtg ccagagcctt tagaaattga   2760
tgagccctta gtcaggtttg aaattatggc aatgcatgat acgagtggac ttggttgtta   2820
tacagaaagc ggacaggcta ttcccgtaag ctttaatgga gttaagggag attatcttca   2880
tatgatgtat ttagataatg agcctgcaat tgcagtagga agggaattaa gtgcatatcc   2940
taaaaagctc gggtatccaa agctttttgt ggattcagat actttagtag gaactttaga   3000
ctatggaaaa cttagagttg cgacagctac aatggggtac aaacataaag ccttagatgc   3060
taatgaagca aaggatcaaa tttgtcgccc taattatatg ttgaaaataa tacccaatta   3120
tgatggaagc cctagaatat gtgagcttat aaatgcgaaa atcacagatg ttaccgtaca   3180
tgaagcttgg acaggaccaa ctcgactgca gttatttgat cacgctatgg cgccacttaa   3240
tgatttgcca gtaaaagaga ttgtttctag ctctcacatt cttgcagata taatattgcc   3300
tagagctgaa gttatatatg attatcttaa gtaataaaaa taagagttac ctgaattcgt   3360
aatcatggtc atagctgttt cctgtgtgaa attgttatcc gctcacaatt ccacacaaca   3420
tacgagccgg aagcataaag tgtaaagcct ggggtgccta atgagtgagc taactcacat   3480
taattgcgtt gcgctcactg cccgctttcc agtcgggaaa cctgtcgtgc cagctgcatt   3540
aatgaatcgg ccaacgcgcg gggagaggcg gtttgcgtat tgggcgctct tccgcttcct   3600
cgctcactga ctcgctgcgc tcggtcgttc ggctgcggcg agcggtatca gctcactcaa   3660
aggcggtaat acggttatcc acagaatcag gggataacgc aggaaagaac atgtgagcaa   3720
aaggccagca aaaggccagg aaccgtaaaa aggccgcgtt gctggcgttt ttccataggc   3780
tccgcccccc tgacgagcat cacaaaaatc gacgctcaag tcagaggtgg cgaaacccga   3840
caggactata aagataccag gcgtttcccc ctggaagctc cctcgtgcgc tctcctgttc   3900
cgaccctgcc gcttaccgga tacctgtccg cctttctccc ttcgggaagc gtggcgcttt   3960
ctcatagctc acgctgtagg tatctcagtt cggtgtaggt cgttcgctcc aagctgggct   4020
gtgtgcacga accccccgtt cagcccgacc gctgcgcctt atccggtaac tatcgtcttg   4080
agtccaaccc ggtaagacac gacttatcgc cactggcagc agccactggt aacaggatta   4140
gcagagcgag gtatgtaggc ggtgctacag agttcttgaa gtggtggcct aactacggct   4200
acactagaag gacagtattt ggtatctgcg ctctgctgaa gccagttacc ttcggaaaaa   4260
gagttggtag ctcttgatcc ggcaaacaaa ccaccgctgg tagcggtggt ttttttgttt   4320
gcaagcagca gattacgcgc agaaaaaaag gatctcaaga agatcctttg atcttttcta   4380
cggggtctga cgctcagtgg aacgaaaact cacgttaagg gattttggtc atgagattat   4440
caaaaaggat cttcacctag atccttttaa attaaaaatg aagttttaaa tcaatctaaa   4500
gtatatatga gtaaacttgg tctgacagtt accaatgctt aatcagtgag gcacctatct   4560
cagcgatctg tctatttcgt tcatccatag ttgcctgact ccccgtcgtg tagataacta   4620
```

```
cgatacggga gggcttacca tctggcccca gtgctgcaat gataccgcga gacccacgct   4680

caccggctcc agatttatca gcaataaacc agccagccgg aagggccgag cgcagaagtg   4740

gtcctgcaac tttatccgcc tccatccagt ctattaattg ttgccgggaa gctagagtaa   4800

gtagttcgcc agttaatagt ttgcgcaacg ttgttgccat tgctacaggc atcgtggtgt   4860

cacgctcgtc gtttggtatg gcttcattca gctccggttc ccaacgatca aggcgagtta   4920

catgatcccc catgttgtgc aaaaaagcgg ttagctcctt cggtcctccg atcgttgtca   4980

gaagtaagtt ggccgcagtg ttatcactca tggttatggc agcactgcat aattctctta   5040

ctgtcatgcc atccgtaaga tgcttttctg tgactggtga gtactcaacc aagtcattct   5100

gagaatagtg tatgcggcga ccgagttgct cttgcccggc gtcaatacgg gataataccg   5160

cgccacatag cagaacttta aaagtgctca tcattggaaa acgttcttcg gggcgaaaac   5220

tctcaaggat cttaccgctg ttgagatcca gttcgatgta acccactcgt gcacccaact   5280

gatcttcagc atcttttact ttcaccagcg tttctgggtg agcaaaaaca ggaaggcaaa   5340

atgccgcaaa aaagggaata agggcgacac ggaaatgttg aatactcata ctcttccttt   5400

ttcaatatta ttgaagcatt tatcagggtt attgtctcat gagcggatac atatttgaat   5460

gtatttagaa aaataaacaa ataggggttc cgcgcacatt tccccgaaaa gtgccacctg   5520

acgtctaaga aaccattatt atcatgacat taacctataa aaataggcgt atcacgaggc   5580

cctttcgtc                                                           5589
```

<210> SEQ ID NO 11
<211> LENGTH: 5098
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 11

```
tcgcgcgttt cggtgatgac ggtgaaaacc tctgacacat gcagctcccg gagacggtca     60

cagcttgtct gtaagcggat gccgggagca gacaagcccg tcagggcgcg tcagcgggtg    120

ttggcgggtg tcggggctgg cttaactatg cggcatcaga gcagattgta ctgagagtgc    180

accatatgcg gtgtgaaata ccgcacagat gcgtaaggag aaaataccgc atcaggcgcc    240

attcgccatt caggctgcgc aactgttggg aagggcgatc ggtgcgggcc tcttcgctat    300

tacgccagct ggcgaaaggg ggatgtgctg caaggcgatt aagttgggta acgccagggt    360

tttcccagtc acgacgttgt aaaacgacgg ccagtgaatt caggtaactc ttatttttat    420

tacttaagat aatcatatat aacttcagct ctaggcaata ttatatctgc aagaatgtga    480

gagctagaaa caatctcttt tactggcaaa tcattaagtg gcgccatagc gtgatcaaat    540

aactgcagtc gagttggtcc tgtccaagct tcatgtacgg taacatctgt gattttcgca    600

tttataagct cacatattct agggcttcca tcataattgg gtattatttt caacatataa    660

ttagggcgac aaatttgatc ctttgcttca ttagcatcta aggctttatg tttgtacccc    720

attgtagctg tcgcaactct aagttttcca tagtctaaag ttcctactaa agtatctgaa    780

tccacaaaaa gctttggata cccgagcttt ttaggatatg cacttaattc ccttcctact    840

gcaattgcag gctcattatc taaatacatc atatgaagat aatctccctt aactccatta    900

aagcttacgg gaatagcctg tccgctttct gtataacaac caagtccact cgtatcatgc    960

attgccataa tttcaaacct gactaagggc tcatcaattt ctaaaggctc tggcacaact   1020
```

```
ttacgaagtg catccatatc tgtacgatat acaatgttaa aatactcacg attatgaaat   1080
ttatagggtc ctctaggaaa tgcaggcgaa gttaatggcg tgctaatttg tttaattact   1140
tcatccttta acataaaagg tacctcattg catactccga aaaattattt taagtgatga   1200
aacgccgctt taacttcttt gggaaacgcc actggtttca tcttgcctag atcaacacag   1260
gctaccttaa cagtagcctt tgataacatc agggtgttgc gcatcagtct ctgttcaaaa   1320
aggattgtag ccccttttac ttctgaaacc tctgtttcca ccataagtaa atcatccaat   1380
tttgctgcca cgcaataatc aatggcgagc gttttgacaa caaatgcgag ttgttgttcc   1440
tctagtaagg tttgttgcgt aaaatttaat gtacgcaaat attctgttct tgctcgttca   1500
aaaaaatgca aatagcgagc gtgatacact acgccacctg catcagtatc ttcataatac   1560
acacgaacag gaaaagaaaa gccattatcc aacatatgta tatctccttc ttaaagttaa   1620
acaggatcct ttctagcact tttctagcaa tattgctgtt ccttgtccgc cacctataca   1680
taaagttgct aagccttttt ttgcatctct tttttgcatt gcgtgtacaa gagtaacgag   1740
tattcttgca cctgatgctc caattggatg accaagggca atagctcctc catttacatt   1800
tactttattc atatcaaatt ttaaatcttt tgctactgct aaactttgag ctgcaaaagc   1860
ttcatttgat tctattaaat ctaattcatc aactgtccaa cctgcttttt caatagctgc   1920
ttttgttgca tagaaaggtc catatcccat tattgctggg tcaactcctg ctgaaccata   1980
agaaactatc ttagcaagtg gttttactcc aagctcttta gctttttctg cactcatgat   2040
tacaagtact gctgcacagt catttaatcc tgatgcatta ccagctgtaa ctgttccatc   2100
tttttgaag gcaggtttta attttgcaag tccttctata gttgatccaa atctagggtg   2160
ctcatctgta tcaactacag tttctccctt tctgccttta attactacag gaactatttc   2220
atctttaaat tgacctgatt ttatagcttc ttcagctttt ttttgtgatg caagagcaaa   2280
ctcatcttgt tcttctcttg aaatgttcca tctctcagct atgttttctg ctgttattcc   2340
catgtggtaa tcattaaatg catcccacaa tccgtcagtg atcatttcat caacaaattt   2400
agcgtttccc attctatatc cccatctagc gttattcgct aagtaaggag ctctagacat   2460
attttccata ccacctgcta ttattacgtc agcatctcct gcttttataa tttgtgctgc   2520
taagctaact gttctaagtc ctgaaccaca aaccttatta atagtcatag ctggaatttc   2580
aactggtaat cctgctttaa aagatgcctg tcttgctgga ttctgtccta aacctgcttg   2640
aagaacattt cctaaaatga cttcattaac atcctctggt tttattcctg cttttttaac   2700
tgcttccttt atagctgtag ctcctaaatc tactgctggt acatccttaa gagactttcc   2760
ataagatcca atcgctgttc ttactgcact agctattaca acttctttca ttctaactaa   2820
cctcctaaat tttgatacgg gtcgacctgc aggcatgcaa gcttggcgta atcatggtca   2880
tagctgtttc ctgtgtgaaa ttgttatccg ctcacaattc cacacaacat acgagccgga   2940
agcataaagt gtaaagcctg gggtgcctaa tgagtgagct aactcacatt aattgcgttg   3000
cgctcactgc ccgctttcca gtcgggaaac ctgtcgtgcc agctgcatta atgaatcggc   3060
caacgcgcgg ggagaggcgg tttgcgtatt gggcgctctt ccgcttcctc gctcactgac   3120
tcgctgcgct cggtcgttcg gctgcggcga gcggtatcag ctcactcaaa ggcggtaata   3180
cggttatcca cagaatcagg ggataacgca ggaaagaaca tgtgagcaaa aggccagcaa   3240
aaggccagga accgtaaaaa ggccgcgttg ctggcgtttt tccataggct ccgcccccct   3300
gacgagcatc acaaaaatcg acgctcaagt cagaggtggc gaaacccgac aggactataa   3360
agataccagg cgtttccccc tggaagctcc ctcgtgcgct ctcctgttcc gaccctgccg   3420
```

```
cttaccggat acctgtccgc ctttctccct tcgggaagcg tggcgctttc tcatagctca   3480

cgctgtaggt atctcagttc ggtgtaggtc gttcgctcca agctgggctg tgtgcacgaa   3540

ccccccgttc agcccgaccg ctgcgcctta tccggtaact atcgtcttga gtccaacccg   3600

gtaagacacg acttatcgcc actggcagca gccactggta acaggattag cagagcgagg   3660

tatgtaggcg gtgctacaga gttcttgaag tggtggccta actacggcta cactagaagg   3720

acagtatttg gtatctgcgc tctgctgaag ccagttacct tcggaaaaag agttggtagc   3780

tcttgatccg gcaaacaaac caccgctggt agcggtggtt tttttgtttg caagcagcag   3840

attacgcgca gaaaaaaagg atctcaagaa gatcctttga tcttttctac ggggtctgac   3900

gctcagtgga acgaaaactc acgttaaggg attttggtca tgagattatc aaaaaggatc   3960

ttcacctaga tccttttaaa ttaaaaatga agttttaaat caatctaaag tatatatgag   4020

taaacttggt ctgacagtta ccaatgctta atcagtgagg cacctatctc agcgatctgt   4080

ctatttcgtt catccatagt tgcctgactc cccgtcgtgt agataactac gatacgggag   4140

ggcttaccat ctggccccag tgctgcaatg ataccgcgag acccacgctc accggctcca   4200

gatttatcag caataaacca gccagccgga agggccgagc gcagaagtgg tcctgcaact   4260

ttatccgcct ccatccagtc tattaattgt tgccgggaag ctagagtaag tagttcgcca   4320

gttaatagtt tgcgcaacgt tgttgccatt gctacaggca tcgtggtgtc acgctcgtcg   4380

tttggtatgg cttcattcag ctccggttcc caacgatcaa ggcgagttac atgatccccc   4440

atgttgtgca aaaaagcggt tagctccttc ggtcctccga tcgttgtcag aagtaagttg   4500

gccgcagtgt tatcactcat ggttatggca gcactgcata attctcttac tgtcatgcca   4560

tccgtaagat gcttttctgt gactggtgag tactcaacca agtcattctg agaatagtgt   4620

atgcggcgac cgagttgctc ttgcccggcg tcaatacggg ataataccgc gccacatagc   4680

agaactttaa aagtgctcat cattggaaaa cgttcttcgg ggcgaaaact ctcaaggatc   4740

ttaccgctgt tgagatccag ttcgatgtaa cccactcgtg cacccaactg atcttcagca   4800

tcttttactt tcaccagcgt ttctgggtga gcaaaaacag gaaggcaaaa tgccgcaaaa   4860

aagggaataa gggcgacacg gaaatgttga atactcatac tcttcctttt tcaatattat   4920

tgaagcattt atcagggtta ttgtctcatg agcggataca tatttgaatg tatttagaaa   4980

aataaacaaa taggggttcc gcgcacattt ccccgaaaag tgccacctga cgtctaagaa   5040

accattatta tcatgacatt aacctataaa aataggcgta tcacgaggcc ctttcgtc     5098
```

```
<210> SEQ ID NO 12
<211> LENGTH: 5964
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 12

tcgcgcgttt cggtgatgac ggtgaaaacc tctgacacat gcagctcccg gagacggtca     60

cagcttgtct gtaagcggat gccgggagca gacaagcccg tcagggcgcg tcagcgggtg    120

ttggcgggtg tcggggctgg cttaactatg cggcatcaga gcagattgta ctgagagtgc    180

accatatgcg gtgtgaaata ccgcacagat gcgtaaggag aaaataccgc atcaggcgcc    240

attcgccatt caggctgcgc aactgttggg aagggcgatc ggtgcgggcc tcttcgctat    300

tacgccagct ggcgaaaggg ggatgtgctg caaggcgatt aagttgggta acgccagggt    360
```

tttcccagtc acgacgttgt aaaacgacgg ccagtgaatt caggtaactc ttatttttat 420
tacttaagat aatcatatat aacttcagct ctaggcaata ttatatctgc aagaatgtga 480
gagctagaaa caatctcttt tactggcaaa tcattaagtg gcgccatagc gtgatcaaat 540
aactgcagtc gagttggtcc tgtccaagct tcatgtacgg taacatctgt gattttcgca 600
tttataagct cacatattct agggcttcca tcataattgg gtattatttt caacatataa 660
ttagggcgac aaatttgatc ctttgcttca ttagcatcta aggctttatg tttgtacccc 720
attgtagctg tcgcaactct aagttttcca tagtctaaag ttcctactaa agtatctgaa 780
tccacaaaaa gctttggata cccgagcttt ttaggatatg cacttaattc ccttcctact 840
gcaattgcag gctcattatc taaatacatc atatgaagat aatctccctt aactccatta 900
aagcttacgg gaatagcctg tccgctttct gtataacaac caagtccact cgtatcatgc 960
attgccataa tttcaaacct gactaagggc tcatcaattt ctaaaggctc tggcacaact 1020
ttacgaagtg catccatatc tgtacgatat acaatgttaa aatactcacg attatgaaat 1080
ttatagggtc ctctaggaaa tgcaggcgaa gttaatggcg tgctaatttg tttaattact 1140
tcatccttta acataaaagg tacctaaaca gccatgggtc taagttcatt ggatatgagt 1200
aaatctgcag cagttaaaga ccttatttca tcaatggttg tgtttttatt aatttcagtg 1260
agaagtaaac catcattaat aacctcaatt actccaagtt ctgttacaat tagatttgct 1320
tgagactttg ccgtgagggg aagtgtacat ttttttaaaa ttttaggttg acctttattt 1380
gtatgtctca ttgcaattat tactttctta gctccattta ctaaatccat agctccaccc 1440
ataccagaga gcatttttcc aggaacaatc caattggcta tattaccctt ttcatctacc 1500
tggagagccc ctaaaacagt aacatctacg tgaccaccac ggattagtga aaacgaaact 1560
gagctatcga aaaatgtgcc gtcaggaagt actgttgtat agtctcctcc tgcatttact 1620
acatctttat ctgcctcatt tattttagga ctagcgccca ttccaactat tccgttttct 1680
gattggaaag taattttgaa attttttggt atataatctg caaccatggt aggaagacct 1740
acacctaagt ttacaagttg accatttttt aattctcttg caactctttt ggctattatt 1800
tctttcgcta ggtttttatc attaatcatt ttatgcaggc tcctttacta tataatttat 1860
aagaactccg gggtcattgg ctttttcctt ttctagtttt tcacagctaa ctaaattttc 1920
agcttcaact attacggttt tagctgccat tgccatatag ggattaaagt ttttagtagt 1980
acctttatag aaggtgtttc cggcctcatc tacaatacta cctttaatta atgctacatc 2040
ggctgtaaga ggtagctcta acaaatattc cgttccattt atagatattt ttttctttcc 2100
tttttcaatc aaagttccta aacctgtttt agttagtaca ccacctaagc cagatccgcc 2160
tgcacgtatt ctttccacta gagttccttg gggagagagc tctacttcaa gttcattatt 2220
aaaaagtttt ttgccagtat ctgggttgct gcctatatat gaagcaataa gctttttttac 2280 ttgattattt gatattaact taccaatacc tgtattagga taacatgtat cattacttat 2340
aatcgttaaa ttctttatat ttaaattaac taaaaaatca attaatttgg ttggagtgcc 2400
acagtttaaa aaacctccaa tcataattgt catcccatct ttaaagaatg accttaaatt 2460
ttcaaatcta attattttag agttcatttg gatcctttct agcacttttc tagcaatatt 2520
gctgttcctt gtccgccacc tatacataaa gttgctaagc cttttttttgc atctcttttt 2580 tgcattgcgt gtacaagagt aacgagtatt cttgcacctg atgctccaat tggatgacca 2640
agggcaatag ctcctccatt tacatttact ttattcatat caaattttaa atcttttgct 2700

```
actgctaaac tttgagctgc aaaagcttca tttgattcta ttaaatctaa ttcatcaact   2760
gtccaacctg ctttttcaat agctgctttt gttgcataga aaggtccata tcccattatt   2820
gctgggtcaa ctcctgctga accataagaa actatcttag caagtggttt tactccaagc   2880
tctttagctt tttctgcact catgattaca agtactgctg cacagtcatt taatcctgat   2940
gcattaccag ctgtaactgt tccatctttt ttgaaggcag gttttaattt tgcaagtcct   3000
tctatagttg atccaaatct agggtgctca tctgtatcaa ctacagtttc tccctttctg   3060
cctttaatta ctacaggaac tatttcatct ttaaattgac ctgattttat agcttcttca   3120
gctttttttt gtgatgcaag agcaaactca tcttgttctt ctcttgaaat gttccatctc   3180
tcagctatgt ttctgctgt tattcccatg tggtaatcat taaatgcatc ccacaatccg   3240
tcagtgatca tttcatcaac aaatttagcg tttcccattc tatatcccca tctagcgtta   3300
ttcgctaagt aaggagctct agacatattt tccataccac ctgctattat tacgtcagca   3360
tctcctgctt ttataatttg tgctgctaag ctaactgttc taagtcctga accacaaacc   3420
ttattaatag tcatagctgg aatttcaact ggtaatcctg ctttaaaaga tgcctgtctt   3480
gctggattct gtcctaaacc tgcttgaaga acatttccta aaatgacttc attaacatcc   3540
tctggtttta ttcctgcttt tttaactgct tcctttatag ctgtagctcc taaatctact   3600
gctggtacat ccttaagaga ctttccataa gatccaatcg ctgttcttac tgcactagct   3660
attacaactt ctttcattct aactaacctc ctaaattttg atacgggtcg acctgcaggc   3720
atgcaagctt ggcgtaatca tggtcatagc tgtttcctgt gtgaaattgt tatccgctca   3780
caattccaca caacatacga gccggaagca taaagtgtaa agcctggggt gcctaatgag   3840
tgagctaact cacattaatt gcgttgcgct cactgcccgc tttccagtcg ggaaacctgt   3900
cgtgccagct gcattaatga atcggccaac gcgcggggag aggcggtttg cgtattgggc   3960
gctcttccgc ttcctcgctc actgactcgc tgcgctcggt cgttcggctg cggcgagcgg   4020
tatcagctca ctcaaaggcg gtaatacggt tatccacaga atcaggggat aacgcaggaa   4080
agaacatgtg agcaaaaggc cagcaaaagg ccaggaaccg taaaaaggcc gcgttgctgg   4140
cgtttttcca taggctccgc ccccctgacg agcatcacaa aaatcgacgc tcaagtcaga   4200
ggtggcgaaa cccgacagga ctataaagat accaggcgtt tccccctgga agctccctcg   4260
tgcgctctcc tgttccgacc ctgccgctta ccggatacct gtccgccttt ctcccttcgg   4320
gaagcgtggc gctttctcat agctcacgct gtaggtatct cagttcggtg taggtcgttc   4380
gctccaagct gggctgtgtg cacgaacccc ccgttcagcc cgaccgctgc gccttatccg   4440
gtaactatcg tcttgagtcc aacccggtaa gacacgactt atcgccactg gcagcagcca   4500
ctggtaacag gattagcaga gcgaggtatg taggcggtgc tacagagttc ttgaagtggt   4560
ggcctaacta cggctacact agaaggacag tatttggtat ctgcgctctg ctgaagccag   4620
ttaccttcgg aaaaagagtt ggtagctctt gatccggcaa acaaaccacc gctggtagcg   4680
gtggtttttt tgtttgcaag cagcagatta cgcgcagaaa aaaaggatct caagaagatc   4740
ctttgatctt ttctacgggg tctgacgctc agtggaacga aaactcacgt taagggattt   4800
tggtcatgag attatcaaaa aggatcttca cctagatcct tttaaattaa aaatgaagtt   4860
ttaaatcaat ctaaagtata tatgagtaaa cttggtctga cagttaccaa tgcttaatca   4920
gtgaggcacc tatctcagcg atctgtctat ttcgttcatc catagttgcc tgactccccg   4980
tcgtgtagat aactacgata cgggagggct taccatctgg ccccagtgct gcaatgatac   5040
cgcgagaccc acgctcaccg gctccagatt tatcagcaat aaaccagcca gccggaaggg   5100
```

```
ccgagcgcag aagtggtcct gcaactttat ccgcctccat ccagtctatt aattgttgcc   5160

gggaagctag agtaagtagt tcgccagtta atagtttgcg caacgttgtt gccattgcta   5220

caggcatcgt ggtgtcacgc tcgtcgtttg gtatggcttc attcagctcc ggttcccaac   5280

gatcaaggcg agttacatga tcccccatgt tgtgcaaaaa agcggttagc tccttcggtc   5340

ctccgatcgt tgtcagaagt aagttggccg cagtgttatc actcatggtt atggcagcac   5400

tgcataattc tcttactgtc atgccatccg taagatgctt ttctgtgact ggtgagtact   5460

caaccaagtc attctgagaa tagtgtatgc ggcgaccgag ttgctcttgc ccggcgtcaa   5520

tacgggataa taccgcgcca catagcagaa ctttaaaagt gctcatcatt ggaaaacgtt   5580

cttcggggcg aaaactctca aggatcttac cgctgttgag atccagttcg atgtaaccca   5640

ctcgtgcacc caactgatct tcagcatctt ttactttcac cagcgtttct gggtgagcaa   5700

aaacaggaag gcaaaatgcc gcaaaaaagg gaataagggc gacacggaaa tgttgaatac   5760

tcatactctt cctttttcaa tattattgaa gcatttatca gggttattgt ctcatgagcg   5820

gatacatatt tgaatgtatt tagaaaaata aacaaatagg ggttccgcgc acatttcccc   5880

gaaaagtgcc acctgacgtc taagaaacca ttattatcat gacattaacc tataaaaata   5940

ggcgtatcac gaggcccttt cgtc                                          5964
```

<210> SEQ ID NO 13
<211> LENGTH: 4151
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 13

```
gatccagatc tcatcaccat caccatcact aagcttaatt agctgagctt ggactcctgt     60

tgatagatcc agtaatgacc tcagaactcc atctggattt gttcagaacg ctcggttgcc    120

gccgggcgtt ttttattggt gagaatccaa gctagcttgg cgagattttc aggagctaag    180

gaagctaaaa tggagaaaaa aatcactgga tataccaccg ttgatatatc ccaatggcat    240

cgtaaagaac attttgaggc atttcagtca gttgctcaat gtacctataa ccagaccgtt    300

cagctggata ttacggcctt tttaaagacc gtaaagaaaa ataagcacaa gttttatccg    360

gcctttattc acattcttgc ccgcctgatg aatgctcatc cggaatttcg tatggcaatg    420

aaagacggtg agctggtgat atgggatagt gttcaccctt gttacaccgt tttccatgag    480

caaactgaaa cgttttcatc gctctggagt gaataccacg acgatttccg gcagtttcta    540

cacatatatt cgcaagatgt ggcgtgttac ggtgaaaacc tggcctattt ccctaaaggg    600

tttattgaga atatgttttt cgtctcagcc aatccctggg tgagtttcac cagttttgat    660

ttaaacgtgg ccaatatgga caacttcttc gcccccgttt tcaccatgca tgggcaaata    720

ttatacgcaa ggcgacaagg tgctgatgcc gctggcgatt caggttcatc atgccgtctg    780

tgatggcttc catgtcggca gaatgcttaa tgaattacaa cagtactgcg atgagtggca    840

gggcggggcg taattttttt aaggcagtta ttggtgccct taaacgcctg gggtaatgac    900

tctctagctt gaggcatcaa ataaaacgaa aggctcagtc gaaagactgg gcctttcgtt    960

ttatctgttg tttgtcggtg aacgctctcc tgagtaggac aaatccgccg ctctagagct   1020

gcctcgcgcg tttcggtgat gacggtgaaa acctctgaca catgcagctc ccggagacgg   1080

tcacagcttg tctgtaagcg gatgccggga gcagacaagc ccgtcagggc gcgtcagcgg   1140
```

```
gtgttggcgg gtgtcggggc gcagccatga cccagtcacg tagcgatagc ggagtgtata   1200
ctggcttaac tatgcggcat cagagcagat tgtactgaga gtgcaccata tgcggtgtga   1260
aataccgcac agatgcgtaa ggagaaaata ccgcatcagg cgctcttccg cttcctcgct   1320
cactgactcg ctgcgctcgg tctgtcggct gcggcgagcg gtatcagctc actcaaaggc   1380
ggtaatacgg ttatccacag aatcagggga taacgcagga aagaacatgt gagcaaaagg   1440
ccagcaaaag gccaggaacc gtaaaaaggc cgcgttgctg gcgtttttcc ataggctccg   1500
cccccctgac gagcatcaca aaaatcgacg ctcaagtcag aggtggcgaa acccgacagg   1560
actataaaga taccaggcgt ttccccctgg aagctccctc gtgcgctctc ctgttccgac   1620
cctgccgctt accggatacc tgtccgcctt tctcccttcg ggaagcgtgg cgctttctca   1680
atgctcacgc tgtaggtatc tcagttcggt gtaggtcgtt cgctccaagc tgggctgtgt   1740
gcacgaaccc cccgttcagc ccgaccgctg cgccttatcc ggtaactatc gtcttgagtc   1800
caacccggta agacacgact tatcgccact ggcagcagcc actggtaaca ggattagcag   1860
agcgaggtat gtaggcggtg ctacagagtt cttgaagtgg tggcctaact acggctacac   1920
tagaaggaca gtatttggta tctgcgctct gctgaagcca gttaccttcg gaaaaagagt   1980
tggtagctct tgatccggca aacaaaccac cgctggtagc ggtggttttt ttgtttgcaa   2040
gcagcagatt acgcgcagaa aaaaaggatc tcaagaagat cctttgatct tttctacggg   2100
gtctgacgct cagtggaacg aaaactcacg ttaagggatt ttggtcatga gattatcaaa   2160
aaggatcttc acctagatcc ttttaaatta aaaatgaagt tttaaatcaa tctaaagtat   2220
atatgagtaa acttggtctg acagttacca atgcttaatc agtgaggcac ctatctcagc   2280
gatctgtcta tttcgttcat ccatagctgc ctgactcccc gtcgtgtaga taactacgat   2340
acgggagggc ttaccatctg gccccagtgc tgcaatgata ccgcgagacc cacgctcacc   2400
ggctccagat ttatcagcaa taaaccagcc agccggaagg gccgagcgca gaagtggtcc   2460
tgcaacttta tccgcctcca tccagtctat taattgttgc cgggaagcta gagtaagtag   2520
ttcgccagtt aatagtttgc gcaacgttgt tgccattgct acaggcatcg tggtgtcacg   2580
ctcgtcgttt ggtatggctt cattcagctc cggttcccaa cgatcaaggc gagttacatg   2640
atcccccatg ttgtgcaaaa aagcggttag ctccttcggt cctccgatcg ttgtcagaag   2700
taagttggcc gcagtgttat cactcatggt tatggcagca ctgcataatt ctcttactgt   2760
catgccatcc gtaagatgct tttctgtgac tggtgagtac tcaaccaagt cattctgaga   2820
atagtgtatg cggcgaccga gttgctcttg cccggcgtca atacgggata ataccgcgcc   2880
acatagcaga actttaaaag tgctcatcat tggaaaacgt tcttcggggc gaaaactctc   2940
aaggatctta ccgctgttga gatccagttc gatgtaaccc actcgtgcac ccaactgatc   3000
ttcagcatct tttactttca ccagcgtttc tgggtgagca aaaacaggaa ggcaaaatgc   3060
cgcaaaaaag ggaataaggg cgacacggaa atgttgaata ctcatactct tcctttttca   3120
atattattga agcatttatc agggttattg tctcatgagc ggatacatat ttgaatgtat   3180
ttagaaaaat aaacaaatag gggttccgcg cacatttccc cgaaaagtgc cacctgacgt   3240
ctaagaaacc attattatca tgacattaac ctataaaaat aggcgtatca cgaggccctt   3300
tcgtcttcac ctcgagaaat cataaaaaat ttatttgctt tgtgagcgga taacaattat   3360
aatagattca attgtgagcg gataacaatt tcacacagaa ttcattaaag aggagaaatt   3420
aaccatgggc caactcttca aatcatttga tgcgtcggaa aaaacacagc tcatctgttt   3480
```

```
tccgtttgcc ggcggctatt cggcgtcgtt tcgccctctc catgcttttt tgcaggggga   3540

gtgcgagatg ctcgctgccg agccgccggg acacggcacg aatcaaacgt cagccattga   3600

ggatctcgaa gagctgacgg atttgtacaa gcaagaactg aaccttcgcc ctgatcggcc   3660

gtttgtgctg ttcggacaca gtatgggcgg aatgatcacc ttcaggctgg cgcaaaagct   3720

tgagcgtgaa ggcatctttc cgcaggcggt tatcatttct gcaatccagc cgcctcatat   3780

tcagcggaag aaagtgtccc acctgcctga tgatcagttt ctcgatcata ttatccaatt   3840

aggcggaatg cccgcagagc ttgttgaaaa taaggaggtc atgtcctttt tcctgccttc   3900

tttccgatca gattaccggg ctcttgaaca atttgagctt tacgatctgg cccagatcca   3960

gtcgcctgtt catgtcttta acgggcttga tgataaaaaa tgcatacgag atgcggaagg   4020

gtggaagaag tgggcaaaag acatcacatt ccatcaattt gacggcgggc acatgttcct   4080

gctgtcacaa acggaagaag tcgcagaacg gatttttgcg atcttgaatc agcatccgat   4140

cattcaaccg g                                                        4151
```

<210> SEQ ID NO 14
<211> LENGTH: 5964
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 14

```
tcgcgcgttt cggtgatgac ggtgaaaacc tctgacacat gcagctcccg gagacggtca     60

cagcttgtct gtaagcggat gccgggagca gacaagcccg tcagggcgcg tcagcgggtg    120

ttggcgggtg tcggggctgg cttaactatg cggcatcaga gcagattgta ctgagagtgc    180

accatatgcg gtgtgaaata ccgcacagat gcgtaaggag aaaataccgc atcaggcgcc    240

attcgccatt caggctgcgc aactgttggg aagggcgatc ggtgcgggcc tcttcgctat    300

tacgccagct ggcgaaaggg ggatgtgctg caaggcgatt aagttgggta acgccagggt    360

tttcccagtc acgacgttgt aaaacgacgg ccagtgccaa gcttgcatgc ctgcaggtcg    420

acccgtatca aaatttagga ggttagttag aatgaaagaa gttgtaatag ctagtgcagt    480

aagaacagcg attggatctt atggaaagtc tcttaaggat gtaccagcag tagatttagg    540

agctacagct ataaaggaag cagttaaaaa agcaggaata aaaccagagg atgttaatga    600

agtcatttta ggaaatgttc ttcaagcagg tttaggacag aatccagcaa gacaggcatc    660

ttttaaagca ggattaccag ttgaaattcc agctatgact attaataagg tttgtggttc    720

aggacttaga acagttagct tagcagcaca aattataaaa gcaggagatg ctgacgtaat    780

aatagcaggt ggtatggaaa atatgtctag agctccttac ttagcgaata acgctagatg    840

gggatataga atgggaaacg ctaaatttgt tgatgaaatg atcactgacg gattgtggga    900

tgcatttaat gattaccaca tgggaataac agcagaaaac atagctgaga gatggaacat    960

ttcaagagaa gaacaagatg agtttgctct tgcatcacaa aaaaaagctg aagaagctat   1020

aaaatcaggt caatttaaag atgaaatagt tcctgtagta attaaaggca gaaagggaga   1080

aactgtagtt gatacagatg agcaccctag atttggatca actatagaag gacttgcaaa   1140

attaaaacct gccttcaaaa aagatggaac agttacagct ggtaatgcat caggattaaa   1200

tgactgtgca gcagtacttg taatcatgag tgcagaaaaa gctaaagagc ttggagtaaa   1260

accacttgct aagatagttt cttatggttc agcaggagtt gacccagcaa taatgggata   1320
```

-continued

```
tggacctttc tatgcaacaa aagcagctat tgaaaaagca ggttggacag ttgatgaatt   1380
agatttaata gaatcaaatg aagcttttgc agctcaaagt ttagcagtag caaaagattt   1440
aaaatttgat atgaataaag taaatgtaaa tggaggagct attgcccttg gtcatccaat   1500
tggagcatca ggtgcaagaa tactcgttac tcttgtacac gcaatgcaaa aaagagatgc   1560
aaaaaaaggc ttagcaactt tatgtatagg tggcggacaa ggaacagcaa tattgctaga   1620
aaagtgctag aaaggatcca aatgaactct aaaataatta gatttgaaaa tttaaggtca   1680
ttctttaaag atgggatgac aattatgatt ggaggttttt taaactgtgg cactccaacc   1740
aaattaattg atttttagt taatttaaat ataaagaatt taacgattat aagtaatgat   1800
acatgttatc ctaatacagg tattggtaag ttaatatcaa ataatcaagt aaaaaagctt   1860
attgcttcat atataggcag caacccagat actggcaaaa aactttttaa taatgaactt   1920
gaagtagagc tctctcccca aggaactcta gtggaaagaa tacgtgcagg cggatctggc   1980
ttaggtggtg tactaactaa aacaggttta ggaactttga ttgaaaaagg aaagaaaaaa   2040
atatctataa atggaacgga atatttgtta gagctacctc ttacagccga tgtagcatta   2100
attaaaggta gtattgtaga tgaggccgga aacaccttct ataaaggtac tactaaaaac   2160
tttaatccct atatggcaat ggcagctaaa accgtaatag ttgaagctga aaatttagtt   2220
agctgtgaaa aactagaaaa ggaaaaagca atgacccccg gagttcttat aaattatata   2280
gtaaaggagc ctgcataaaa tgattaatga taaaaaccta gcgaaagaaa taatagccaa   2340
aagagttgca agagaattaa aaaatggtca acttgtaaac ttaggtgtag gtcttcctac   2400
catggttgca gattatatac caaaaaattt caaaattact ttccaatcag aaaacggaat   2460
agttggaatg ggcgctagtc ctaaaataaa tgaggcagat aaagatgtag taaatgcagg   2520
aggagactat acaacagtac ttcctgacgg cacatttttc gatagctcag tttcgttttc   2580
actaatccgt ggtggtcacg tagatgttac tgttttaggg gctctccagg tagatgaaaa   2640
gggtaatata gccaattgga ttgttcctgg aaaaatgctc tctggtatgg gtggagctat   2700
ggatttagta aatggagcta agaaagtaat aattgcaatg agacatacaa ataaaggtca   2760
acctaaaatt ttaaaaaaat gtacacttcc cctcacggca aagtctcaag caaatctaat   2820
tgtaacagaa cttggagtaa ttgaggttat taatgatggt ttacttctca ctgaaattaa   2880
taaaaacaca accattgatg aaataaggtc tttaactgct gcagatttac tcatatccaa   2940
tgaacttaga cccatggctg tttaggtacc ttttatgtta aaggatgaag taattaaaca   3000
aattagcacg ccattaactt cgcctgcatt tcctagagga ccctataaat ttcataatcg   3060
tgagtatttt aacattgtat atcgtacaga tatggatgca cttcgtaaag ttgtgccaga   3120
gcctttagaa attgatgagc ccttagtcag gtttgaaatt atggcaatgc atgatacgag   3180
tggacttggt tgttatacag aaagcggaca ggctattccc gtaagcttta atggagttaa   3240
gggagattat cttcatatga tgtatttaga taatgagcct gcaattgcag taggaaggga   3300
attaagtgca tatcctaaaa agctcgggta tccaaagctt tttgtggatt cagatacttt   3360
agtaggaact ttagactatg gaaaacttag agttgcgaca gctacaatgg ggtacaaaca   3420
taaagcctta gatgctaatg aagcaaagga tcaaatttgt cgccctaatt atatgttgaa   3480
aataataccc aattatgatg gaagccctag aatatgtgag cttataaatg cgaaaatcac   3540
agatgttacc gtacatgaag cttggacagg accaactcga ctgcagttat ttgatcacgc   3600
tatggcgcca cttaatgatt tgccagtaaa agagattgtt tctagctctc acattcttgc   3660
agatataata ttgcctagag ctgaagttat atatgattat cttaagtaat aaaaataaga   3720
```

```
gttacctgaa ttcgtaatca tggtcatagc tgtttcctgt gtgaaattgt tatccgctca   3780
caattccaca caacatacga gccggaagca taaagtgtaa agcctggggt gcctaatgag   3840
tgagctaact cacattaatt gcgttgcgct cactgcccgc tttccagtcg ggaaacctgt   3900
cgtgccagct gcattaatga atcggccaac gcgcggggag aggcggtttg cgtattgggc   3960
gctcttccgc ttcctcgctc actgactcgc tgcgctcggt cgttcggctg cggcgagcgg   4020
tatcagctca ctcaaaggcg gtaatacggt tatccacaga atcaggggat aacgcaggaa   4080
agaacatgtg agcaaaaggc cagcaaaagg ccaggaaccg taaaaaggcc gcgttgctgg   4140
cgtttttcca taggctccgc ccccctgacg agcatcacaa aaatcgacgc tcaagtcaga   4200
ggtggcgaaa cccgacagga ctataaagat accaggcgtt tccccctgga agctccctcg   4260
tgcgctctcc tgttccgacc ctgccgctta ccggatacct gtccgccttt ctcccttcgg   4320
gaagcgtggc gctttctcat agctcacgct gtaggtatct cagttcggtg taggtcgttc   4380
gctccaagct gggctgtgtg cacgaacccc ccgttcagcc cgaccgctgc gccttatccg   4440
gtaactatcg tcttgagtcc aacccggtaa gacacgactt atcgccactg gcagcagcca   4500
ctggtaacag gattagcaga gcgaggtatg taggcggtgc tacagagttc ttgaagtggt   4560
ggcctaacta cggctacact agaaggacag tatttggtat ctgcgctctg ctgaagccag   4620
ttaccttcgg aaaaagagtt ggtagctctt gatccggcaa acaaaccacc gctggtagcg   4680
gtggtttttt tgtttgcaag cagcagatta cgcgcagaaa aaaaggatct caagaagatc   4740
ctttgatctt ttctacgggg tctgacgctc agtggaacga aaactcacgt taagggattt   4800
tggtcatgag attatcaaaa aggatcttca cctagatcct tttaaattaa aaatgaagtt   4860
ttaaatcaat ctaaagtata tatgagtaaa cttggtctga cagttaccaa tgcttaatca   4920
gtgaggcacc tatctcagcg atctgtctat ttcgttcatc catagttgcc tgactccccg   4980
tcgtgtagat aactacgata cgggagggct taccatctgg ccccagtgct gcaatgatac   5040
cgcgagaccc acgctcaccg gctccagatt tatcagcaat aaaccagcca gccggaaggg   5100
ccgagcgcag aagtggtcct gcaactttat ccgcctccat ccagtctatt aattgttgcc   5160
gggaagctag agtaagtagt tcgccagtta atagtttgcg caacgttgtt gccattgcta   5220
caggcatcgt ggtgtcacgc tcgtcgtttg gtatggcttc attcagctcc ggttcccaac   5280
gatcaaggcg agttacatga tcccccatgt tgtgcaaaaa agcggttagc tccttcggtc   5340
ctccgatcgt tgtcagaagt aagttggccg cagtgttatc actcatggtt atggcagcac   5400
tgcataattc tcttactgtc atgccatccg taagatgctt ttctgtgact ggtgagtact   5460
caaccaagtc attctgagaa tagtgtatgc ggcgaccgag ttgctcttgc ccggcgtcaa   5520
tacgggataa taccgcgcca catagcagaa ctttaaaagt gctcatcatt ggaaaacgtt   5580
cttcggggcg aaaactctca aggatcttac cgctgttgag atccagttcg atgtaaccca   5640
ctcgtgcacc caactgatct tcagcatctt ttactttcac cagcgtttct gggtgagcaa   5700
aaacaggaag gcaaaatgcc gcaaaaaagg gaataagggc gacacggaaa tgttgaatac   5760
tcatactctt cctttttcaa tattattgaa gcatttatca gggttattgt ctcatgagcg   5820
gatacatatt tgaatgtatt tagaaaaata aacaaatagg ggttccgcgc acatttcccc   5880
gaaaagtgcc acctgacgtc taagaaacca ttattatcat gacattaacc tataaaaata   5940
ggcgtatcac gaggcccttt cgtc                                          5964
```

<210> SEQ ID NO 15

```
<211> LENGTH: 7849
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 15

aactacgtca ggtggcactt ttcggggaaa tgtgcgcgga acccctattt gtttattttt     60

ctaaatacat tcaaatatgt atccgctcat gagacaataa ccctgataaa tgcttcaata    120

atattgaaaa aggaagagta tgagtattca acatttccgt gtcgccctta ttcccttttt    180

tgcggcattt tgccttcctg tttttgctca cccagaaacg ctggtgaaag taaaagatgc    240

tgaagatcag ttgggtgcac gagtgggtta catcgaactg gatctcaaca gcggtaagat    300

ccttgagagt tttcgccccg aagaacgttc tccaatgatg agcactttta aagttctgct    360

atgtggcgcg gtattatccc gtgttgacgc cgggcaagag caactcggtc gccgcataca    420

ctattctcag aatgacttgg ttgagtactc accagtcaca gaaaagcatc ttacggatgg    480

catgacagta agagaattat gcagtgctgc cataaccatg agtgataaca ctgcggccaa    540

cttacttctg acaacgatcg gaggaccgaa ggagctaacc gcttttttgc acaacatggg    600

ggatcatgta actcgccttg atcgttggga accggagctg aatgaagcca taccaaacga    660

cgagcgtgac accacgatgc ctgtagcaat ggcaacaacg ttgcgcaaac tattaactgg    720

cgaactactt actctagctt cccggcaaca attaatagac tggatggagg cggataaagt    780

tgcaggacca cttctgcgct cggcccttcc ggctggctgg tttattgctg ataaatctgg    840

agccggtgag cgtgggtctc gcggtatcat tgcagcactg gggccagatg gtaagccctc    900

ccgtatcgta gttatctaca cgacggggag tcaggcaact atggatgaac gaaatagaca    960

gatcgctgag ataggtgcct cactgattaa gcattggtaa ctgtcagacc aagtttactc   1020

atatatactt tagattgatt taccccggtt gataatcaga aaagccccaa aaacaggaag   1080

attgtataag caaatattta aattgtaaac gttaatattt tgttaaaatt cgcgttaaat   1140

ttttgttaaa tcagctcatt ttttaaccaa taggccgaaa tcggcaaaat cccttataaa   1200

tcaaaagaat agcccgagat agggttgagt gttgttccag tttggaacaa gagtccacta   1260

ttaaagaacg tggactccaa cgtcaaaggg cgaaaaaccg tctatcaggg cgatggccca   1320

ctacgtgaac catcacccaa atcaagtttt ttggggtcga ggtgccgtaa agcactaaat   1380

cggaacccta aagggagccc ccgatttaga gcttgacggg gaaagccggc gaacgtggcg   1440

agaaaggaag ggaagaaagc gaaaggagcg ggcgctaggg cgctggcaag tgtagcggtc   1500

acgctgcgcg taaccaccac acccgccgcg cttaatgcgc cgctacaggg cgcgtaaaag   1560

gatctaggtg aagatccttt ttgataatct catgaccaaa atcccttaac gtgagttttc   1620

gttccactga gcgtcagacc ccgtagaaaa gatcaaagga tcttcttgag atcctttttt   1680

tctgcgcgta atctgctgct tgcaaacaaa aaaaccaccg ctaccagcgg tggtttgttt   1740

gccggatcaa gagctaccaa ctctttttcc gaaggtaact ggcttcagca gagcgcagat   1800

accaaatact gtccttctag tgtagccgta gttaggccac cacttcaaga actctgtagc   1860

accgcctaca tacctcgctc tgctaatcct gttaccagtg gctgctgcca gtggcgataa   1920

gtcgtgtctt accgggttgg actcaagacg atagttaccg gataaggcgc agcggtcggg   1980

ctgaacgggg ggttcgtgca cacagcccag cttggagcga acgacctaca ccgaactgag   2040

atacctacag cgtgagctat gagaaagcgc cacgcttccc gaagggagaa aggcggacag   2100
```

```
gtatccggta agcggcaggg tcggaacagg agagcgcacg agggagcttc caggggggaaa   2160
cgcctggtat ctttatagtc ctgtcgggtt tcgccacctc tgacttgagc gtcgattttt   2220
gtgatgctcg tcaggggggc ggagcctatg gaaaaacgcc agcaacgcgg cctttttacg   2280
gttcctggcc ttttgctggc cttttgctca catgttcttt cctgcgttat cccctgattc   2340
tgtggataac cgtattaccg cctttgagtg agctgatacc gctcgccgca gccgaacgac   2400
cgagcgcagc gagtcagtga gcgaggaagc tatggtgcac tctcagtaca atctgctctg   2460
atgccgcata gttaagccag tatacactcc gctatcgcta cgtgactggg tcatggctgc   2520
gccccgacac ccgccaacac ccgctgacgc gccctgacgg gcttgtctgc tcccggcatc   2580
cgcttacaga caagctgtga ccgtctccgg gagctgcatg tgtcagaggt tttcaccgtc   2640
atcaccgaaa cgcgcgaggc agctgcggta aagctcatca gcgtggtcgt gcagcgattc   2700
acagatgtct gcctgttcat ccgcgtccag ctcgttgagt ttctccagaa gcgttaatgt   2760
ctggcttctg ataaagcggg ccatgttaag ggcggttttt tcctgtttgg tcactgatgc   2820
ctccgtgtaa gggggatttc tgttcatggg ggtaatgata ccgatgaaac gagagaggat   2880
gctcacgata cgggttactg atgatgaaca tgcccggtta ctggaacgtt gtgagggtaa   2940
acaactggcg gtatggatgc ggcgggacca gagaaaaatc actcagggtc aatgccagcc   3000
gaacgccagc aagacgtagc ccagcgcgtc ggccgccatg ccggcgataa tggcctgctt   3060
ctcgccgaaa cgtttggtgg cgggaccagt gacgaaggct tgagcgaggg cgtgcaagat   3120
tccgaatacc gcaagcgaca ggccgatcat cgtcgcgctc cagcgaaagc ggtcctcgcc   3180
gaaaatgacc cagagcgctg ccggcacctg tcctacgagt tgcatgataa agaagacagt   3240
cataagtgcg gcgacgatag tcatgccccg cgcccaccgg aaggagctga ctgggttgaa   3300
ggctctcaag ggcatcggtc gagatcccgg tgcctaatga gtgagctaac ttacattaat   3360
tgcgttgcgc tcactgcccg ctttccagtc gggaaacctg tcgtgccagc tgcattaatg   3420
aatcggccaa cgcgcgggga gaggcggttt gcgtattggg cgccagggtg gtttttcttt   3480
tcaccagtga gacgggcaac agctgattgc ccttcaccgc ctggccctga gagagttgca   3540
gcaagcggtc cacgctggtt tgccccagca ggcgaaaatc ctgtttgatg gtggttaacg   3600
gcgggatata acatgagctg tcttcggtat cgtcgtatcc cactaccgag atatccgcac   3660
caacgcgcag cccggactcg gtaatggcgc gcattgcgcc cagcgccatc tgatcgttgg   3720
caaccagcat cgcagtggga acgatgccct cattcagcat ttgcatggtt tgttgaaaac   3780
cggacatggc actccagtcg ccttcccgtt ccgctatcgg ctgaatttga ttgcgagtga   3840
gatatttatg ccagccagcc agacgcagac gcgccgagac agaacttaat gggcccgcta   3900
acagcgcgat ttgctggtga cccaatgcga ccagatgctc cacgcccagt cgcgtaccgt   3960
cttcatggga gaaaataata ctgttgatgg gtgtctggtc agagacatca agaaataacg   4020
ccggaacatt agtgcaggca gcttccacag caatggcatc ctggtcatcc agcggatagt   4080
taatgatcag cccactgacg cgttgcgcga gaagattgtg caccgccgct ttacaggctt   4140
cgacgccgct tcgttctacc atcgacacca ccacgctggc acccagttga tcggcgcgag   4200
atttaatcgc cgcgacaatt tgcgacggcg cgtgcagggc cagactggag gtggcaacgc   4260
caatcagcaa cgactgtttg cccgccagtt gttgtgccac gcggttggga atgtaattca   4320
gctccgccat cgccgcttcc actttttccc gcgttttcgc agaaacgtgg ctggcctggt   4380
tcaccacgcg ggaaacggtc tgataagaga caccggcata ctctgcgaca tcgtataacg   4440
ttactggttt cacattcacc accctgaatt gactctcttc cgggcgctat catgccatac   4500
```

```
cgcgaaaggt tttgcgccat tcgatggtgt ccgggatctc gacgctctcc cttatgcgac   4560
tcctgcatta ggaagcagcc cagtagtagg ttgaggccgt tgagcaccgc cgccgcaagg   4620
aatggtgcat gccggcatgc cgccctttcg tcttcaagaa ttaattccca attccccagg   4680
catcaaataa aacgaaaggc tcagtcgaaa gactgggcct ttcgttttat ctgttgtttg   4740
tcggtgaacg ctctcctgag taggacaaat ccgccgggag cggatttgaa cgttgcgaag   4800
caacggcccg gagggtggcg ggcaggacgc ccgccataaa ctgccaggaa ttaattcccc   4860
aggcatcaaa taaaacgaaa ggctcagtcg aaagactggg cctttcgttt tatctgttgt   4920
ttgtcggtga acgctctcct gagtaggaca aatccgccgg gagcggattt gaacgttgcg   4980
aagcaacggc ccggagggtg gcgggcagga cgcccgccat aaactgccag gaattaattc   5040
cccaggcatc aaataaaacg aaaggctcag tcgaaagact gggcctttcg ttttatctgt   5100
tgtttgtcgg tgaacgctct cctgagtagg acaaatccgc cgggagcgga tttgaacgtt   5160
gcgaagcaac ggcccggagg gtggcgggca ggacgcccgc cataaactgc caggaattaa   5220
ttccccaggc atcaaataaa acgaaaggct cagtcgaaag actgggcctt tcgttttatc   5280
tgttgtttgt cggtgaacgc tctcctgagt aggacaaatc cgccgggagc ggatttgaac   5340
gttgcgaagc aacggcccgg agggtggcgg gcaggacgcc cgccataaac tgccaggaat   5400
taattcccca ggcatcaaat aaaacgaaag gctcagtcga aagactgggc ctttcgtttt   5460
atctgttgtt tgtcggtgaa cgctctcctg agtaggacaa atccgccggg agcggatttg   5520
aacgttgcga agcaacggcc cggagggtgg cgggcaggac gcccgccata aactgccagg   5580
aattggggat cggaattaat tcccggttta aaccggggat ctcgatcccg cgaaattaat   5640
acgactcact ataggggaat tgtgagcgga taacaattcc cctctagaaa taattttgtt   5700
taactttaag aaggagatat acatatgttg gataatggct ttctcttttcc tgttcgtgtg   5760
tattatgaag atactgatgc aggtggcgta gtgtatcacg ctcgctattt gcattttttt   5820
gaacgagcaa gaacagaata tttgcgtaca ttaaatttta cgcaacaaac cttactagag   5880
gaacaacaac tcgcatttgt tgtcaaaacg ctcgccattg attattgcgt ggcagcaaaa   5940
ttggatgatt tacttatggt ggaaacagag gtttcagaag taaaaggggc tacaatcctt   6000
tttgaacaga gactgatgcg caacaccctg atgttatcaa aggctactgt taaggtagcc   6060
tgtgttgatc taggcaagat gaaaccagtg gcgtttccca aagaagttaa agcggcgttt   6120
catcacttaa aactcgaggg ctcttcctgc tttgccaagg gtaccaatgt tttaatggcg   6180
gatgggtcta ttgaatgtat tgaaaacatt gaggttggta ataaggtcat gggtaaagat   6240
ggcagacctc gtgaggtaat taaattgccc agaggaagag aaactatgta cagcgtcgtg   6300
cagaaaagtc agcacagagc ccacaaaagt gactcaagtc gtgaagtgcc agaattactc   6360
aagtttacgt gtaatgcgac ccatgagttg gttgttagaa cacctcgtag tgtccgccgt   6420
ttgtctcgta ccattaaggg tgtcgaatat tttgaagtta ttacttttga gatgggccaa   6480
aagaaagccc ccgacggtag aattgttgag cttgtcaagg aagtttcaaa gagctaccca   6540
atatctgagg ggcctgagag agccaacgaa ttagtagaat cctatagaaa ggcttcaaat   6600
aaagcttatt ttgagtggac tattgaggcc agagatcttt ctctgttggg ttcccatgtt   6660
cgtaaagcta cctaccagac ttacgctcca attctttatg agaatgacca ctttttcgac   6720
tacatgcaaa aaagtaagtt tcatctcacc attgaaggtc caaaagtact tgcttattta   6780
cttggtttat ggattggtga tggattgtct gacagggcaa ctttttcggt tgattccaga   6840
```

```
gatacttctt tgatggaacg tgttactgaa tatgctgaaa agttgaattt gtgcgccgag   6900
tataaggaca gaaaagaacc acaagttgcc aaaactgtta atttgtactc taaagttgtc   6960
agaggtaatg gtattcgcaa taatcttaat actgagaatc cattatggga cgctattgtt   7020
ggcttaggat tcttgaagga cggtgtcaaa aatattcctt ctttcttgtc tacggacaat   7080
atcggtactc gtgaaacatt tcttgctggt ctaattgatt ctgatggcta tgttactgat   7140
gagcatggta ttaaagcaac aataaagaca attcatactt ctgtcagaga tggtttggtt   7200
tcccttgctc gttctttagg cttagtagtc tcggttaacg cagaacctgc taaggttgac   7260
atgaatgtca ccaaacataa aattagttat gctatttata tgtctggtgg agatgttttg   7320
cttaacgttc tttcgaagtg tgccggctct aaaaaattca ggcctgctcc cgccgctgct   7380
tttgcacgtg agtgccgcgg attttatttc gagttacaag aattgaagga agacgattat   7440
tatgggatta ctttatctga tgattctgat catcagtttt tgcttggatc ccaggttgtc   7500
gtccatgcat gcggtggcct gaccggtctg aactcaggcc tcacgacaaa tcctggtgta   7560
tccgcttggc aggtcaacac agcttatact gcgggacaat tggtcacata taacggcaag   7620
acgtataaat gtttgcagcc ccacacctcc ttggcaggat gggaaccatc caacgttcct   7680
gccttgtggc agcttcaatg actgcaggaa ggggatccgg ctgctaacaa agcccgaaag   7740
gaagctgagt tggctgctgc caccgctgag caataactag cataacccct tggggcctct   7800
aaacgggtct tgaggggttt tttgctgaaa ggaggaacta tatccggat               7849
```

<210> SEQ ID NO 16
<211> LENGTH: 392
<212> TYPE: PRT
<213> ORGANISM: Clostridium acetobutylicum

<400> SEQUENCE: 16

```
Met Lys Glu Val Val Ile Ala Ser Ala Val Arg Thr Ala Ile Gly Ser
1               5                   10                  15

Tyr Gly Lys Ser Leu Lys Asp Val Pro Ala Val Asp Leu Gly Ala Thr
            20                  25                  30

Ala Ile Lys Glu Ala Val Lys Lys Ala Gly Ile Lys Pro Glu Asp Val
        35                  40                  45

Asn Glu Val Ile Leu Gly Asn Val Leu Gln Ala Gly Leu Gly Gln Asn
    50                  55                  60

Pro Ala Arg Gln Ala Ser Phe Lys Ala Gly Leu Pro Val Glu Ile Pro
65                  70                  75                  80

Ala Met Thr Ile Asn Lys Val Cys Gly Ser Gly Leu Arg Thr Val Ser
                85                  90                  95

Leu Ala Ala Gln Ile Ile Lys Ala Gly Asp Ala Asp Val Ile Ile Ala
            100                 105                 110

Gly Gly Met Glu Asn Met Ser Arg Ala Pro Tyr Leu Ala Asn Asn Ala
        115                 120                 125

Arg Trp Gly Tyr Arg Met Gly Asn Ala Lys Phe Val Asp Glu Met Ile
    130                 135                 140

Thr Asp Gly Leu Trp Asp Ala Phe Asn Asp Tyr His Met Gly Ile Thr
145                 150                 155                 160

Ala Glu Asn Ile Ala Glu Arg Trp Asn Ile Ser Arg Glu Glu Gln Asp
                165                 170                 175

Glu Phe Ala Leu Ala Ser Gln Lys Lys Ala Glu Glu Ala Ile Lys Ser
            180                 185                 190

Gly Gln Phe Lys Asp Glu Ile Val Pro Val Val Ile Lys Gly Arg Lys
```

```
        195                 200                 205

Gly Glu Thr Val Val Asp Thr Asp Glu His Pro Arg Phe Gly Ser Thr
    210                 215                 220

Ile Glu Gly Leu Ala Lys Leu Lys Pro Ala Phe Lys Lys Asp Gly Thr
225                 230                 235                 240

Val Thr Ala Gly Asn Ala Ser Gly Leu Asn Asp Cys Ala Ala Val Leu
                245                 250                 255

Val Ile Met Ser Ala Glu Lys Ala Lys Glu Leu Gly Val Lys Pro Leu
            260                 265                 270

Ala Lys Ile Val Ser Tyr Gly Ser Ala Gly Val Asp Pro Ala Ile Met
        275                 280                 285

Gly Tyr Gly Pro Phe Tyr Ala Thr Lys Ala Ala Ile Glu Lys Ala Gly
    290                 295                 300

Trp Thr Val Asp Glu Leu Asp Leu Ile Glu Ser Asn Glu Ala Phe Ala
305                 310                 315                 320

Ala Gln Ser Leu Ala Val Ala Lys Asp Leu Lys Phe Asp Met Asn Lys
                325                 330                 335

Val Asn Val Asn Gly Gly Ala Ile Ala Leu Gly His Pro Ile Gly Ala
            340                 345                 350

Ser Gly Ala Arg Ile Leu Val Thr Leu Val His Ala Met Gln Lys Arg
        355                 360                 365

Asp Ala Lys Lys Gly Leu Ala Thr Leu Cys Ile Gly Gly Gly Gln Gly
    370                 375                 380

Thr Ala Ile Leu Leu Glu Lys Cys
385                 390


<210> SEQ ID NO 17
<211> LENGTH: 1179
<212> TYPE: DNA
<213> ORGANISM: Clostridium acetobutylicum

<400> SEQUENCE: 17

atgaaagaag ttgtaatagc tagtgcagta agaacagcga ttggatctta tggaaagtct      60

cttaaggatg taccagcagt agatttagga gctacagcta taaaggaagc agttaaaaaa     120

gcaggaataa aaccagagga tgttaatgaa gtcattttag gaaatgttct tcaagcaggt     180

ttaggacaga atccagcaag acaggcatct tttaaagcag gattaccagt tgaaattcca     240

gctatgacta ttaataaggt ttgtggttca ggacttagaa cagttagctt agcagcacaa     300

attataaaag caggagatgc tgacgtaata atagcaggtg gtatggaaaa tatgtctaga     360

gctccttact tagcgaataa cgctagatgg ggatatagaa tgggaaacgc taaatttgtt     420

gatgaaatga tcactgacgg attgtgggat gcatttaatg attaccacat gggaataaca     480

gcagaaaaca tagctgagag atggaacatt tcaagagaag aacaagatga gtttgctctt     540

gcatcacaaa aaaaagctga agaagctata aaatcaggtc aatttaaaga tgaaatagtt     600

cctgtagtaa ttaaaggcag aaagggagaa actgtagttg atacagatga gcaccctaga     660

tttggatcaa ctatagaagg acttgcaaaa ttaaaacctg ccttcaaaaa agatggaaca     720

gttacagctg gtaatgcatc aggattaaat gactgtgcag cagtacttgt aatcatgagt     780

gcagaaaaag ctaaagagct tggagtaaaa ccacttgcta agatagtttc ttatggttca     840

gcaggagttg acccagcaat aatgggatat ggacctttct atgcaacaaa agcagctatt     900

gaaaaagcag gttggacagt tgatgaatta gatttaatag aatcaaatga agcttttgca     960

gctcaaagtt tagcagtagc aaaagattta aaatttgata tgaataaagt aaatgtaaat    1020
```

```
ggaggagcta ttgcccttgg tcatccaatt ggagcatcag gtgcaagaat actcgttact   1080

cttgtacacg caatgcaaaa aagagatgca aaaaaaggct tagcaacttt atgtataggt   1140

ggcggacaag gaacagcaat attgctagaa aagtgctag                          1179
```

<210> SEQ ID NO 18
<211> LENGTH: 244
<212> TYPE: PRT
<213> ORGANISM: Clostridium acetobutylicum

<400> SEQUENCE: 18

```
Met Leu Lys Asp Glu Val Ile Lys Gln Ile Ser Thr Pro Leu Thr Ser
1               5                   10                  15

Pro Ala Phe Pro Arg Gly Pro Tyr Lys Phe His Asn Arg Glu Tyr Phe
            20                  25                  30

Asn Ile Val Tyr Arg Thr Asp Met Asp Ala Leu Arg Lys Val Val Pro
        35                  40                  45

Glu Pro Leu Glu Ile Asp Glu Pro Leu Val Arg Phe Glu Ile Met Ala
    50                  55                  60

Met His Asp Thr Ser Gly Leu Gly Cys Tyr Thr Glu Ser Gly Gln Ala
65                  70                  75                  80

Ile Pro Val Ser Cys Asn Gly Val Lys Gly Asp Tyr Leu His Met Met
                85                  90                  95

Tyr Leu Asp Asn Glu Pro Ala Ile Ala Val Gly Arg Glu Leu Ser Ala
            100                 105                 110

Tyr Pro Lys Lys Leu Gly Tyr Pro Lys Leu Phe Val Asp Ser Asp Thr
        115                 120                 125

Leu Val Gly Thr Leu Asp Tyr Gly Lys Leu Arg Val Ala Thr Ala Thr
    130                 135                 140

Met Gly Tyr Lys His Lys Ala Leu Asp Ala Asn Glu Ala Lys Asp Gln
145                 150                 155                 160

Ile Cys Arg Pro Asn Tyr Met Leu Lys Ile Ile Pro Asn Tyr Asp Gly
                165                 170                 175

Ser Pro Arg Ile Cys Glu Leu Ile Asn Ala Lys Ile Thr Asp Val Thr
            180                 185                 190

Val His Glu Ala Trp Thr Gly Pro Thr Arg Leu Gln Leu Phe Asp His
        195                 200                 205

Ala Met Ala Pro Leu Asn Asp Leu Pro Val Lys Glu Ile Val Ser Ser
    210                 215                 220

Ser His Ile Leu Ala Asp Ile Ile Leu Pro Arg Ala Glu Val Ile Tyr
225                 230                 235                 240

Asp Tyr Leu Lys
```

<210> SEQ ID NO 19
<211> LENGTH: 735
<212> TYPE: DNA
<213> ORGANISM: Clostridium acetobutylicum

<400> SEQUENCE: 19

```
atgttaaagg atgaagtaat taaacaaatt agcacgccat taacttcgcc tgcatttcct     60

agaggaccct ataaatttca taatcgtgag tattttaaca ttgtatatcg tacagatatg    120

gatgcacttc gtaaagttgt gccagagcct ttagaaattg atgagccctt agtcaggttt    180

gaaattatgg caatgcatga tacgagtgga cttggttgtt atacagaaag cggacaggct    240

attcccgtaa gctttaatgg agttaaggga gattatcttc atatgatgta tttagataat    300
```

```
gagcctgcaa ttgcagtagg aagggaatta agtgcatatc ctaaaaagct cgggtatcca    360

aagctttttg tggattcaga tactttagta ggaactttag actatggaaa acttagagtt    420

gcgacagcta caatggggta caaacataaa gccttagatg ctaatgaagc aaaggatcaa    480

atttgtcgcc ctaattatat gttgaaaata atacccaatt atgatggaag ccctagaata    540

tgtgagctta taaatgcgaa aatcacagat gttaccgtac atgaagcttg gacaggacca    600

actcgactgc agttatttga tcacgctatg gcgccactta atgatttgcc agtaaaagag    660

attgtttcta gctctcacat tcttgcagat ataatattgc ctagagctga agttatatat    720

gattatctta agtaa                                                     735
```

<210> SEQ ID NO 20
<211> LENGTH: 4616
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 20

```
gcgcccaata cgcaaaccgc ctctccccgc gcgttggccg attcattaat gcagctggca     60

cgacaggttt cccgactgga aagcgggcag tgagcgcaac gcaattaatg tgagttagct    120

cactcattag gcaccccagg ctttacactt tatgcttccg gctcgtatgt tgtgtggaat    180

tgtgagcgga taacaatttc acacaggaaa cagctatgac catgattacg ccaagctcta    240

atacgactca ctatagggaa agctcggtac cacgcatgct gcagacgcgt tacgtatcgg    300

atccagaatt cgtgatggaa ggtacctttt atgttaaagg atgaagtaat taaacaaatt    360

agcacgccat taacttcgcc tgcatttcct agaggaccct ataaatttca taatcgtgag    420

tattttaaca ttgtatatcg tacagatatg gatgcacttc gtaaagttgt gccagagcct    480

ttagaaattg atgagccctt agtcaggttt gaaattatgg caatgcatga tacgagtgga    540

cttggttgtt atacagaaag cggacaggct attcccgtaa gctttaatgg agttaaggga    600

gattatcttc atatgatgta tttagataat gagcctgcaa ttgcagtagg aagggaatta    660

agtgcatatc ctaaaaagct cgggtatcca aagctttttg tggattcaga tactttagta    720

ggaactttag actatggaaa acttagagtt gcgacagcta caatggggta caaacataaa    780

gccttagatg ctaatgaagc aaaggatcaa atttgtcgcc ctaattatat gttgaaaata    840

atacccaatt atgatggaag ccctagaata tgtgagctta taaatgcgaa aatcacagat    900

gttaccgtac atgaagcttg gacaggacca actcgactgc agttatttga tcacgctatg    960

gcgccactta atgatttgcc agtaaaagag attgtttcta gctctcacat tcttgcagat   1020

ataatattgc ctagagctga agttatatat gattatctta agtaatagaa ttcagagtta   1080

catctgaatt cgtcgacaag cttctcgagc ctaggctagc tctagaccac acgtgtgggg   1140

gcccgagctc gcggccgctg tattctatag tgtcacctaa atggccgcac aattcactgg   1200

ccgtcgtttt acaacgtcgt gactgggaaa accctggcgt tacccaactt aatcgccttg   1260

cagcacatcc ccctttcgcc agctggcgta atagcgaaga ggcccgcacc gatcgccctt   1320

cccaacagtt gcgcagcctg aatggcgaat ggaaattgta agcgttaata ttttgttaaa   1380

attcgcgtta aatttttgtt aaatcagctc attttttaac caataggccg aaatcggcaa   1440

aatcccttat aaatcaaaag aatagaccga gatagggttg agtgttgttc cagtttggaa   1500

caagagtcca ctattaaaga acgtggactc caacgtcaaa gggcgaaaaa ccgtctatca   1560
```

```
gggcgatggc ccactacgtg aaccatcacc ctaatcaagt tttttggggt cgaggtgccg   1620

taaagcacta aatcggaacc ctaaagggag cccccgattt agagcttgac ggggaaagcc   1680

ggcgaacgtg gcgagaaagg aagggaagaa agcgaaagga gcgggcgcta gggcgctggc   1740

aagtgtagcg gtcacgctgc gcgtaaccac cacacccgcc gcgcttaatg cgccgctaca   1800

gggcgcgtca ggtggcactt ttcggggaaa tgtgcgcgga acccctattt gtttattttt   1860

ctaaatacat tcaaatatgt atccgctcat gagacaataa ccctgataaa tgcttcaata   1920

atattgaaaa aggaagagta tgagtattca acatttccgt gtcgccctta ttcccttttt   1980

tgcggcattt tgccttcctg tttttgctca cccagaaacg ctggtgaaag taaaagatgc   2040

tgaagatcag ttgggtgcac gagtgggtta catcgaactg gatctcaaca gcggtaagat   2100

ccttgagagt tttcgccccg aagaacgttt tccaatgatg agcactttta aagttctgct   2160

atgtggcgcg gtattatccc gtattgacgc cgggcaagag caactcggtc gccgcataca   2220

ctattctcag aatgacttgg ttgagtactc accagtcaca gaaaagcatc ttacggatgg   2280

catgacagta agagaattat gcagtgctgc cataaccatg agtgataaca ctgcggccaa   2340

cttacttctg acaacgatcg gaggaccgaa ggagctaacc gcttttttgc acaacatggg   2400

ggatcatgta actcgccttg atcgttggga accggagctg aatgaagcca taccaaacga   2460

cgagcgtgac accacgatgc ctgtagcaat ggcaacaacg ttgcgcaaac tattaactgg   2520

cgaactactt actctagctt cccggcaaca attaatagac tggatggagg cggataaagt   2580

tgcaggacca cttctgcgct cggcccttcc ggctggctgg tttattgctg ataaatctgg   2640

agccggtgag cgtgggtctc gcggtatcat tgcagcactg gggccagatg gtaagccctc   2700

ccgtatcgta gttatctaca cgacggggag tcaggcaact atggatgaac gaaatagaca   2760

gatcgctgag ataggtgcct cactgattaa gcattggtaa ctgtcagacc aagtttactc   2820

atatatactt tagattgatt taaaacttca tttttaattt aaaaggatct aggtgaagat   2880

cctttttgat aatctcatga acaataaaac tgtctgctta cataaacagt aatacaaggg   2940

gtgttatgag ccatattcaa cgggaaacgt cttgctctag gccgcgatta aattccaaca   3000

tggatgctga tttatatggg tataaatggg ctcgcgataa tgtcgggcaa tcaggtgcga   3060

caatctatcg attgtatggg aagcccgatg cgccagagtt gtttctgaaa catggcaaag   3120

gtagcgttgc caatgatgtt acagatgaga tggtcagact aaactggctg acggaattta   3180

tgcctcttcc gaccatcaag cattttatcc gtactcctga tgatgcatgg ttactcacca   3240

ctgcgatccc cgggaaaaca gcattccagg tattagaaga atatcctgat tcaggtgaaa   3300

atattgttga tgcgctggca gtgttcctgc gccggttgca ttcgattcct gtttgtaatt   3360

gtccttttaa cagcgatcgc gtatttcgtc tcgctcaggc gcaatcacga atgaataacg   3420

gtttggttga tgcgagtgat tttgatgacg agcgtaatgg ctggcctgtt gaacaagtct   3480

ggaaagaaat gcataaactt ttgccattct caccggattc agtcgtcact catggtgatt   3540

tctcacttga taaccttatt tttgacgagg ggaaattaat aggttgtatt gatgttggac   3600

gagtcggaat cgcagaccga taccaggatc ttgccatcct atggaactgc ctcggtgagt   3660

tttctccttc attacagaaa cggctttttc aaaaatatgg tattgataat cctgatatga   3720

ataaattgca gtttcatttg atgctcgatg agtttttcta agaattaatt catgaccaaa   3780

atcccttaac gtgagttttc gttccactga gcgtcagacc ccgtagaaaa gatcaaagga   3840

tcttcttgag atcctttttt tctgcgcgta atctgctgct tgcaaacaaa aaaaccaccg   3900
```

```
ctaccagcgg tggtttgttt gccggatcaa gagctaccaa ctctttttcc gaaggtaact   3960

ggcttcagca gagcgcagat accaaatact gtccttctag tgtagccgta gttaggccac   4020

cacttcaaga actctgtagc accgcctaca tacctcgctc tgctaatcct gttaccagtg   4080

gctgctgcca gtggcgataa gtcgtgtctt accgggttgg actcaagacg atagttaccg   4140

gataaggcgc agcggtcggg ctgaacgggg ggttcgtgca cacagcccag cttggagcga   4200

acgacctaca ccgaactgag atacctacag cgtgagctat gagaaagcgc cacgcttccc   4260

gaagggagaa aggcggacag gtatccggta agcggcaggg tcggaacagg agagcgcacg   4320

agggagcttc caggggggaaa cgcctggtat ctttatagtc ctgtcgggtt tcgccacctc   4380

tgacttgagc gtcgattttt gtgatgctcg tcaggggggc ggagcctatg gaaaaacgcc   4440

agcaacgcgg cctttttacg gttcctggcc ttttgctggc cttttgctca catgttcttt   4500

cctgcgttat cccctgattc tgtggataac cgtattaccg cctttgagtg agctgatacc   4560

gctcgccgca gccgaacgac cgagcgcagc gagtcagtga gcgaggaagc ggaaga       4616
```

<210> SEQ ID NO 21
<211> LENGTH: 5098
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 21

```
gcgcccaata cgcaaaccgc ctctccccgc gcgttggccg attcattaat gcagctggca     60

cgacaggttt cccgactgga aagcgggcag tgagcgcaac gcaattaatg tgagttagct    120

cactcattag gcaccccagg ctttacactt tatgcttccg gctcgtatgt tgtgtggaat    180

tgtgagcgga taacaatttc acacaggaaa cagctatgac catgattacg ccaagctcta    240

atacgactca ctatagggaa agctcggtac cacgcatgct gcagacgcgt tacgtatcgg    300

atccagaatt cgtgatggtt tatctgtcga cccgtatcaa aatttaggag gttagttaga    360

atgaaagaag ttgtaatagc tagtgcagta agaacagcga ttggatctta tggaaagtct    420

cttaaggatg taccagcagt agatttagga gctacagcta taaaggaagc agttaaaaaa    480

gcaggaataa aaccagagga tgttaatgaa gtcattttag gaaatgttct tcaagcaggt    540

ttaggacaga atccagcaag acaggcatct tttaaagcag gattaccagt tgaaattcca    600

gctatgacta ttaataaggt ttgtggttca ggacttagaa cagttagctt agcagcacaa    660

attataaaag caggagatgc tgacgtaata atagcaggtg gtatggaaaa tatgtctaga    720

gctccttact tagcgaataa cgctagatgg ggatatagaa tgggaaacgc taaatttgtt    780

gatgaaatga tcactgacgg attgtgggat gcatttaatg attaccacat gggaataaca    840

gcagaaaaca tagctgagag atggaacatt tcaagagaag aacaagatga gtttgctctt    900

gcatcacaaa aaaaagctga agaagctata aaatcaggtc aatttaaaga tgaaatagtt    960

cctgtagtaa ttaaaggcag aaagggagaa actgtagttg atacagatga gcaccctaga   1020

tttggatcaa ctatagaagg acttgcaaaa ttaaaacctg ccttcaaaaa agatggaaca   1080

gttacagctg gtaatgcatc aggattaaat gactgtgcag cagtacttgt aatcatgagt   1140

gcagaaaaag ctaaagagct tggagtaaaa ccacttgcta agatagtttc ttatggttca   1200

gcaggagttg acccagcaat aatgggatat ggacctttct atgcaacaaa agcagctatt   1260

gaaaaagcag gttggacagt tgatgaatta gatttaatag aatcaaatga agcttttgca   1320
```

-continued

```
gctcaaagtt tagcagtagc aaaagattta aaatttgata tgaataaagt aaatgtaaat   1380
ggaggagcta ttgcccttgg tcatccaatt ggagcatcag gtgcaagaat actcgttact   1440
cttgtacacg caatgcaaaa aagagatgca aaaaaaggct tagcaacttt atgtataggt   1500
ggcggacaag gaacagcaat attgctagaa aagtgctaga aaggatcctt aaaaataact   1560
ctgatctgaa ttcgtcgaca agcttctcga gcctaggcta gctctagacc acacgtgtgg   1620
gggcccgagc tcgcggccgc tgtattctat agtgtcacct aaatggccgc acaattcact   1680
ggccgtcgtt ttacaacgtc gtgactggga aaaccctggc gttacccaac ttaatcgcct   1740
tgcagcacat ccccctttcg ccagctggcg taatagcgaa gaggcccgca ccgatcgccc   1800
ttcccaacag ttgcgcagcc tgaatggcga atggaaattg taagcgttaa tattttgtta   1860
aaattcgcgt taaatttttg ttaaatcagc tcatttttta accaataggc cgaaatcggc   1920
aaaatccctt ataaatcaaa agaatagacc gagatagggt tgagtgttgt tccagtttgg   1980
aacaagagtc cactattaaa gaacgtggac tccaacgtca aagggcgaaa aaccgtctat   2040
cagggcgatg gcccactacg tgaaccatca ccctaatcaa gttttttggg gtcgaggtgc   2100
cgtaaagcac taaatcggaa ccctaaaggg agcccccgat ttagagcttg acggggaaag   2160
ccggcgaacg tggcgagaaa ggaagggaag aaagcgaaag gagcgggcgc tagggcgctg   2220
gcaagtgtag cggtcacgct gcgcgtaacc accacacccg ccgcgcttaa tgcgccgcta   2280
cagggcgcgt caggtggcac ttttcgggga aatgtgcgcg gaacccctat ttgtttattt   2340
ttctaaatac attcaaatat gtatccgctc atgagacaat aaccctgata aatgcttcaa   2400
taatattgaa aaaggaagag tatgagtatt caacatttcc gtgtcgccct tattcccttt   2460
tttgcggcat tttgccttcc tgtttttgct cacccagaaa cgctggtgaa agtaaaagat   2520
gctgaagatc agttgggtgc acgagtgggt tacatcgaac tggatctcaa cagcggtaag   2580
atccttgaga gttttcgccc cgaagaacgt tttccaatga tgagcacttt taaagttctg   2640
ctatgtggcg cggtattatc ccgtattgac gccgggcaag agcaactcgg tcgccgcata   2700
cactattctc agaatgactt ggttgagtac tcaccagtca cagaaaagca tcttacggat   2760
ggcatgacag taagagaatt atgcagtgct gccataacca tgagtgataa cactgcggcc   2820
aacttacttc tgacaacgat cggaggaccg aaggagctaa ccgctttttt gcacaacatg   2880
ggggatcatg taactcgcct tgatcgttgg gaaccggagc tgaatgaagc cataccaaac   2940
gacgagcgtg acaccacgat gcctgtagca atggcaacaa cgttgcgcaa actattaact   3000
ggcgaactac ttactctagc ttcccggcaa caattaatag actggatgga ggcggataaa   3060
gttgcaggac cacttctgcg ctcggccctt ccggctggct ggtttattgc tgataaatct   3120
ggagccggtg agcgtgggtc tcgcggtatc attgcagcac tggggccaga tggtaagccc   3180
tcccgtatcg tagttatcta cacgacgggg agtcaggcaa ctatggatga acgaaataga   3240
cagatcgctg agataggtgc ctcactgatt aagcattggt aactgtcaga ccaagtttac   3300
tcatatatac tttagattga tttaaaactt catttttaat ttaaaaggat ctaggtgaag   3360
atcctttttg ataatctcat gaacaataaa actgtctgct tacataaaca gtaatacaag   3420
gggtgttatg agccatattc aacgggaaac gtcttgctct aggccgcgat taaattccaa   3480
catggatgct gatttatatg ggtataaatg ggctcgcgat aatgtcgggc aatcaggtgc   3540
gacaatctat cgattgtatg ggaagcccga tgcgccagag ttgtttctga aacatggcaa   3600
aggtagcgtt gccaatgatg ttacagatga gatggtcaga ctaaactggc tgacggaatt   3660
tatgcctctt ccgaccatca agcattttat ccgtactcct gatgatgcat ggttactcac   3720
```

```
cactgcgatc cccgggaaaa cagcattcca ggtattagaa gaatatcctg attcaggtga   3780

aaatattgtt gatgcgctgg cagtgttcct gcgccggttg cattcgattc ctgtttgtaa   3840

ttgtcctttt aacagcgatc gcgtatttcg tctcgctcag gcgcaatcac gaatgaataa   3900

cggtttggtt gatgcgagtg attttgatga cgagcgtaat ggctggcctg ttgaacaagt   3960

ctggaaagaa atgcataaac ttttgccatt ctcaccggat tcagtcgtca ctcatggtga   4020

tttctcactt gataacctta tttttgacga ggggaaatta ataggttgta ttgatgttgg   4080

acgagtcgga atcgcagacc gataccagga tcttgccatc ctatggaact gcctcggtga   4140

gttttctcct tcattacaga aacggctttt tcaaaaatat ggtattgata atcctgatat   4200

gaataaattg cagtttcatt tgatgctcga tgagtttttc taagaattaa ttcatgacca   4260

aaatccctta acgtgagttt tcgttccact gagcgtcaga ccccgtagaa aagatcaaag   4320

gatcttcttg agatcctttt tttctgcgcg taatctgctg cttgcaaaca aaaaaaccac   4380

cgctaccagc ggtggtttgt ttgccggatc aagagctacc aactcttttt ccgaaggtaa   4440

ctggcttcag cagagcgcag ataccaaata ctgtccttct agtgtagccg tagttaggcc   4500

accacttcaa gaactctgta gcaccgccta catacctcgc tctgctaatc ctgttaccag   4560

tggctgctgc cagtggcgat aagtcgtgtc ttaccgggtt ggactcaaga cgatagttac   4620

cggataaggc gcagcggtcg ggctgaacgg ggggttcgtg cacacagccc agcttggagc   4680

gaacgaccta caccgaactg agatacctac agcgtgagct atgagaaagc gccacgcttc   4740

ccgaagggag aaaggcggac aggtatccgg taagcggcag ggtcggaaca ggagagcgca   4800

cgagggagct tccaggggga aacgcctggt atctttatag tcctgtcggg tttcgccacc   4860

tctgacttga gcgtcgattt ttgtgatgct cgtcaggggg gcggagccta tggaaaaacg   4920

ccagcaacgc ggccttttta cggttcctgg ccttttgctg gccttttgct cacatgttct   4980

ttcctgcgtt atcccctgat tctgtggata accgtattac cgcctttgag tgagctgata   5040

ccgctcgccg cagccgaacg accgagcgca gcgagtcagt gagcgaggaa gcggaaga     5098
```

```
<210> SEQ ID NO 22
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 22

atatacatat gttggataat ggcttttc                                         28


<210> SEQ ID NO 23
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 23

tccgaactcg agttttaagt gatg                                             24


<210> SEQ ID NO 24
<211> LENGTH: 24
<212> TYPE: DNA
<213> ORGANISM: Artificial Sequence
```

<220> FEATURE:
<223> OTHER INFORMATION: Description of Artificial Sequence: Synthetic primer

<400> SEQUENCE: 24
catgctcgag acgcgttacg tatc 24

<210> SEQ ID NO 25
<211> LENGTH: 28
<212> TYPE: DNA
<213> ORGANISM: Artificial Sequence
<220> FEATURE:
<223> OTHER INFORMATION: Description of Artificial Sequence: Synthetic primer

<400> SEQUENCE: 25
gatggggccc tgaattctat tacttaag 28

<210> SEQ ID NO 26
<211> LENGTH: 31
<212> TYPE: DNA
<213> ORGANISM: Artificial Sequence
<220> FEATURE:
<223> OTHER INFORMATION: Description of Artificial Sequence: Synthetic primer

<400> SEQUENCE: 26
caattgtcga cggataacaa tttcacacag a 31

<210> SEQ ID NO 27
<211> LENGTH: 32
<212> TYPE: DNA
<213> ORGANISM: Artificial Sequence
<220> FEATURE:
<223> OTHER INFORMATION: Description of Artificial Sequence: Synthetic primer

<400> SEQUENCE: 27
ctatcaactc gagtccaagc tcagctaatt aa 32

<210> SEQ ID NO 28
<211> LENGTH: 26
<212> TYPE: DNA
<213> ORGANISM: Artificial Sequence
<220> FEATURE:
<223> OTHER INFORMATION: Description of Artificial Sequence: Synthetic primer

<400> SEQUENCE: 28
catgatttcc cgggggttag catatg 26

<210> SEQ ID NO 29
<211> LENGTH: 31
<212> TYPE: DNA
<213> ORGANISM: Artificial Sequence
<220> FEATURE:
<223> OTHER INFORMATION: Description of Artificial Sequence: Synthetic primer

<400> SEQUENCE: 29
cagagttatt tttaagtcga ctttctagca c 31

<210> SEQ ID NO 30
<211> LENGTH: 25
<212> TYPE: DNA
<213> ORGANISM: Artificial Sequence

```
<220> FEATURE:
<223> OTHER INFORMATION: Description of Artificial Sequence: Synthetic
      primer

<400> SEQUENCE: 30

gtcgacccgg gtcaaaattt aggag                                           25


<210> SEQ ID NO 31
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 31

gcttgtcgaa ttcagatcag ag                                              22


<210> SEQ ID NO 32
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 32

caattgggat ccgataacaa tttcacacag                                      30


<210> SEQ ID NO 33
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 33

gagatctggt acccggttaa atgatcgga                                       29


<210> SEQ ID NO 34
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 34

catgatttgt cgacggttag catatg                                          26


<210> SEQ ID NO 35
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 35

cagagttatt tttaaggatc ctttctagc                                       29


<210> SEQ ID NO 36
<211> LENGTH: 28
<212> TYPE: DNA
<213> ORGANISM: Artificial Sequence
```

```
<220> FEATURE:
<223> OTHER INFORMATION: Description of Artificial Sequence: Synthetic
      primer

<400> SEQUENCE: 36

ctctagaagg atcctgttta actttaag                                    28


<210> SEQ ID NO 37
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 37

attgggtacc tcattgcata ctccg                                       25
```